(12) United States Patent
Makower et al.

(10) Patent No.: US 8,187,297 B2
(45) Date of Patent: May 29, 2012

(54) DEVICES AND METHODS FOR TREATMENT OF OBESITY

(75) Inventors: Joshua Makower, Los Altos, CA (US); Steven Kim, Los Altos, CA (US); Brian K. Shiu, Sunnyvale, CA (US); Shuji Uemura, San Francisco, CA (US); Pablo G. Acosta, Newark, CA (US)

(73) Assignee: Vibsynt, Inc., Redwood City, CA (US)

( * ) Notice: Subject to any disclaimer, the term of this patent is extended or adjusted under 35 U.S.C. 154(b) by 1318 days.

(21) Appl. No.: 11/881,144

(22) Filed: Jul. 24, 2007

(65) Prior Publication Data

US 2008/0051823 A1 Feb. 28, 2008

Related U.S. Application Data

(63) Continuation-in-part of application No. 11/716,986, filed on Mar. 10, 2007, and a continuation-in-part of application No. 11/716,985, filed on Mar. 10, 2007, said application No. 11/716,986 is a continuation-in-part of application No. 11/407,701, filed on Apr. 19, 2006, now Pat. No. 8,070,768, said application No. 11/716,985 is a continuation-in-part of application No. 11/407,701.

(60) Provisional application No. 60/877,595, filed on Dec. 28, 2006, provisional application No. 60/833,284, filed on Jul. 24, 2006.

(51) Int. Cl.
*A61M 29/00* (2006.01)
*A61B 17/00* (2006.01)
*A61B 19/00* (2006.01)
*A61F 2/00* (2006.01)
*A61F 13/00* (2006.01)

(52) U.S. Cl. ........ 606/192; 606/191; 606/198; 606/201; 600/37; 128/898

(58) Field of Classification Search ............... 606/119, 606/151, 191, 192, 198, 201, 203; 600/37; 128/898
See application file for complete search history.

(56) References Cited

U.S. PATENT DOCUMENTS

| 233,475 A | 10/1880 | Cook et al. |
| 659,422 A | 10/1900 | Shidler |
| 780,392 A | 1/1905 | Wanamaker et al. |

(Continued)

FOREIGN PATENT DOCUMENTS

EP 1 016 377 A2 7/2000

(Continued)

OTHER PUBLICATIONS

McMillan, et al., Arthroscopic Knot-tying techiniques. pp. 81-95, 2003.

(Continued)

*Primary Examiner* — Gary Jackson
*Assistant Examiner* — Michael Medoza
(74) *Attorney, Agent, or Firm* — Alan W. Cannon

(57) ABSTRACT

Devices, methods for treatment of obesity, as well as instruments and tools used in placing, adjusting and maintaining devices for treatment of obesity. Various embodiments of devices that are implanted extra-gastrically are provided. Various embodiments of devices that are implanted intra-gastrically are provided. Methods include laparoscopic, percutaneous and/or trans-oral methods. Alternatively, devices describe can generally also be implanted by open surgical procedures.

5 Claims, 51 Drawing Sheets

U.S. PATENT DOCUMENTS

| | | | |
|---|---|---|---|
| 789,467 A | 5/1905 | West |
| 1,461,524 A | 7/1923 | Goddard |
| 2,579,192 A | 12/1951 | Kohl et al. |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,571,864 A | 3/1971 | Emile et al. |
| 3,664,435 A | 5/1972 | Klessig |
| 3,675,639 A | 7/1972 | Climber |
| 3,713,680 A | 1/1973 | Pagano |
| 3,756,638 A | 9/1973 | Stockberger |
| 3,873,140 A | 3/1975 | Bloch |
| 3,931,667 A | 1/1976 | Merser et al. |
| 3,976,079 A | 8/1976 | Samuels et al. |
| 4,006,747 A | 2/1977 | Kronenthal et al. |
| 4,060,089 A | 11/1977 | Noiles |
| 4,133,315 A | 1/1979 | Berman et al. |
| 4,210,148 A | 7/1980 | Stivala |
| 4,246,893 A | 1/1981 | Berson |
| 4,291,698 A | 9/1981 | Fuchs et al. |
| 4,328,805 A | 5/1982 | Akopov et al. |
| 4,416,267 A | 11/1983 | Garren et al. |
| 4,458,681 A | 7/1984 | Hophins |
| 4,472,226 A | 9/1984 | Redinger et al. |
| 4,485,805 A | 12/1984 | Foster, Jr. et al. |
| 4,493,323 A | 1/1985 | Albright et al. |
| 4,558,699 A | 12/1985 | Bashour |
| 4,592,339 A | 6/1986 | Kuzmak et al. |
| 4,592,342 A | 6/1986 | Salmasian |
| 4,621,640 A | 11/1986 | Mulhollan et al. |
| 4,669,473 A | 6/1987 | Richards et al. |
| 4,694,827 A | 9/1987 | Weiner et al. |
| 4,696,288 A | 9/1987 | Kuzmak et al. |
| 4,705,040 A | 11/1987 | Mueller et al. |
| 4,714,281 A | 12/1987 | Peck |
| 4,723,547 A | 2/1988 | Kullas et al. |
| 4,738,255 A | 4/1988 | Goble et al. |
| 4,739,758 A | 4/1988 | Lai et al. |
| 4,744,364 A | 5/1988 | Kensey |
| 4,750,492 A | 6/1988 | Jacobs |
| 4,803,985 A | 2/1989 | Hill |
| 4,823,794 A | 4/1989 | Pierce |
| 4,899,747 A | 2/1990 | Garren et al. |
| 4,955,913 A | 9/1990 | Robinson |
| 5,002,550 A | 3/1991 | Li |
| 5,033,481 A | 7/1991 | Heyler, III |
| 5,041,129 A | 8/1991 | Hayhurst et al. |
| 5,084,061 A | 1/1992 | Gau et al. |
| 5,100,421 A | 3/1992 | Christoudias |
| 5,112,310 A | 5/1992 | Grobe |
| 5,123,914 A | 6/1992 | Cope |
| 5,129,912 A | 7/1992 | Noda et al. |
| RE34,021 E | 8/1992 | Mueller et al. |
| 5,151,086 A | 9/1992 | Duh et al. |
| 5,188,104 A | 2/1993 | Wernicke et al. |
| 5,217,470 A | 6/1993 | Weston |
| 5,234,454 A | 8/1993 | Bangs |
| 5,246,456 A | 9/1993 | Wilkinson |
| 5,258,015 A | 11/1993 | Li et al. |
| 5,259,399 A | 11/1993 | Brown |
| 5,269,809 A | 12/1993 | Hayhurst et al. |
| 5,292,344 A | 3/1994 | Douglas |
| 5,334,200 A | 8/1994 | Johnson |
| 5,354,271 A | 10/1994 | Voda |
| 5,364,408 A | 11/1994 | Gordon |
| 5,391,182 A | 2/1995 | Chin |
| 5,405,352 A | 4/1995 | Weston |
| 5,423,872 A | 6/1995 | Cigaina |
| 5,428,123 A | 6/1995 | Ward et al. |
| 5,433,723 A | 7/1995 | Lindenberg |
| 5,445,608 A | 8/1995 | Chen et al. |
| 5,470,337 A | 11/1995 | Moss |
| 5,472,446 A | 12/1995 | Torre |
| 5,480,406 A | 1/1996 | Nolan et al. |
| 5,496,311 A | 3/1996 | Abele et al. |
| 5,507,754 A | 4/1996 | Green et al. |
| 5,545,171 A | 8/1996 | Sharkey et al. |
| 5,545,178 A | 8/1996 | Kensey et al. |
| 5,549,621 A | 8/1996 | Bessler et al. |
| 5,554,162 A | 9/1996 | DeLange |
| 5,573,540 A | 11/1996 | Yoon |
| 5,591,177 A | 1/1997 | Lehrer |
| 5,601,604 A | 2/1997 | Vincent |
| 5,626,614 A | 5/1997 | Hart |
| 5,634,936 A | 6/1997 | Linden et al. |
| 5,647,836 A | 7/1997 | Blake, III et al. |
| 5,690,691 A | 11/1997 | Chen et al. |
| 5,716,368 A | 2/1998 | Torre et al. |
| 5,725,557 A | 3/1998 | Gatturna et al. |
| 5,846,254 A | 12/1998 | Schulze et al. |
| 5,888,196 A | 3/1999 | Bonutti |
| 5,931,788 A | 8/1999 | Keen et al. |
| 5,938,669 A | 8/1999 | Klaiber et al. |
| 5,951,590 A | 9/1999 | Goldfarb |
| 5,961,440 A | 10/1999 | Schweich, Jr. et al. |
| 5,971,447 A | 10/1999 | Steck, III |
| 5,993,473 A | 11/1999 | Chan et al. |
| 6,013,053 A | 1/2000 | Bower et al. |
| 6,067,991 A | 5/2000 | Forsell |
| 6,080,160 A | 6/2000 | Chen et al. |
| 6,097,984 A | 8/2000 | Douglas |
| 6,102,922 A | 8/2000 | Jakobsson et al. |
| 6,113,609 A | 9/2000 | Adams |
| 6,143,006 A | 11/2000 | Chan |
| 6,162,234 A | 12/2000 | Freedland et al. |
| 6,186,149 B1 | 2/2001 | Pacella et al. |
| 6,270,530 B1 | 8/2001 | Eldridge et al. |
| 6,420,452 B1 | 7/2002 | Gunatillake et al. |
| 6,437,073 B1 | 8/2002 | Gunatillake et al. |
| 6,447,533 B1 | 9/2002 | Adams |
| 6,454,785 B2 | 9/2002 | De Hoyos Garza |
| 6,475,136 B1 | 11/2002 | Forsell |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,148 B1 | 12/2002 | Pinchuk et al. |
| 6,506,196 B1 | 1/2003 | Laufer |
| 6,511,490 B2 | 1/2003 | Robert et al. |
| 6,535,764 B2 | 3/2003 | Imran et al. |
| 6,558,400 B2 | 5/2003 | Deem et al. |
| 6,656,182 B1 | 12/2003 | Hayhurst |
| 6,663,639 B1 | 12/2003 | Laufer et al. |
| 6,669,713 B2 | 12/2003 | Adams |
| 6,675,809 B2 | 1/2004 | Stack et al. |
| 6,736,793 B2 | 5/2004 | Meyer et al. |
| 6,746,460 B2 | 6/2004 | Gannoe et al. |
| 6,755,869 B2 | 6/2004 | Geitz |
| 6,773,441 B1 | 8/2004 | Laufer et al. |
| 6,790,213 B2 | 9/2004 | Cherok et al. |
| 6,821,285 B2 | 11/2004 | Laufer et al. |
| 6,835,200 B2 | 12/2004 | Laufer et al. |
| 6,869,395 B2 | 3/2005 | Page et al. |
| 6,900,055 B1 | 5/2005 | Fuller |
| 6,908,487 B2 | 6/2005 | Cigaina |
| 6,981,978 B2 | 1/2006 | Gannoe |
| 6,994,715 B2 | 2/2006 | Gannoe et al. |
| 7,033,373 B2 | 4/2006 | de la Torre et al. |
| 7,037,344 B2 | 5/2006 | Kagan et al. |
| 7,153,314 B2 | 12/2006 | Laufer et al. |
| 7,167,750 B2 | 1/2007 | Knudson et al. |
| 7,223,277 B2 | 5/2007 | DeLegge |
| 7,255,675 B2 | 8/2007 | Gertner et al. |
| 7,310,557 B2 | 12/2007 | Maschino et al. |
| 7,334,822 B1 | 2/2008 | Hines, Jr. |
| 7,338,433 B2 | 3/2008 | Coe |
| 7,374,565 B2 | 5/2008 | Hassler et al. |
| 7,402,166 B2 | 7/2008 | Feigl |
| 7,354,450 B2 | 8/2008 | Stack et al. |
| 7,416,554 B2 | 8/2008 | Lam et al. |
| 7,534,248 B2 | 5/2009 | Mikkaichi et al. |
| 7,608,578 B2 | 10/2009 | Miller |
| 7,618,426 B2 | 11/2009 | Ewers et al. |
| 7,666,195 B2 | 2/2010 | Kelleher et al. |

| | | |
|---|---|---|
| 7,670,279 B2 | 3/2010 | Gertner |
| 7,717,843 B2 * | 5/2010 | Balbierz et al. .................. 600/37 |
| 7,775,967 B2 | 8/2010 | Gertner |
| 7,824,368 B2 | 11/2010 | Clem et al. |
| 7,841,978 B2 | 11/2010 | Gertner |
| 7,850,660 B2 | 12/2010 | Uth et al. |
| 7,862,546 B2 | 1/2011 | Conlon et al. |
| 7,988,617 B2 | 8/2011 | Gertner |
| 2001/0010005 A1 | 7/2001 | Kammerer et al. |
| 2001/0011543 A1 | 8/2001 | Forsell |
| 2001/0044639 A1 | 11/2001 | Levinson |
| 2001/0049497 A1 | 12/2001 | Kalloo et al. |
| 2002/0055757 A1 | 5/2002 | Flesler et al. |
| 2002/0128694 A1 | 9/2002 | Foerster |
| 2002/0161382 A1 | 10/2002 | Neisz et al. |
| 2002/0161414 A1 | 10/2002 | Flesler et al. |
| 2002/0188354 A1 | 12/2002 | Peghini et al. |
| 2003/0021822 A1 | 1/2003 | Lloyd |
| 2003/0055463 A1 | 3/2003 | Gordon et al. |
| 2003/0055465 A1 | 3/2003 | Ben-Haim et al. |
| 2003/0093117 A1 | 5/2003 | Saadat |
| 2003/0208212 A1 | 11/2003 | Cigaina |
| 2004/0006351 A1 | 1/2004 | Gannoe et al. |
| 2004/0024386 A1 | 2/2004 | Deem et al. |
| 2004/0030347 A1 | 2/2004 | Gannoe et al. |
| 2004/0044353 A1 | 3/2004 | Gannoe |
| 2004/0044357 A1 | 3/2004 | Gannoe et al. |
| 2004/0054352 A1 | 3/2004 | Adams et al. |
| 2004/0059289 A1 | 3/2004 | Garza Alvarez |
| 2004/0068224 A1 | 4/2004 | Couvillon et al. |
| 2004/0092892 A1 | 5/2004 | Kagan et al. |
| 2004/0097986 A1 | 5/2004 | Adams |
| 2004/0098060 A1 | 5/2004 | Ternes |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0148034 A1 | 7/2004 | Kagan et al. |
| 2004/0186503 A1 | 9/2004 | DeLegge |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0260345 A1 | 12/2004 | Foerster |
| 2004/0267378 A1 | 12/2004 | Gazi et al. |
| 2005/0022827 A1 | 2/2005 | Woo et al. |
| 2005/0049718 A1 | 3/2005 | Dann et al. |
| 2005/0096638 A1 | 5/2005 | Starkebaum et al. |
| 2005/0159769 A1 | 7/2005 | Alverdy |
| 2005/0197687 A1 | 9/2005 | Molaei et al. |
| 2005/0203344 A1 | 9/2005 | Orban, III et al. |
| 2005/0216040 A1 | 9/2005 | Gertner et al. |
| 2005/0216042 A1 | 9/2005 | Gertner et al. |
| 2005/0222638 A1 | 10/2005 | Foley et al. |
| 2005/0228415 A1 | 10/2005 | Gertner |
| 2005/0261712 A1 | 11/2005 | Balbierz |
| 2005/0267405 A1 | 12/2005 | Shah |
| 2005/0267406 A1 | 12/2005 | Hassler, Jr. |
| 2005/0267533 A1 | 12/2005 | Gertner |
| 2005/0267595 A1 | 12/2005 | Chen et al. |
| 2005/0267596 A1 | 12/2005 | Chen et al. |
| 2005/0277960 A1 | 12/2005 | Hassler, Jr. et al. |
| 2005/0277974 A1 | 12/2005 | Hassler, Jr. et al. |
| 2006/0009789 A1 | 1/2006 | Gambale et al. |
| 2006/0020278 A1 | 1/2006 | Burnett et al. |
| 2006/0025789 A1 | 2/2006 | Laufer et al. |
| 2006/0025819 A1 | 2/2006 | Nobis et al. |
| 2006/0030884 A1 | 2/2006 | Yeung et al. |
| 2006/0058829 A1 | 3/2006 | Sampson |
| 2006/0089571 A1 | 4/2006 | Gertner |
| 2006/0089646 A1 | 4/2006 | Bonutti |
| 2006/0106288 A1 | 5/2006 | Roth et al. |
| 2006/0161186 A1 | 7/2006 | Hassler, Jr. et al. |
| 2006/0161256 A1 | 7/2006 | Ziegler et al. |
| 2006/0195139 A1 | 8/2006 | Gertner |
| 2006/0212053 A1 | 9/2006 | Gertner |
| 2006/0253131 A1 | 11/2006 | Wolniewicz |
| 2006/0264699 A1 | 11/2006 | Gertner |
| 2006/0265042 A1 | 11/2006 | Catanese, III et al. |
| 2006/0276871 A1 | 12/2006 | Lamson et al. |
| 2006/0282081 A1 | 12/2006 | Fanton et al. |
| 2007/0027358 A1 | 2/2007 | Gertner et al. |
| 2007/0049970 A1 | 3/2007 | Belef et al. |
| 2007/0060940 A1 | 3/2007 | Brazzini et al. |
| 2007/0073318 A1 | 3/2007 | Carter et al. |
| 2007/0073323 A1 | 3/2007 | Carter et al. |
| 2007/0088373 A1 | 4/2007 | Baker |
| 2007/0112363 A1 | 5/2007 | Adams |
| 2007/0112385 A1 | 5/2007 | Conlon |
| 2007/0129738 A1 | 6/2007 | Kraemer et al. |
| 2007/0167982 A1 | 7/2007 | Gertner et al. |
| 2007/0173869 A1 | 7/2007 | Gannoe et al. |
| 2007/0173888 A1 | 7/2007 | Gertner et al. |
| 2007/0179335 A1 | 8/2007 | Gertner et al. |
| 2007/0203517 A1 | 8/2007 | Williams et al. |
| 2007/0233170 A1 | 10/2007 | Gertner et al. |
| 2007/0235083 A1 | 10/2007 | Dlugos |
| 2007/0239284 A1 | 10/2007 | Skerven et al. |
| 2007/0250103 A1 | 10/2007 | Makower |
| 2007/0255308 A1 | 11/2007 | Williams et al. |
| 2007/0260259 A1 | 11/2007 | Fanton et al. |
| 2007/0270892 A1 | 11/2007 | Makower |
| 2007/0276293 A1 | 11/2007 | Gertner |
| 2007/0276432 A1 | 11/2007 | Stock |
| 2008/0009888 A1 | 1/2008 | Ewers et al. |
| 2008/0015501 A1 | 1/2008 | Gertner |
| 2008/0033488 A1 | 2/2008 | Catanese, III et al. |
| 2008/0039894 A1 | 2/2008 | Catanese, III et al. |
| 2008/0051823 A1 | 2/2008 | Makower et al. |
| 2008/0051824 A1 | 2/2008 | Gertner |
| 2008/0051850 A1 | 2/2008 | Sparks et al. |
| 2008/0058710 A1 | 3/2008 | Wilk |
| 2008/0071306 A1 | 3/2008 | Gertner |
| 2008/0082113 A1 | 4/2008 | Bishop et al. |
| 2008/0086082 A1 | 4/2008 | Brooks |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0109027 A1 | 5/2008 | Chen et al. |
| 2008/0147002 A1 | 6/2008 | Gertner |
| 2008/0161717 A1 | 7/2008 | Gertner |
| 2008/0167519 A1 | 7/2008 | Pascal-St-Germain |
| 2008/0167647 A1 | 7/2008 | Gertner |
| 2008/0167648 A1 | 7/2008 | Gertner |
| 2008/0172074 A1 | 7/2008 | Baker et al. |
| 2008/0172079 A1 | 7/2008 | Birk |
| 2008/0208240 A1 | 8/2008 | Paz |

FOREIGN PATENT DOCUMENTS

| | | |
|---|---|---|
| EP | 1 602 392 A1 | 7/2005 |
| EP | 1 591 140 A1 | 11/2005 |
| EP | 1 520 563 A1 | 4/2006 |
| EP | 1 547 642 B1 | 8/2007 |
| EP | 1 607 071 B1 | 8/2007 |
| EP | 1 670 361 B1 | 4/2008 |
| FR | 2 907 665 | 5/2008 |
| WO | WO 87/00034 | 1/1987 |
| WO | WO 99/25418 | 5/1999 |
| WO | WO 9925418 | 5/1999 |
| WO | WO 00/09049 | 2/2000 |
| WO | WO 00/18330 | 4/2000 |
| WO | WO 00/74573 A1 | 12/2000 |
| WO | WO 01/47435 | 7/2001 |
| WO | WO 02/35980 | 5/2002 |
| WO | WO0235980 | 5/2002 |
| WO | WO 02071951 | 9/2002 |
| WO | WO 03/055420 | 7/2003 |
| WO | WO 03095015 | 11/2003 |
| WO | WO 2004004542 | 1/2004 |
| WO | WO 2004014237 | 2/2004 |
| WO | WO 2004019765 | 3/2004 |
| WO | WO 2004021894 | 3/2004 |
| WO | WO 2004/037064 A2 | 5/2004 |
| WO | WO 2005007232 | 1/2005 |
| WO | WO 2005/009288 | 2/2005 |
| WO | WO 2005/018417 A2 | 3/2005 |
| WO | WO 2005/018417 A3 | 3/2005 |
| WO | WO 2005018417 | 3/2005 |

| | | |
|---|---|---|
| WO | WO 2005020802 | 3/2005 |
| WO | WO 2005/094447 A2 | 10/2005 |
| WO | WO 2005/105003 A1 | 11/2005 |
| WO | WO 2006/020370 A2 | 2/2006 |
| WO | WO 2006/049725 A2 | 5/2006 |
| WO | WO 2006063593 A2 | 6/2006 |
| WO | WO 2006/108203 | 10/2006 |
| WO | WO 2006127431 | 11/2006 |
| WO | WO2006134106 | 12/2006 |
| WO | WO 2006134106 A1 | 12/2006 |
| WO | WO 2007017880 A2 | 2/2007 |
| WO | WO 2007/067206 A2 | 6/2007 |
| WO | WO 2007064906 A2 | 6/2007 |
| WO | WO 2007/110866 A2 | 10/2007 |
| WO | WO 2008/006084 A2 | 1/2008 |
| WO | WO 2008013814 | 1/2008 |

OTHER PUBLICATIONS

Buchwald—Overview of Bariatric Surgery. Journal of the American College of Surgeons. pp. 367-375, Mar. 2002.
Sharp, et al., The 4-S Modification of the Roeder Knot: How to Tie It. pp. 1004-1006, vol. 90, No. 6, Dec. 1997.
Schauer, et al., New application for Endoscopy: the emerging field of endoluminal and transgastric bariatric surgery. 10 pgs., Apr. 24, 2006.
Buchwald et al., "Bariatric Surgery: A Systematic Review and Meta-analysis", JAMA 2004, vol. 292, No. 14, pp. 1724-1737.
Buchwald et al., "Evolution of Operative Procedures for the Management of Morbid Obesity 1950-2000", Obesity Surgery 2002, 12: 705-717.
Camerini et al., "Thirteen Years of Follow-up in Patients with Adjustable Silicone Gastric Banding for Obesity: Weight Loss and Constant Rate of Late Specific Complications" Obesity Surgery 2004, 14: 1343-1348.
Cope et al., "Percutaneous Transgastric Technique for Creating Gastroenteric Anastomoses in Swine", Journal of Vascular and Interventional Radiology, 2004, 15: 177-181.
Cummings et al., "Genetics and Pathophysiology of Human Obesity", An Annual Review of Medicine, 2003, 54:453-471.
Johnston et al., "The Magenstrasse and Mill Operation for Morbid Obesity", Obesity Surgery 2003, 13: 10-16.
Morino et al., "Laparoscopic Adjustable Silicone Gastric Banding Versus Vertical Banded Gastroplasty in Morbidly Obese Patients" Analysis Obesity Surgery vol. 238, No. 6, 2003, pp. 835-842.
Roman et al., "Intragastric Balloon of Non-Morbid Obesity: A Retrospective Evaluation of Tolerance and Efficacy", Obesity Surgery, 2004, 14:539-544.
Sallet et al., Brazillian Multicenter Study of the Intragastric Ballon; Obesity Surgery, 2004, 14, pp. 991-998.
Sjostrom et al., Lifestyle, Diabeters, and Cardiovascular Risk Factors 10 years after Bariatric Surgery, New England Journal of Medicine, 2004, 351, (6) 2683-2693.
Smith et al., "Modification of the Gastric Partitioning Operation for Morbid Obesity", Am. J. Surgery 142, Dec. 1981. pp. 725-730.
Smith et al., "Results and Complications of Gastric Partitioning: Four Years Follow-Up of 300 Morbidly Obese Patients", The American Journal of Surgery, 1983, (146) pp. 815-819.
Trumble et al., "Method for measuring long-term function of muscle-powered implants via radiotelemetry" J. Appl. Physiol. 2001, 90: pp. 1977-1985.
About the Vertical Sleeve Gastrectomy. Mar. 24, 2006, pp. 1-1. http://obesityhelp.com/forums/VSG/about.html.
Akira., JP63277063, Japanese and English Abstract, Nov. 15, 1988, pp. 1-4.
Abhyankar et al, Use of a tissue expander and a polyglactic acid (Vicryl) mesh to reduce radiation enteritis: case report and literature view, 21: pp. 755-757, Aug. 2005.
Buchwald, Overview of Bariatric Surgery, vol. 194, No. 3, Mar. 2002, pp. 367-375.
Burnett, et al., The Use of a Pelvic Displacement Prosthesis to Exclude the Small Intestine from the Radiation Field Following Radical Hysterectomy, 79, pp. 438-443, 2000. http://www.idealibrary.com.
Brolin, Robert E., Gastric Bypass. vol. 81, No. 5, Oct. 2001, pp. 1077-1095.
Cheng, Splenic Epidermoid Cyst, pp. 1-3, 1997.
Med-4840, Product Profile, Mar. 30, 2007, pp. 1-2.
DeMaria, Eric J., Laparoscopic Adjustable Silicone Gastric Banding. vol. 81, No. 5, Oct. 2001, pp. 1129-1143.
Deitel, Mervyn., Overview of Operations for Morbid Obesity. vol. 22, No. 9, Sep. 1998, pp. 913-918.
Doherty, Cornelius., Technique of Vertical Banded Gastroplasty. vol. 81, No. 5, Oct. 2001, pp. 1097-1111.
Foglia et al., Management of giant omphalocele with rapid creation of abdominal domain, 41, pp. 704-709, 2006.
Fried et al., Physical Principles of Available Adjustable Gastric Bands: How they Work. Obesity Surgery, 14, 2004, pp. 1118-1122.
Gertner MD, Stomach Restriction with an Extragastric Balloon, pp. 1, Abstract for 2007.
Geliebter et al; Extra-abdominal pressure alters food intake, intragastric pressure, and gastric emptying rate. 1986, pp. R549-R552.
Hoffman et al., Morbidity after Intraperitoneal Insertion of Saline-Filled Tissue Expanders for Small Bowel Exclusion from Radiotherapy Treatment Fields: A Prospective Four Year Experience with 34 Patients, pp. 473-483, No. 7, vol. 60, Jul. 1994.
Hainaux et al., Laparoscopic adjustable silicone gastric banding: radiological appearances of a new surgical treatment for morbid obesity. 1999, Abdom Imaging 24: 533-537.
Konturek et al., Neuro-Hormonal Control of Food Intake; Basic Mechanisms and Clinical Implications, 2005, 56, Supp 6, 5-25. www.jpp.krakow.pl.
Lam et al., Huge Splenic Epidermoid Cyst: A Case Report, 1997; 60:113-6.
Laparoscopic Duodenal Switch, Mar. 24, 2006, http://wo-pub2.med.cornell.edu/chi.bin/WebObjects/PublicA.woa/5/w . . . p. 1-1.
Lee et al., Laparoscopic Vertical Sleeve Gastrectomy: A Novel Bariatric Procedure-superior to Estabilished Operations? pp. 1-27. 90th Annual Clinical Congress, New Orleans, LA, Oct. 10, 2004.
Malassagne, et al., Intra-abdonimal Sengstaken-Blakemore tube Placement for acute venous outflow obstruction in reduced-size Liver, Nov. 1996, 83, pp. 1086.
Marceau, et al., Malabsorptive Obesity Surgery. vol. 81, Oct. 2001, No. 5, pp. 1113-1127.
Mera, et al., Use of the Breast Implant for Liver Graft Malposition. vol. 5, No. 6, Nov. 1999, pp. 534-535.
Obesity Surgery Including Laparoscopy and Allied Care. vol. 16, No. 1, Jan. 2006, pp. 1-2. www.obesitysurgey.com.
Pomerri et al., Adjustable Silicone Gastric Banding of Obesity., 1992, Gastrointest Radiol 17:207-210.
Schauer, et al., New applications for endoscopy: the emerging field of endoluminal and transgastric bariatric surgery, DOI:10.1007/s00464-006-9008-8, 2006.
The Sleeve Gastrectomy (or 2-Stage Procedure). 2006, pp. 1-2. http://surgicallyslim.com/sleeve.htm.
Walker, et al. Bladder Augmentation in Dogs Using the Tissue Capsule Formed Around a Perivesical tissue Expander, vol. 168, pp. 1534-1536, 2002.
Zwart et al., Gastric Motility: Comparison of Assessment with Real-Time MR Imaging or Barostat Experience1., 224: pp. 592-597, Aug. 2002.
Tucker, Diana, Medical Device Daily. vol. 10, No. 102, pp. 1-10, May 26, 2006.

* cited by examiner

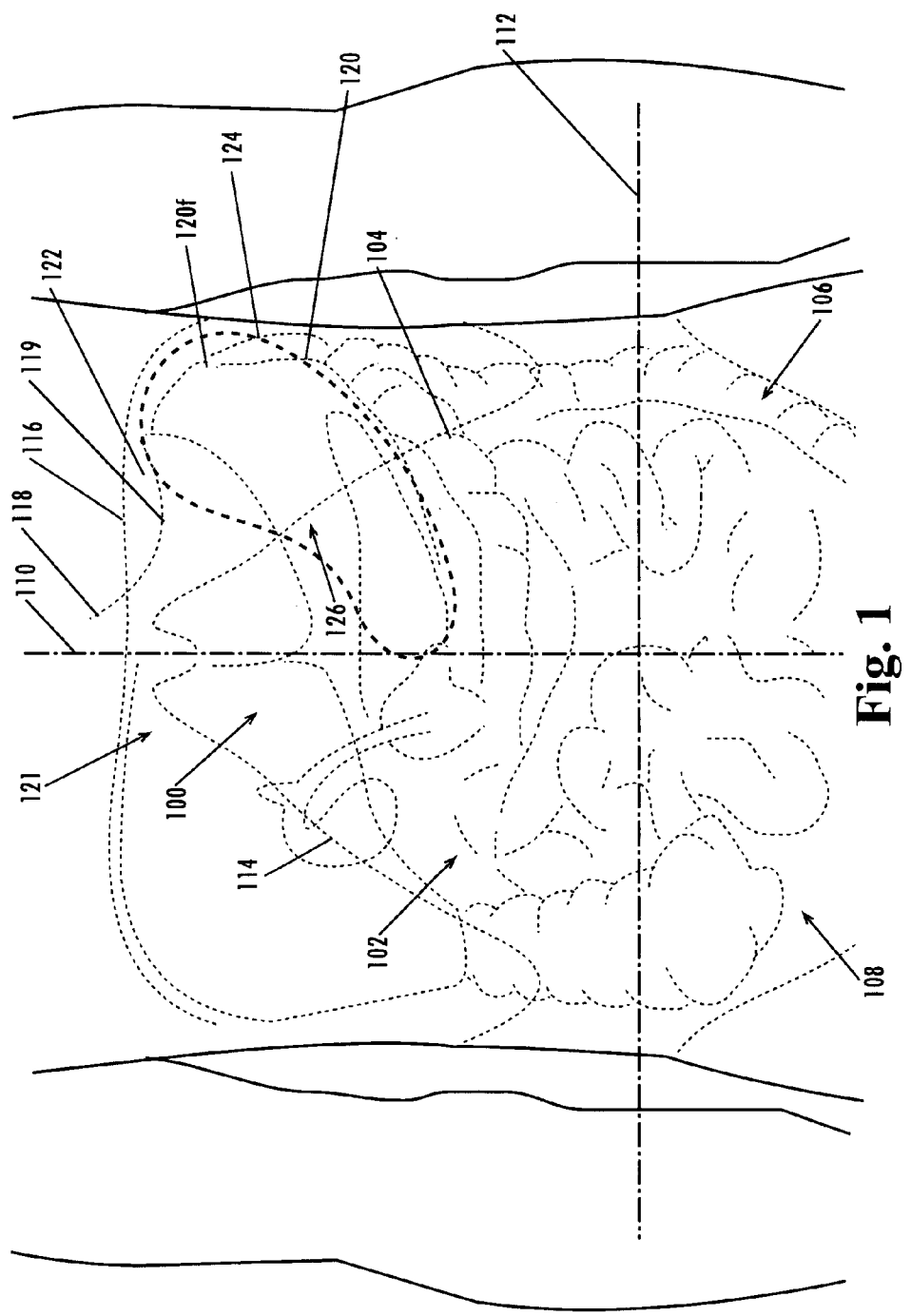

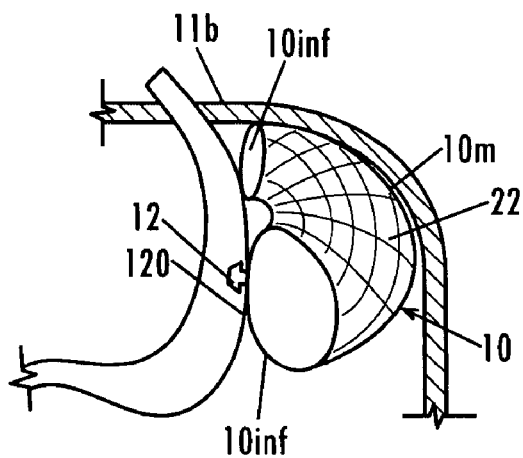
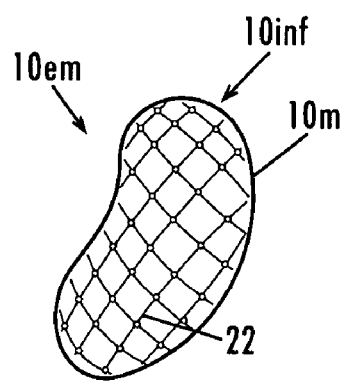
Fig. 11          Fig. 12
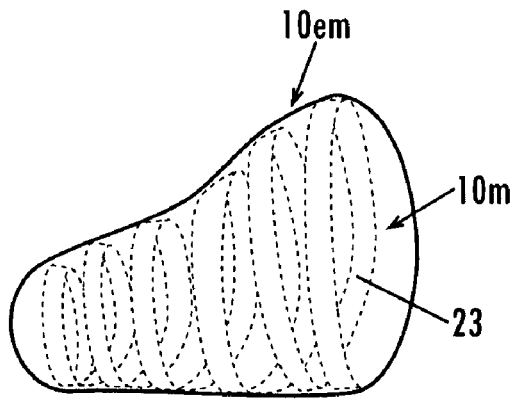
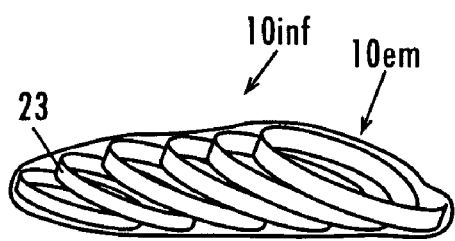
Fig. 13A          Fig. 13B
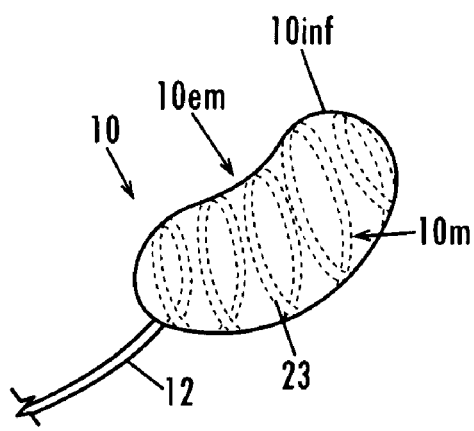
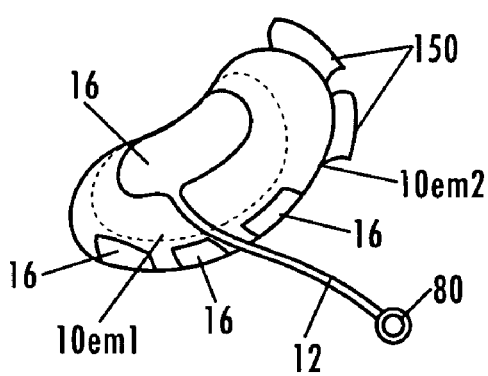
Fig. 13C          Fig. 14

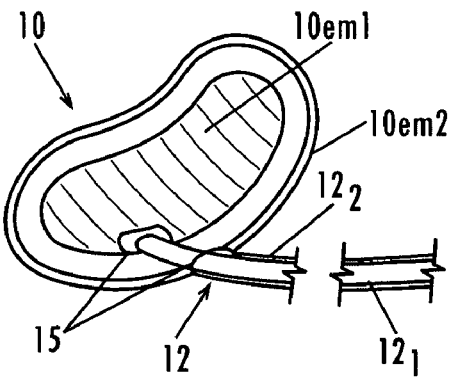
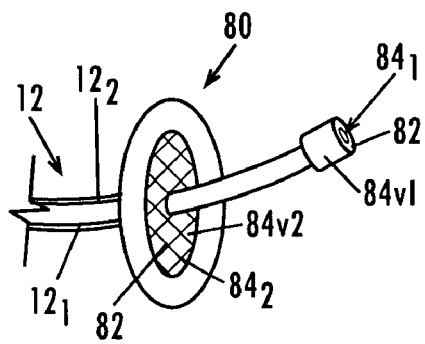
Fig. 15A  Fig. 15B
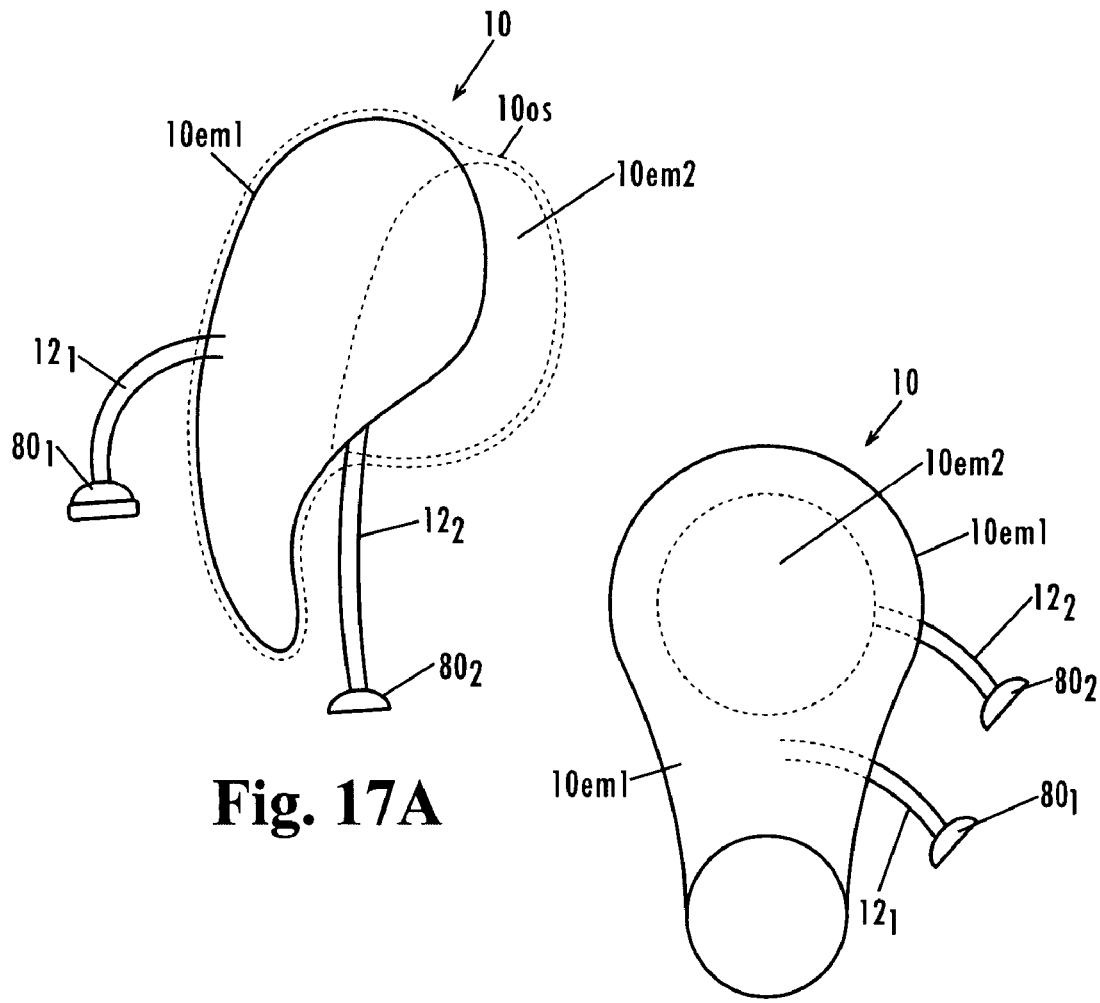
Fig. 17A  Fig. 17B

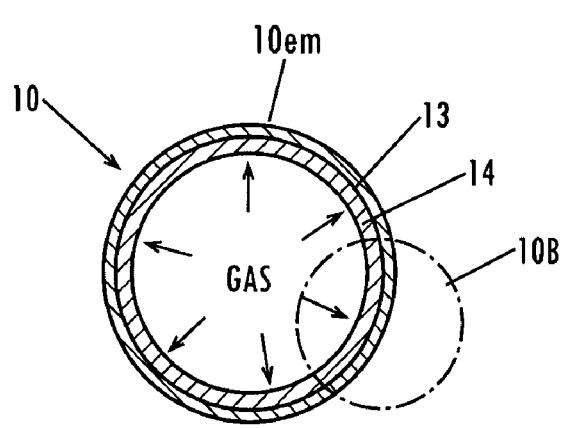
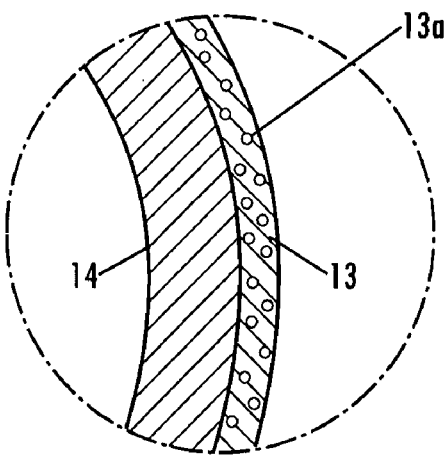
Fig. 20A  Fig. 20B
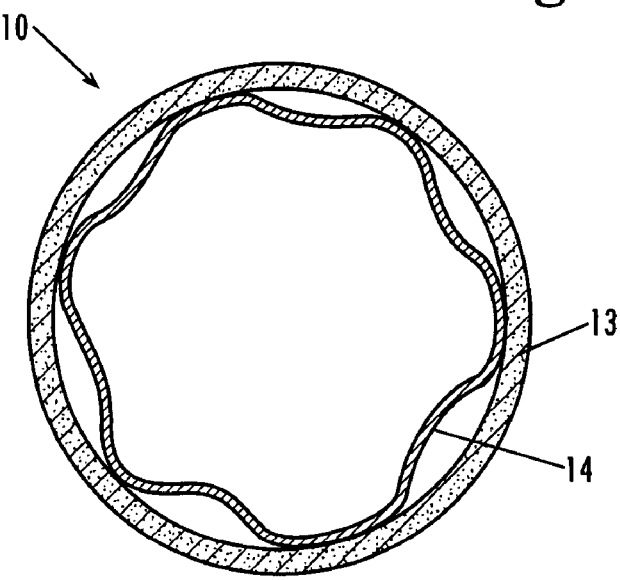
Fig. 21
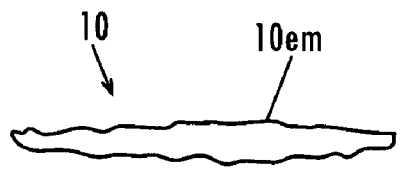 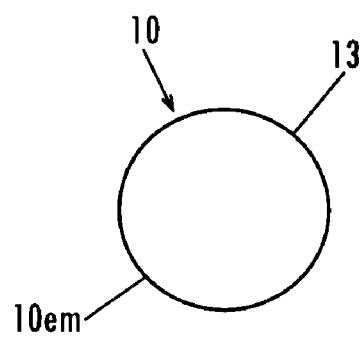
Fig. 22A  Fig. 22B

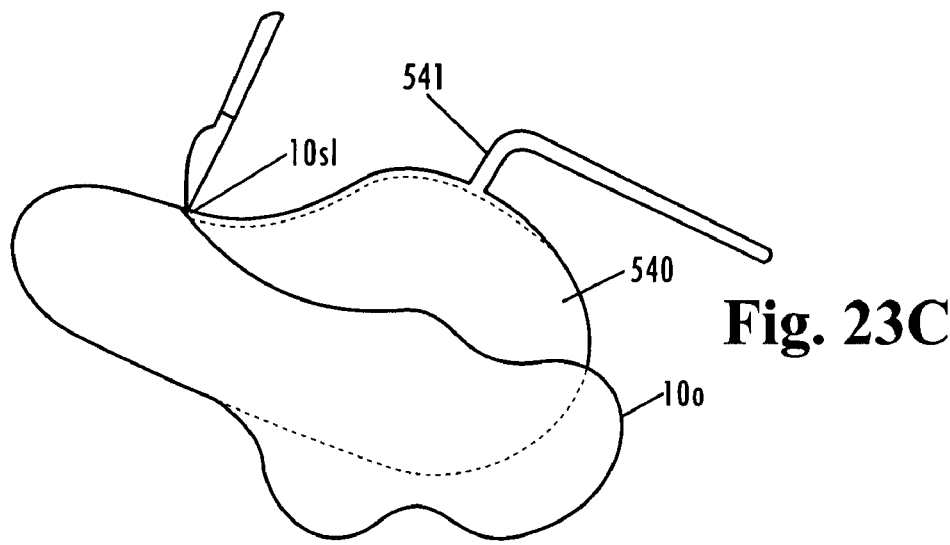
Fig. 23C
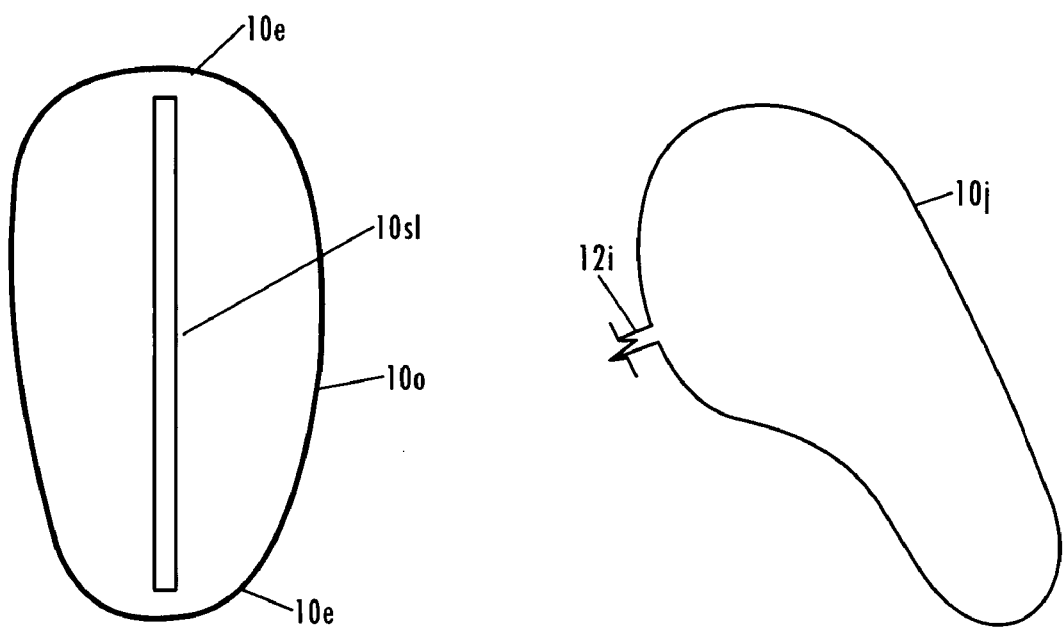
Fig. 23D
Fig. 23E
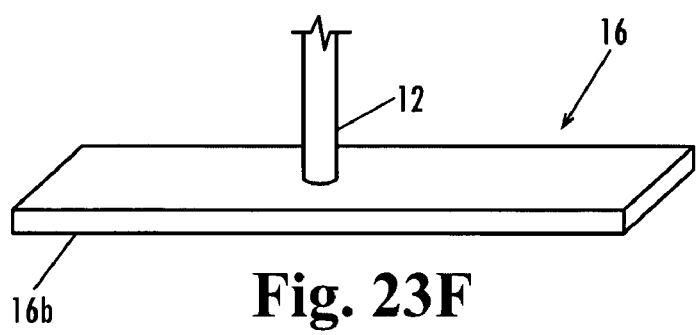
Fig. 23F

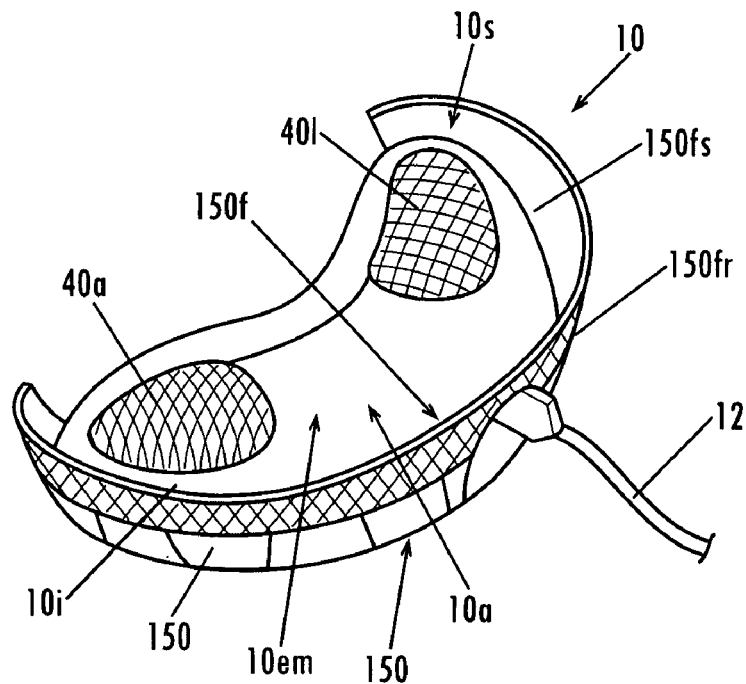
Fig. 30
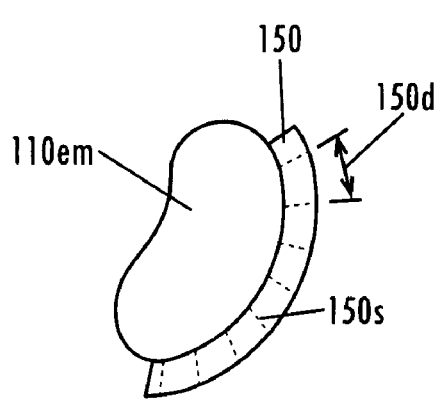 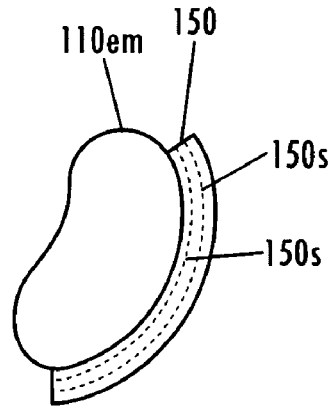
Fig. 31A   Fig. 31B
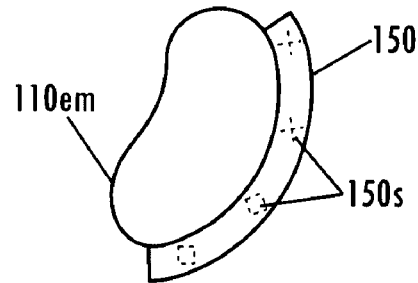
Fig. 31C

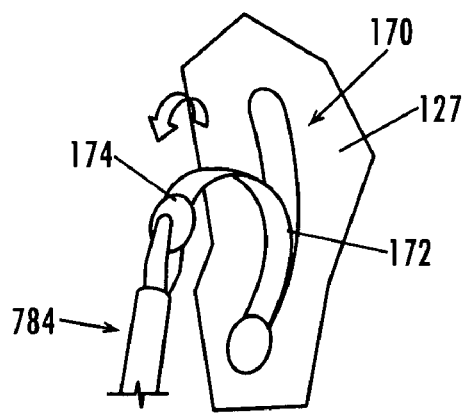
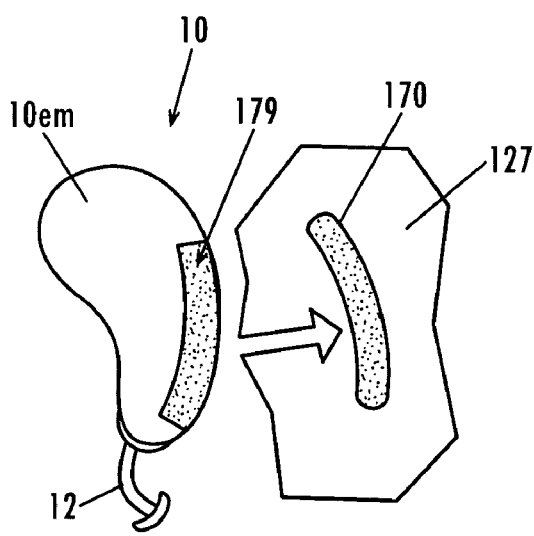
Fig. 33G                Fig. 33H
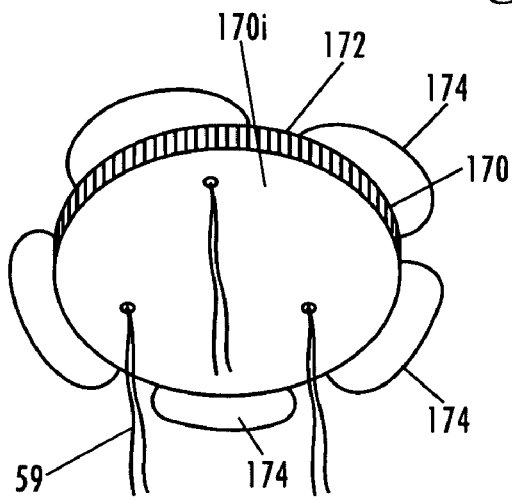
Fig. 33I
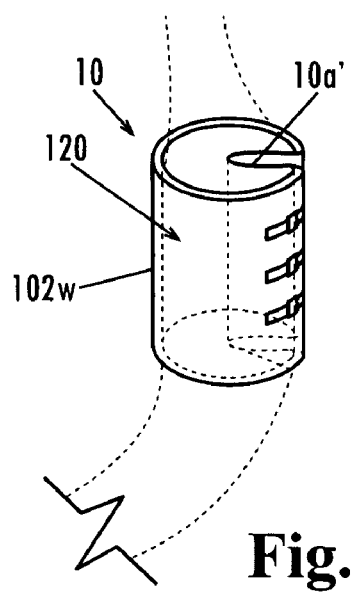
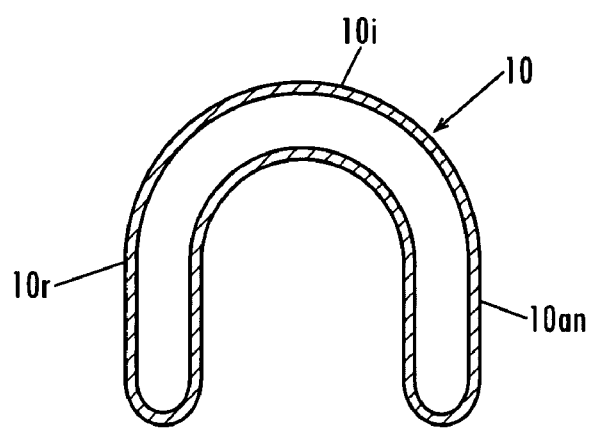
Fig. 34                Fig. 35

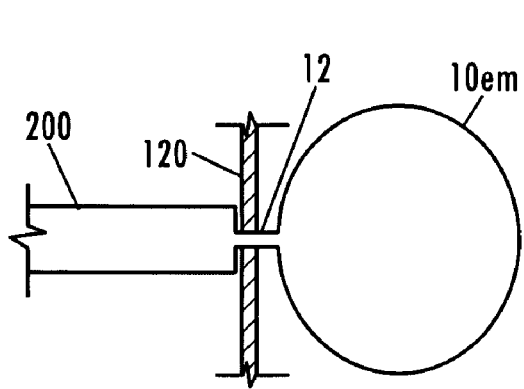
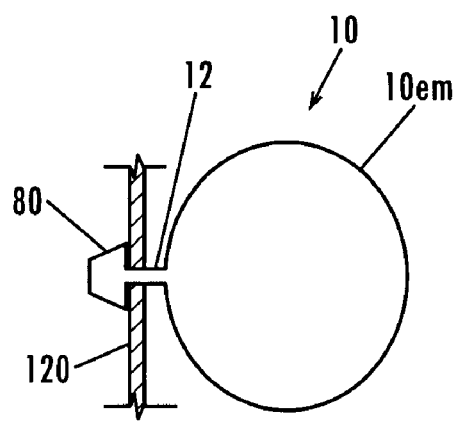
Fig. 39D  Fig. 39E
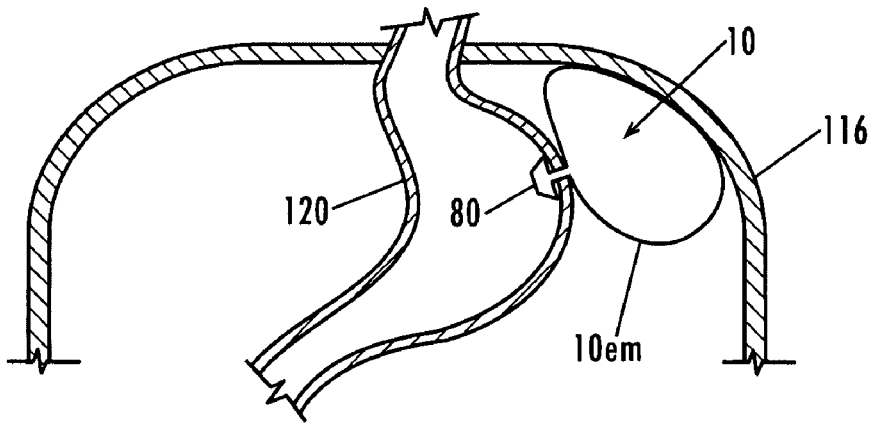
Fig. 39F
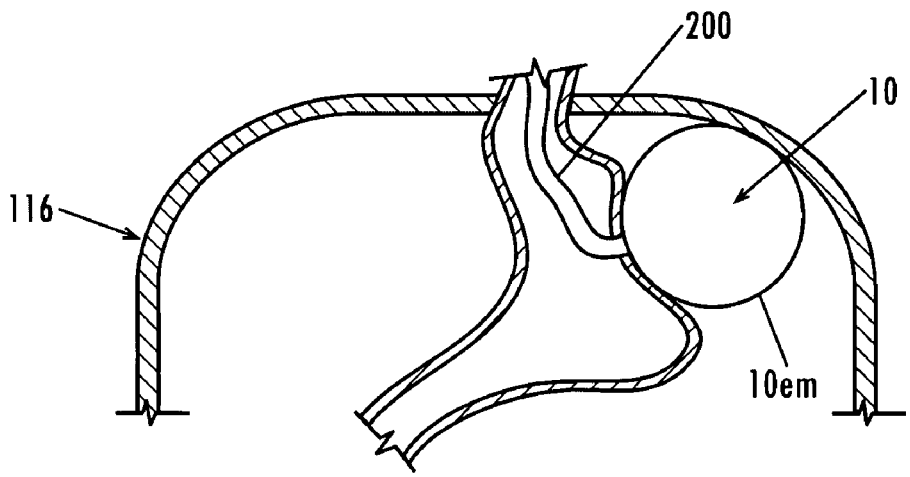
Fig. 39G

DEVICES AND METHODS FOR TREATMENT OF OBESITY

CROSS-REFERENCE

This application claims the benefit, under 35 U.S.C. §119 of U.S. Provisional Application No. 60/833,284, filed Jul. 24, 2006, titled "Devices and Methods for Treating Obesity", which application is hereby incorporated herein, in its entirety, by reference thereto, and to which we claim priority This application is a continuation-in-part application of co-pending application Ser. No. 11/716,986 filed Mar. 10, 2007 and a continuation-in-part application of application Ser. No. 11/716,985 filed Mar. 10, 2007, both of which applications are continuations-in-part of application Ser. No. 11/407,701, now U.S. Pat. No. 8,070,768, filed Apr. 19, 2006, which claims priority to Application Ser. Nos. 60/833,284 and 60/877,595. Application Ser. Nos. 11/716,986; 11/716,985 11/407,701 now U.S. Pat. No. 8,070,768, and 60/877,595 are each hereby incorporated herein, in their entireties, by reference thereto, and to which applications we claim priority under 35 USC. 120.

This application claims the benefit of U.S. Provisional Application No, 60/877,595, filed Dec. 28, 2006.

FIELD OF THE INVENTION

The present invention relates to treatment of obesity, more particularly to implantable devices and methods of implanting the devices to treat an obese patient.

BACKGROUND OF THE INVENTION

Obesity has become a major health concern, both nationally and internationally. The National Center for Health Statistics (NCHS) estimates that over 120 million Americans are overweight, including about 56% of the adult population. Of these, about 52 million are considered obese, as measured by a body mass index (BMI) of 30% or greater. In Europe, an estimated 77 million people are obese, as measured by the same standard. This problem is not limited to western nations, as many developing countries are reported to have obesity rates over 75% of the adult population.

Co-morbidities that are associated with obesity include, but are not limited to type II Diabetes, high blood pressure, sleep apnea, stroke and arthritis, the symptoms of which often tend to be lessened or alleviated upon loss of weight by a person so affected.

In the U.S., options for treatment of obesity are currently quite limited. Current treatment methodologies typically rely upon surgically introducing a "malabsorptive" environment in the gastro-intestinal tract, a restrictive environment, or a combination of these. One available treatment method is gastric bypass surgery and another is referred to as gastric banding (one of these techniques if referred to as the LAPBAND™ procedure). These procedures are limited to only those patients with a BMI over 40 (or over 35, with co-morbidities present).

Gastric bypass procedures incur a great deal of morbidity and create a malabsorptive state in the patient by bypassing a large portion of the intestines. Serious side effects, such as liver failure have been associated with this procedure, as well as chronic diarrhea. Another surgical procedure that has a high degree of morbidity associated with it is known as the "Gastric Bypass Roux-en-Y" procedure. This procedure reduces the capacity of the stomach by creating a smaller stomach pouch. The small space holds only about one ounce of fluid. A tiny stomach outlet is also surgically created to slow the speed at which food leaves the stomach. Staples are used to create a small (15 to 20 cc) stomach pouch, with the rest of the stomach being stapled completely shut and divided from the stomach pouch. The small intestine is divided just beyond the duodenum, brought up, and connected to the newly formed stomach pouch. In addition to the considerable morbidity associated with this procedure, other disadvantages include "dumping syndrome", where stomach contents are literally "dumped" rapidly into the small intestine which may lead to nausea, weakness, sweating, faintness, and diarrhea; hernias resulting from the surgery; gallstones; leakage of the connection between the pouch and the intestine; stretching of the pouch that was formed; nutritional deficiencies; and possible dehiscence of the staples.

The LAPBAND™ is a band that, when placed, encircles the fundus-cardia junction and is inflatable to constrict the same. It does not reduce the volume of the stomach, but rather restricts passage of food into the stomach, the theory being that the patient will feel satiety with a much less volume of food than previously. Although the LAPBAND™ procedure is less invasive than a gastric bypass procedure, it also typically achieves less weight loss. Further, it is not a simple procedure and requires a substantial amount of training by a surgeon to become proficient in performing the procedure. Also, a substantial amount of dissecting and suturing is required because the pathway by which the band is introduced is not an existing pathway, and must be established by dissection. Great care is required to avoid blood vessels and nerves that may be in the intended pathway to be created by the dissection. After placing the band around the fundus-cardia junction, the ends of the band must be connected together and then it must be cinched down into place. Additionally, complications such as erosion at the fundus-cardia junction, slippage of the band from its intended location, nausea/vomiting, gastroesophageal reflux, dysphagia and lack of effectiveness in causing weight loss have been reported.

Intra-gastric balloons have also been placed, in an attempt to fill a portion of the volume in the stomach, with the theory being that it will then require less food than previously, to give the patient a sensation of fullness or satiety. This procedure involves delivery of a balloon (typically, trans-orally) to the interior of the stomach and inflation of the balloon to take up a portion of the volume inside the stomach. However, intra-gastric balloons may also lead to complications such as obstruction, vomiting and/or mucosal erosion of the inner lining of the stomach. The balloon can break down over extended exposure to the stomach's acids, and in some cases, after breaking down, the balloon translated through the intestines and caused a bowel obstruction.

Gastrointestinal sleeves have been implanted to line the stomach and/or a portion of the small intestines to reduce the absorptive capabilities of the small intestine and/or to reduce the volume in the stomach, by reducing the available volume to the tubular structure of the graft running therethrough. Although weight loss may be effective while these types of devices are properly functioning, there are complications with anchoring the device within the stomach/GI tract, as the stomach and GI tract function to break down things that enter into them and to move/transport them through. Accordingly, the integrity of the anchoring of the device, as well as the device itself may be compromised over time by the acids and actions of the stomach and GI tract.

A sleeve gastrectomy is an operation in which the left side of the stomach is surgically removed. This results in a much reduced stomach which is substantially tubular and may take on the shape of a banana. This procedure is associated with a high degree of morbidity, as a large portion of the stomach is surgically removed. Additionally, there are risks of complications such as dehiscence of the staple line where the staples are installed to close the surgical incisions where the portion of the stomach was removed. Further, the procedure is not reversible.

In the laparoscopic duodenal switch, the size of the stomach is reduced in similar manner to that performed in a sleeve gastrectomy. Additionally, approximately half of the small intestine is bypassed and the stomach is reconnected to the shortened small intestine. This procedure suffers from the same complications as the sleeve gastrectomy, and even greater morbidity is associated with this procedure due to the additional intestinal bypass that needs to be performed. Still further, complications associated with malabsorption may also present themselves.

An inflatable gastric device is disclosed in U.S. Pat. No. 4,246,893, in which a balloon is inserted anteriorly of the stomach and posteriorly of the left lobe of the liver. The balloon is then inflated to compress the stomach so that it fills with less food that would ordinarily be possible. Not only does this device compress the stomach, but it also compresses the liver, as seen in FIG. 5 of the patent, which may cause complications with the liver function. Additionally, the balloon is simply placed into this location, and there is no assurance that it will not migrate and lose its effectiveness in compressing the stomach to the degree intended. Still further, the balloon is of a simple spherical design, and, as such, extends pressure outwardly in all directions, 360 degrees in all planes. Accordingly, the liver is compressed just as much as the stomach is. Also, the compression forces against the stomach are not ideal, as the spherical balloon conformation does not match the conformation of the expanding stomach. The stomach is not spherical when expanded, or concave with a constant radius of curvature, but expands into a designated space that allows the fundus to expand preferentially more than other parts of the stomach.

Brazzini et al. in WO2005/18417 discloses at least two or more expandable devices used to treat obesity, in which the devices are inserted through the abdominal wall and anchored subcutaneously or to the stomach wall to exert pressure against the external surface of the stomach wall.

U.S. Patent Publication No. 2005/0261712 to Balbierz et al. describes capturing a device against the outer surface of the stomach wall to form a restriction that appears to function similarly to the restriction imposed by the LAPBAND™. The anchoring of the devices disclosed relies upon placement of features against the internal wall of the stomach to form an interlock with the device which is placed against the external wall of the stomach.

U.S. Patent Publication No. 2005/0267533 to Gertner discloses devices for treatment of obesity that use one or more anchoring mechanisms that are passed through the wall of the stomach to establish an anchor. The stomach is reduced in size by passing the devices through the stomach wall on opposite sides of the stomach and compressing the walls together to eliminate a portion of the interior space within the stomach. Gertner also discloses an embodiment in which an extra-gastric balloon is placed anteriorly of the stomach and attached to the abdominal wall using one of the anchoring mechanisms described.

U.S. Pat. No. 6,981,978 to Gannoe discloses devices for reducing the internal cavity of the stomach to a much smaller volume, which may be used to carry out a bypass procedure. Stapling is employed to isolate the smaller volume in the stomach, and thus the same potential disadvantages are present as with other stapling procedures described herein.

U.S. Pat. No. 6,186,149 to Pacella et al. describes an occluder device that can be used as a dietary control device (see FIG. 8C). The occluder device is placed against the wall of the stomach and inflated to press inwardly on the stomach wall. A frame is wrapped around the stomach wall and is inflated to press against the stomach wall. However, there is no disclosure of how the frame might be adjusted to maintain a position relative to the stomach wall as the size of the stomach varies.

Gastric reduction techniques have been attempted, such as by inserting instruments trans-orally and reducing the volume of the stomach by stapling portions of it together. However, this technique is prone to failure due to the staples pulling through the tissues (i.e., dehiscence) that they are meant to bind.

Techniques referred to as gastric pacing endeavor to use electrical stimulation to simulate the normal feedback mechanisms of a patient that signal the brain that the patient is full, or satiated. While these techniques are less invasive than some of the other existing treatments, statistics to date have shown that the amount of weight lost by using such techniques is less than satisfactory.

Currently marketed drugs for weight loss, such as XENICAL®, MERIDIA® and Phen fen have largely failed, due to unacceptable side effects and complications, and sometimes to an ineffective amount of weight loss. Other drugs that are on the horizon include ACCOMPLIA® and SYMLIN®, but these are, as yet, unproven.

The risk and invasiveness factors of currently available surgeries are often too great for a patient to accept to undergo surgical treatment for his/her obesity. Accordingly, there is a need for less invasive, yet effective surgical treatment procedures for morbidly obese patients (patients having a BMI of 35 or greater). Also, since the current surgical procedures are currently indicated only for those patients having a BMI of 40 or greater, or 35 or greater when co-morbidities are present, it would be desirable to provide a surgical procedure that would be available for slightly less obese patients, e.g., patients having a BMI of 30 to 35 who are not indicated for the currently available surgical procedures. It would further be desirable to provide a surgical procedure that would be indicated for obese patients having a BMI in the range of 30-35, as well as for more obese patients.

SUMMARY OF THE INVENTION

The present invention provides devices and methods for treatment of obesity, as well as instruments and tools used in placing, adjusting and maintaining devices for treatment of obesity. Various embodiments of devices that are implanted extra-gastrically are provided. Various embodiments of devices that are implanted intra-gastrically are provided. Methods include laparoscopic, percutaneous and/or trans-oral methods. Alternatively, devices described can generally also be implanted by open surgical procedures.

In at least one embodiment, a method of treating obesity in a patient is provided to include: passing an elongated, maneuverable implement trans-orally through the mouth of the patient, the esophagus of the patient, and into the cavity of the stomach of the patient, wherein a proximal end portion of the implement extends out of the mouth of the patient when a distal end of the implement is located in the stomach cavity; forming an opening through the wall of the stomach; passing a device, in a contracted configuration, through the mouth, esophagus, into the stomach and through the opening through the wall of the stomach, thereby delivering the device to an extra-gastric location in the abdominal cavity; expanding the device; closing the opening through the wall of the stomach; and removing any implements or tools remaining in the patient.

In at least one embodiment, a method of treating obesity in a patient includes: passing a flexible tubing through the mouth of the patient, the esophagus of the patient, and into the cavity of the stomach of the patient, wherein a proximal end portion of the tubing extends out of the mouth of the patient when a distal end of the tubing is located in the stomach cavity; engaging a location on the inner surface of the stomach wall by applying suction through one or more suction lumens extending through a distal end portion of the tubing; extending a distal end portion of a flexible endoscope having been inserted through a working channel in the tubing, so that a distal tip of the flexible endoscope pierces through the stomach wall and enters the abdominal cavity outside of the stomach wall; removing the flexible endoscope from the patient while maintaining suction engagement of the tubing to the stomach wall; inserting a guidewire through the tubing, so that a distal end portion of the guidewire extends through the stomach opening and into the abdominal cavity and a proximal end portion of the guidewire extends proximally out of the patient and out of the tubing; removing the tubing from the patient while maintaining the guidewire in position; delivering an anchor pad deployment assembly over the guidewire, through the mouth, esophagus and stomach and through the opening in the stomach wall, so that at least an anchor pad or strip and a distal tip of a flexible endoscope contained in the anchor pad deployment assembly extend into the abdominal cavity; deploying the anchor pad or strip and attaching the anchor pad or strip to an internal abdominal structure other than the stomach; delivering a device, in a contracted configuration, over the guidewire through the mouth, esophagus, into the stomach and through the opening through the wall of the stomach, thereby delivering the device to an extra-gastric location in the abdominal cavity; attaching an anchoring pad or strip fixed to a portion of the device to the anchor pad or strip; and closing the opening through the wall of the stomach.

In at least one embodiment, a method of treating obesity in a patient includes: making an opening through a wall of the stomach of the patient; passing an expandable device, while in a contracted configuration, through the opening from a location within the cavity in the stomach to a location external of the stomach wall, without substantially deforming the stomach wall; expanding the expandable device; and anchoring the expandable device against an inner surface of the stomach wall, opposite a location of the expandable device adjacent an outer surface of the stomach wall.

In at least one embodiment, a method of treating obesity in a patient includes: passing an intra-gastric device in a compressed configuration trans-orally into the cavity inside the stomach of the patient; and expanding the intra-gastric device into an expanded configuration that forces the walls of the stomach outwardly to a stretched configuration.

In at least one embodiment, a method of treating obesity in a patient includes: forming a pocket between adjacent layers of a wall of the stomach in a location where reduction in volume of the cavity within the stomach is desired; and implanting a space occupying device in the pocket, wherein the space occupying device protrudes inwardly to deform the inner surface of the wall of the stomach into the cavity of the stomach, thereby reducing the volume of the cavity.

In at least one embodiment, a method of treating obesity in a patient includes: passing an elongated, maneuverable implement trans-orally through the mouth of the patient and into the cavity of the stomach of the patient, wherein a proximal end portion of the implement extends out of the mouth of the patient when a distal end of the implement is located in the stomach cavity; attaching the distal end of the implement to an inner surface of the stomach wall at a location where a deformation is desired to be made; retracting the implement to pull the wall of the stomach inwardly, wherein portions of the wall fold inwardly upon themselves as the wall is drawn inwardly; and fixing the folds of the wall together, to maintain the deformation, wherein external surfaces of the folds lie adjacent one another with no intervening structure.

In at least one embodiment, a method of treating obesity in a patient includes: wrapping a device around the outer layer of the stomach wall, wherein the device includes a main body member that surrounds the stomach to form an elongated enclosure when wrapped around the stomach, the device further including an elongated protrusion that extends inwardly into an opening formed for receiving the stomach within the device; and fixing the device relative to the stomach in a configuration where the protrusion deforms a portion of the stomach inwardly to reduce a lumen that extends within the stomach cavity.

In at least one embodiment, a method of treating obesity in a patient includes: pushing on the outer wall surface of the stomach with an instrument to deform the stomach wall inwardly, so that portion of the outer surface of the stomach wall fold inwardly upon one another; fixing the outer wall portions together to maintain an orientation wherein the folded wall portions face toward one another; expanding an expandable member mounted on a distal end portion of the instrument to expand against the folded wall portions; and removing the instrument, while leaving the expanded expandable member in place.

In at least one embodiment, an intra-gastric device for treatment of obesity is provided, including: an expandable member configured to assume a contracted configuration as well as an expanded configuration, wherein the contracted configuration reduces a cross-sectional area of the device to a cross sectional area suitable for passing the device trans-orally into a stomach cavity of a patient, and when in the expanded configuration, the device expands against the inner wall of the stomach with sufficient force (e.g. at least about 5 mm Hg, typically about 5 to about 7 mm Hg, or in the range of about 5.1 to about 6.5 mm Hg, or about 5.4 to about 5.9 mm Hg) to stretch the stomach wall to induce signals by the stomach wall indicating satiety, and wherein, when in the expanded configuration the device is thin walled and maintains the stomach cavity open to receive food.

In at least one embodiment, a device for treatment of obesity includes: a main body portion configured and dimensioned to be wrapped around the outer layer of the stomach wall, wherein the main body member surrounds the stomach to form an elongated enclosure when wrapped around the stomach; an elongated protrusion that extends inwardly into an opening formed for receiving the stomach within the device when the device is wrapped around the stomach; and an anchor configured to fix the device to the stomach with the elongated protrusion deforming the stomach inwardly, without piercing through a wall of the stomach.

In at least one embodiment, a device for treatment of obesity includes: an expandable main body member configured and dimensioned to be positioned adjacent and external of a portion of a stomach of a patient, without deforming the stomach cavity when the stomach cavity contains substantially no food; an adjustment member having a port that is accessible by an instrument to effect expansion or contraction of the main body, the adjustment member configured to be anchored against an internal surface of the stomach wall; and a conduit connecting the main body with the adjustment member, and having a length dimensioned to maintain the adjustment member in contact with the internal wall surface of the stomach, and the main body member in contact with an external wall surface of the stomach.

In at least one embodiment, a device for treatment of obesity includes: an expandable main body member configured and dimensioned to be positioned adjacent and external of a portion of a stomach of a patient; and an adjustment member integrated in the expandable main body member and having a port that is accessible by an instrument to effect expansion or contraction of the main body.

In at least one embodiment, a device for treatment of obesity includes: an expandable main body member configured and dimensioned to be positioned adjacent and external of a portion of a stomach of a patient; an adjustment member having a port that is accessible by an instrument to effect expansion or contraction of the main body, the adjustment member configured to be anchored against an internal surface of the stomach wall; and a conduit connecting the main body with the adjustment member, and having a length dimensioned to maintain the adjustment member in contact with the internal wall surface of the stomach, and the main body member in contact with an external wall surface of the stomach.

In at least one embodiment, a device for treatment of obesity is provided, including: a first expandable member formed of a compliant material and configured to be elastically expandable and dimensioned to be positioned adjacent and external of a portion of a stomach of a patient; and a second expandable member formed of a noncompliant or semi-compliant material and configured to be expanded to a relatively fixed, predetermined volume.

In at least one embodiment, a device for treatment of obesity includes: an expandable main body member configured and dimensioned to be positioned adjacent and external of a portion of a stomach of a patient; an anchor strip or pad configured to be attached to an internal body structure other than the stomach of a patient; and an anchoring strip or pad fixed to the main body member and configured to attach to the anchor strip or pad.

A flexible, expandable sheath for trans-oral delivery of a device into an abdominal cavity of a patient is provided, including: an elongated, flexible tube having a length sufficient to be inserted through the mouth of a patient, through the esophagus of the patient, into the stomach of the patient and through an opening formed through the wall of the stomach such that a distal end portion of the tube extends out of the stomach an into the abdominal cavity, and a proximal end portion at the same time extends proximally out of the mouth of the patient; and at least one radially extensible anchor on a distal end portion of the tube.

A system for intra-gastric delivery of a device into the stomach of a patient, through the stomach wall of the patient, and implantation of the device extra-gastrically, is provided, including: a flexible elongated instrument having a distal end portion including a distal end and a proximal end portion including a proximal end, the instrument configured to be inserted through the mouth of the patient, the esophagus and into the stomach, the instrument having sufficient length such that when the distal end is passed through a wall of the stomach and positioned externally of the stomach wall in the abdominal cavity, the proximal end extends proximally out of the mount of the patient. The system further includes a device configured for extra-gastric implantation in the abdominal cavity, the device, in a compact configuration being dimensioned to be passed along the elongated instrument through the mouth of the patient, esophagus and stomach and through an opening in the stomach wall that the distal end portion of the instrument extends through, and the device being expandable extra-gastrically to an expanded configuration that displaces a volume greater than a volume displaced by the device when in the compact configuration. An anchor is configured to fix the device to an intra-abdominal structure other than the stomach.

These and other features of the invention will become apparent to those persons skilled in the art upon reading the details of the devices, methods, instruments and tools as more fully described below.

BRIEF DESCRIPTION OF THE DRAWINGS

FIG. 1 illustrates the anatomy of the abdominal cavity and its contents, and surrounding features.

FIG. 11 illustrates a compound or hybrid expandable device having been positioned between the diaphragm and stomach and expanded against the stomach to deform the stomach wall inwardly.

FIG. 12 illustrates another example of a hybrid expandable member.

FIGS. 13A-13C illustrate another embodiment of a hybrid expandable member.

FIG. 14 illustrates another example of a device. In this example, an inner expandable member is at least partially surrounded by an outer expandable member.

FIG. 15A illustrates a device having an internal, relatively gas-impermeable expandable member and an external expandable member filled at least in part with liquid.

FIG. 15B illustrates an adjustment member configured for delivery of gas to the first expandable member and liquid to the second expandable member of the device of FIG. 15A.

FIGS. 17A-17B show views of another embodiment of a device.

FIG. 20A illustrates an inflatable member having an inner liner that is less porous that the outer membrane of the device.

FIG. 20B is a magnified view of the encircled portion 10B of FIG. 20A.

FIG. 21 illustrates a device wherein the inner liner is separate from the outer layer.

FIGS. 22A-22B illustrate another approach to reducing or minimizing the seepage rate through an inflatable member.

FIGS. 23A-23H illustrate one approach to fabricating a dual layer inflatable member for a device described herein.

FIG. 30 illustrates device 10 using a combination of attachment/anchoring features.

FIGS. 31A-31C illustrate various stapling patterns that may be employed for stapling an attachment flange or attachment tabs to one or more internal body structures for anchoring device/expandable member thereto.

FIG. 33G illustrates removal of the protective strip from engagement with the anchor strip.

FIG. 33H illustrates anchoring strip having been fixed to a surface of an expandable member of a device in a location to be placed over and attach to the attachment feature of the anchor strip, so as to properly place and orient the device as intended.

FIG. 33I illustrates an anchor pad and protective pad that are substantially circular.

FIG. 34 illustrates the device shown in FIG. 3N having been wrapped around and installed on the stomach.

FIG. 35 illustrates a device being substantially U-shaped in cross-section.

FIGS. 39A-39F illustrate steps that can be carried out in a method of implanting an extra-gastric device according to the present invention.

FIG. 39G illustrates an alternative to the step illustrated in FIG. 39F.

DETAILED DESCRIPTION OF THE INVENTION

Figure 1A:
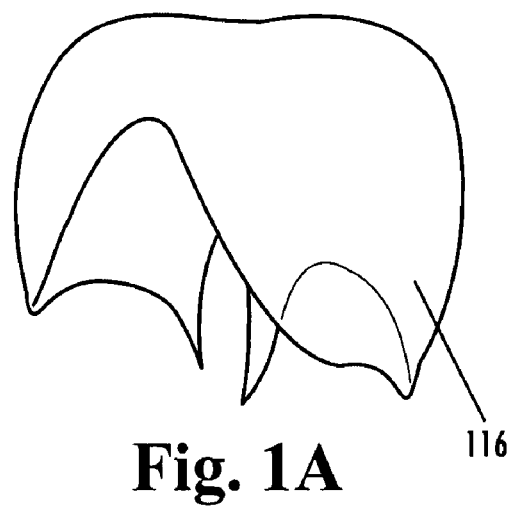
FIG. 1A is an illustration of a diaphragm in an isolated view, illustrating the conformation of the diaphragm as it exists in the body.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the an to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an expandable member" includes a plurality of such expandable members and reference to "the incision" includes reference to one or more incisions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

A "compliant" material refers to a material that is stretchable or expandable. This expansibility allows the material to increase in dimension substantially more than a noncompliant or semi-compliant material, prior to failure. For example, when formed as a balloon structure, a compliant material comprises an expansibility property of being able to increase its radius, beyond its formed radius, under pressure applied into the balloon, by one hundred percent or more, without rupturing.

A "noncompliant" material refers to a material that, when formed as a balloon structure, can increase its radius beyond its formed radius, under pressure applied into the balloon, only up to about ten percent or less prior to rupturing.

A "semi-compliant" material refers to a material that, when formed as a balloon structure, can increase its radius beyond its formed radius, under pressure applied into the balloon, by an amount between about ten percent and about one hundred percent, prior to rupturing.

The "wall" of the stomach refers to all of the layers that make up the stomach wall, including the mucosa, submucosa, muscular layers and serosa. A "layer", "layer of the stomach wall" or "stomach wall layer" refers to a mucosal layer, submucosal layer, muscular layer or serosal layer.

A "proximal" end of an instrument is the end that is nearer the surgeon when the surgeon is using the instrument for its intended surgical application.

A "distal" end of an instrument is the end that is further from the surgeon when the surgeon is using the instrument for its intended surgical application.

An "internal body structure" when referred to as a structure to which a device is to be anchored, refers to a structure internal to the skin of a patient, and which can be within the abdominal cavity of the patient, or just outside of it, such as including the outer surface of a wall that partially defines the abdominal cavity.

Abdominal Cavity Anatomy

Figure 1B:
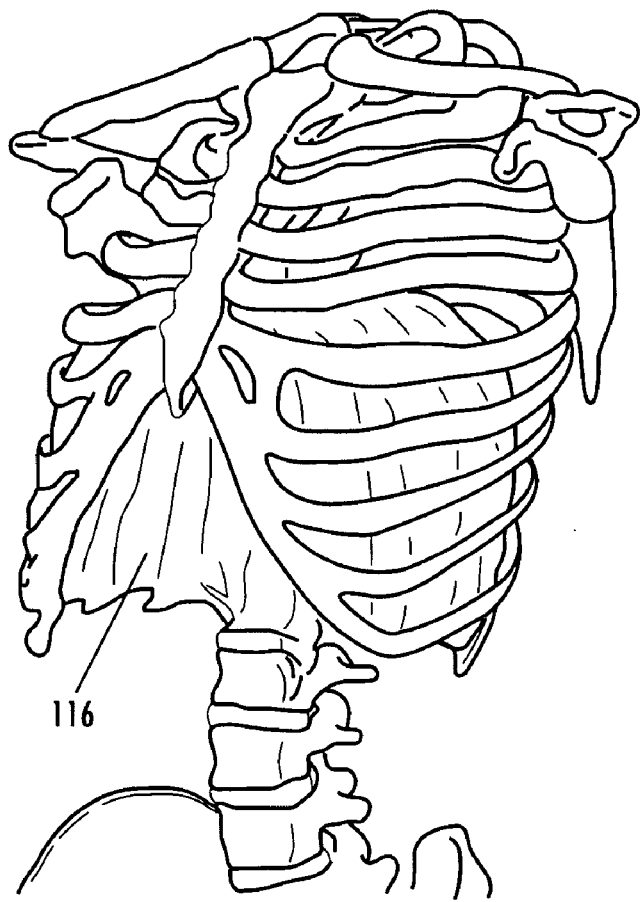
FIG. 1B illustrates the diaphragm in position relative to the rib cage.

FIG. 1 illustrates the anatomy of the abdominal cavity and its contents, and surrounding features. The abdominal cavity 100 is shown divided among four quadrants, the upper right quadrant 102, upper left quadrant 104, lower left quadrant 106 and lower right quadrant 108, as divided by the median axis 110 and transverse axis 112. The lower edge of the ribcage is illustrated by the dotted line 114 and the diaphragm is shown at 116. As seen in FIGS. 1A and 1B, the diaphragm 116 is shaped like a parachute and sits within the ribs. The esophagus 118 passes through the diaphragm 116 and joins with the stomach 120. The left lobe 122 of the liver 121 lies anteriorly of the esophagus 118 and the fundus-cardia junction 119. In one aspect of the invention, an expandable device is implanted in an extra-gastric location (i.e., outside of the stomach) generally indicated at 124, and then expanded to occupy a space that the fundus of the stomach would ordinarily expand into when the stomach is filled with food. The expanded device prevents this expansion by the fundus, thereby limiting the volume of the cavity in the stomach to a much smaller volume than if the fundus had been allowed to expand into the space. Alternatively, the device is expanded to apply pressure to the fundus of the stomach in a downward direction (e.g., in a direction toward the transverse axis 112 shown, with some transverse movement toward the median axis 110 shown), and optionally, additionally to the main body of the stomach, to reduce the volume inside the stomach to effect satiety in the patient with relatively less food ingested, relative to what the patient would require for satiety without the implant in place.

Devices

At least some embodiments of devices described herein can be implanted trans-orally, with a relatively quick and simple procedure that requires no general anesthesia and wherein the device may be passed through the mouth of a patient and into the cavity within the stomach. In some embodiments, a single, small opening is made through the stomach wall to pass the device therethrough. In at least one embodiment, the device has a single expandable member that is self anchoring or can be easily anchored to maintain the simplicity and minimal invasiveness of the procedure.

In other embodiments, more complex configurations of expandable members may be provided, where a device can contain one or more expandable members. The devices described herein can alternatively be implanted by at least one of percutaneous, laparoscopic, trans-oral and open surgical procedures. Devices that can be implanted percutaneously can alternatively be implanted using laparoscopic procedures. Devices that can be implanted trans-orally can alternatively be implanted using percutaneous or laparoscopic procedures.

Devices described herein can be implanted permanently, but are also configured for reversibility, to facilitate relatively simple removal procedures, should it be desired to remove a device. Alternatively, devices according to the present invention can be implanted temporarily, such as over a period of months, and then removed or disabled when further treatment is no longer required, or to allow an alternative treatment to be applied.

Expandable Member Configurations

One possible location for placing an expandable member portion of a device described herein is in the abdominal cavity between the fundus 120f and the wall of the diaphragm 116. Depending upon the shape of expandable member 10em of device 10, expandable member, or portions thereof can be placed lateral, posterior and/or superior to the fundus of the stomach. Further, when in an expanded configuration, expandable member 10em can optionally only abut or lie adjacent to the stomach wall, without imparting any significant deformation forces thereto. However, when the patient eats and the stomach begins to fill, expandable member 10em in this case prevents the stomach from expanding into the volume occupied by expandable member 10em. In such a case, the stomach becomes "deformed" as it attempts to expand and can only expand in a limited fashion, if at all, around a portion of the perimeter of expandable member 10em. Thus, upon expanding the device, the device expands between the wall of the diaphragm 116 and the fundus 120f, exerting pressure on, or at least preventing expansion of the fundus. Further details of methods for treatment of obesity, including procedures for implanting devices described herein are described below.

Figure 2:
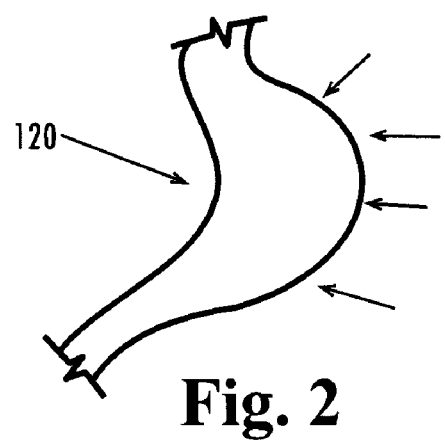
FIG. 2 illustrates (by arrows) potential locations on the stomach wall that can be compressed by one or more expandable devices as described herein.

As noted above, an expandable device can be implanted adjacent a surface of the stomach wall, either in contact therewith or at a predetermined distance therefrom, to prevent expansion of the stomach into a volume occupied by the expandable device. Alternatively, some embodiments of the devices described herein can be configured and placed to exert an external compression on one or more locations of the stomach to deform the stomach wall, thereby decreasing the internal volume of the cavity within the stomach that accepts food and liquid intake. FIG. 2 illustrates (by arrows) potential locations on the stomach 120 wall that can be compressed by one or more expandable devices as described herein.

Figure 3A:
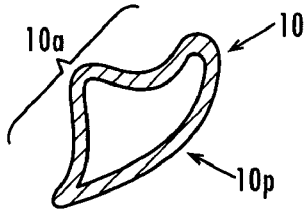
FIGS. 3A-3O show various embodiments of expandable devices which are inflatable to effect expansion thereof.
Figure 3B:
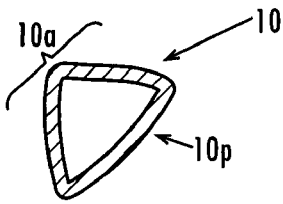
Figure 3C:
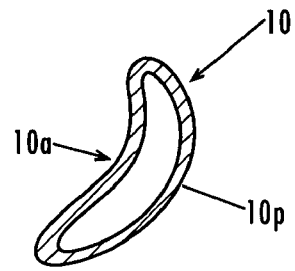
Figure 3D:
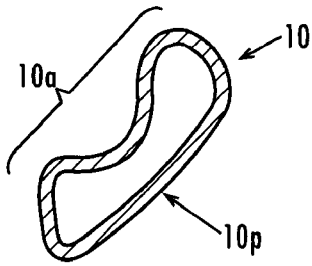
Figure 3E:
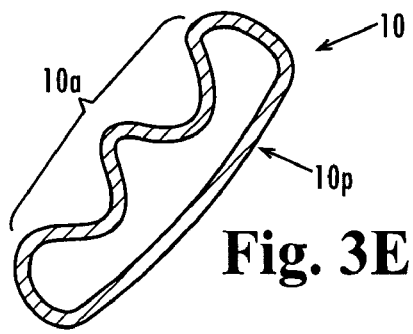
Figure 3F:
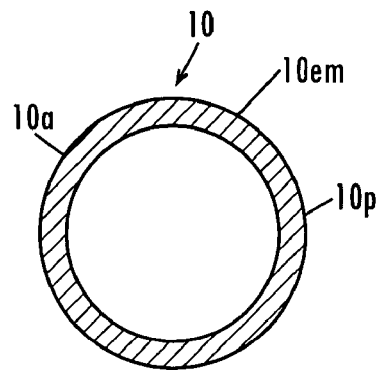
Figure 3G:
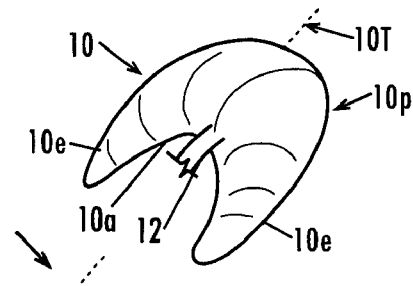

FIGS. 3A-3F show several different embodiments of expandable devices 10 which are inflatable to effect expansion thereof, and which are shown in cross-section in expanded configurations. Surfaces 10a are configured to abut the stomach wall, while other surfaces, typically surfaces 10p are configured to abut one or more other structures in the abdominal cavity. FIGS. 3G-3N are perspective illustrations of further variations of inflatable expandable devices 10 according to the present invention. In FIG. 3G, device 10 is substantially crescent-shaped, wherein end portions of the device, when device 10 is inflated, have first cross-sectional areas that are substantially less than the cross-sectional area of the central portion of device 10. The surface 10a, which is configured to be placed adjacent to a surface of the stomach wall, is substantially concave. End portions 10e tend to wrap around the wall of the stomach 120 as the central portion is placed adjacent to or against the stomach wall. Additionally, device 10 can be configured so that when inflated to expand device 10, ends 10e converge toward the central transverse axis 10T of device 10 (in the directions of the arrows shown) to form a closer fit against the stomach wall and/or apply additional resistive force to the expansion of the stomach wall. In any case, ends 10e help to prevent migration of device 10 relative to the stomach 120 in directions opposite to the directional arrows shown in FIG. 3G. FIG. 3G also shows a partial view of conduit 12 that is in fluid communication with device 10 and used to inflate device 10 according to one method embodiment. In other embodiments, conduit 12 can be placed in fluid communication with device 10 at other locations of the device 10, such as an end 10e or along surface 10p, for example. For this reason, conduit 12 is not shown in the other inflatable embodiments of other Figs., as the location of connection of conduit 12 to device 10 may vary. Thus, although conduit 12 is shown connecting at surface 10a of device 10, the present devices are not limited to this placement, as conduit 12 could be connected at other locations on the inflatable portions of devices 10.

Figure 3H:
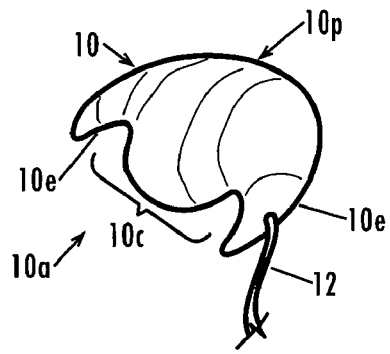

FIG. 3H shows a variation of the device of FIG. 3G, wherein the crescent shape has been modified to a modified-crescent shape, in which the surface configured to abut the stomach is convex at the central portion when device 10 is inflated, to provide increased deformation of the stomach wall, as compared to the amount of deformation applied by device 10 in FIG. 3G. End portions 10e function similarly to that described with regard to FIG. 3G. The "bulge" in the central portion 10c of device 10 can be created by molding such bulge into device 10 so that it is existent in device 10 even when in a contracted or deflated state. Alternatively, the portion of device 10 that forms the bulge can be formed with a thinner wall than the rest of device 10, or can otherwise be made to be more expandable (e.g., such as by making it more compliant than the remainder of the device).

Figure 3I:
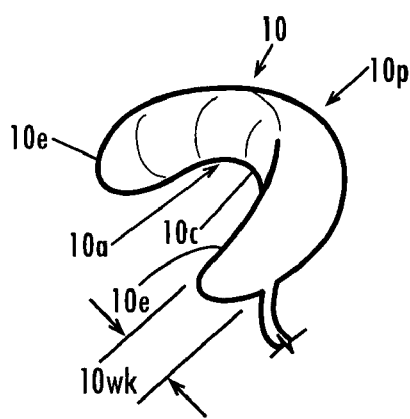
Figure 3J:
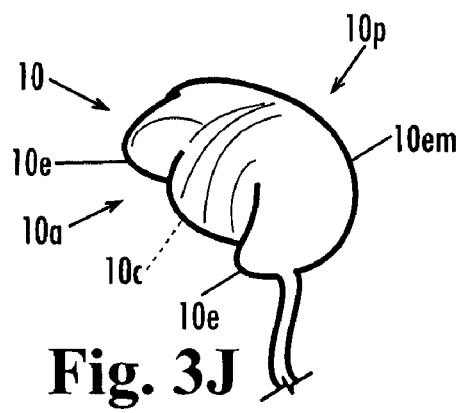

FIG. 3I shows a "cupped scoop" configuration, which, similar to the crescent configuration provides a concave surface 10a and a convex surface 10p. In this arrangement, ends 10e have cross-sectional areas, or at least widths 10w that are substantially as large as the cross-sectional area or width of central portion 10c. Additionally, the radius of curvature of surface 10a about the longitudinal axis L of device 10 is much larger than that of the crescent design, which provides a broader contact surface for engaging the stomach wall. FIG. 3J shows a variation of the device of FIG. 3I, wherein the cupped scoop shape has been modified to a modified-cupped scoop shape, in which the surface configured to abut the stomach is convex at the central portion 10c when device 10 is inflated, to provide increased deformation of the stomach wall, as compared to the amount of deformation applied by device 10 in FIG. 3I. End portions 10e function similarly to that described with regard to FIG. 3G. The "bulge" in the central portion 10c of device 10 can be created by molding such bulge into device 10 so that it is existent in device 10 even when in a contracted or deflated state. Alternatively, the portion of device 10 that forms the bulge can be formed with a thinner wall than the rest of device 10, or can otherwise be made to be more expandable (e.g., such as by making it more compliant than the remainder of the device). In either of the embodiments of FIGS. 3H and 3J, the central portion 10c, including portions of both surfaces 10a and 10p can, in combination, form a substantially spherical shape when inflated.

Alternatively, the bulge in central portion 10c on surface 10a can have a curvature different from hemispherical, but still convex.

Figure 3K:
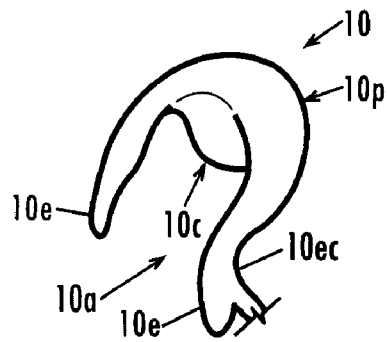

FIG. 3K shows a configuration of device 10 that is boomerang or sickle-shaped. Similar to the embodiments described above, end portions 10e can function to prevent migration of device 10 from its position adjacent a stomach wall and/or may provide additional displacement to prevent expansion of the stomach wall, further limiting the volume of the cavity inside the stomach 120. The bulge at the portion 10c between end portions 10e functions similarly to that described above with regard to FIGS. 3H and 3J and can be made in any of the same manners. Further alternatively, the bulge can be formed as a separately inflatable member, that is, a balloon that is inflatable and deflatable independently of the main inflatable body of device 10. In such instances, conduit 12 can be provided with two lumens for separate control of inflation and deflation of the two balloons. The embodiments of FIGS. 3H and 3J can be similarly constructed. One or both ends 10e may contain an additional curve 10ec so that the distal end (or proximal end, depending on which end is curved) of end portion 10e is directed away from the stomach wall. This feature may help with positioning of device 10 adjacent the stomach 120, to further ensure that the ends of the device 10 do not catch on the stomach wall during placement, and/or to prevent the occurrence of pressure concentrations at the ends of the device against the stomach wall. Additionally, as will be described in further detail, the curve 10ec shown may prevent or substantially reduce pressure against the spleen 128 when device 10 is implanted between the stomach 120 and diaphragm 116 as described in an embodiment herein.

Figure 3L:
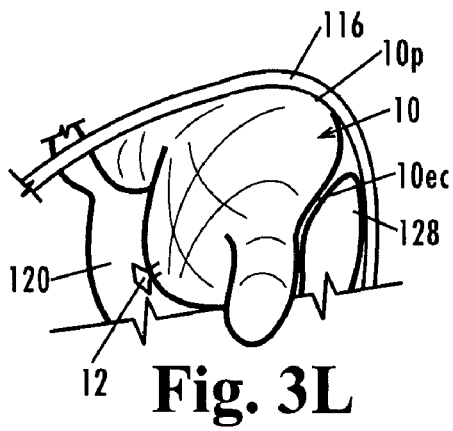

FIG. 3L illustrates a device 10 similar to that described with regard to FIG. 3H, but including a concave curvature 10ec on the proximal end portion of surface 10p that is configured to avoid contact with the spleen 128 or reduce pressure against the spleen 128 relative to a configuration where surface 10p has a continuous convex curvature. Thus, for example, when device 10 is positioned between the diaphragm 116 and stomach 120 and inflated as shown, surface 10ec does not contact or only contacts spleen 128 with minimal pressure, so that spleen 128 is not substantially compressed.

Figure 3M:
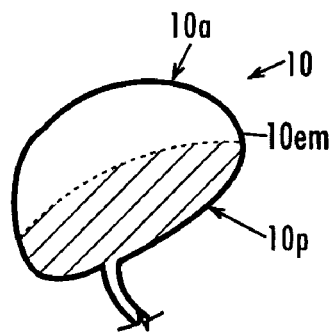

FIG. 3M shows an inflatable device 10 having a substantially flat surface 10p and a convex surface 10a. The substantially flat surface 10p can be particularly advantageous when device 10 is positioned so that surface 10p abuts the interior surface of the abdominal muscles, diaphragm, or some other structure that is adjacent the skin and subcutaneous layers of the patient. The flat surface 10p is configured so as not to expand, or to expand only minimally, as the majority of the expansion proceeds outwardly in the direction of surface 10a during inflation. This may prevent or substantially reduce a bulge from being visualized externally of the patient. Additional features can be provided to make surface 10p less expandable than surface 10a, as discussed below, to further prevent expansion of surface 10p under inflation pressure. Surface 10a, although shown as a continuous convex surface, can be modified to provide other surface conformations, including any of those shown and discussed above.

Figure 3N:
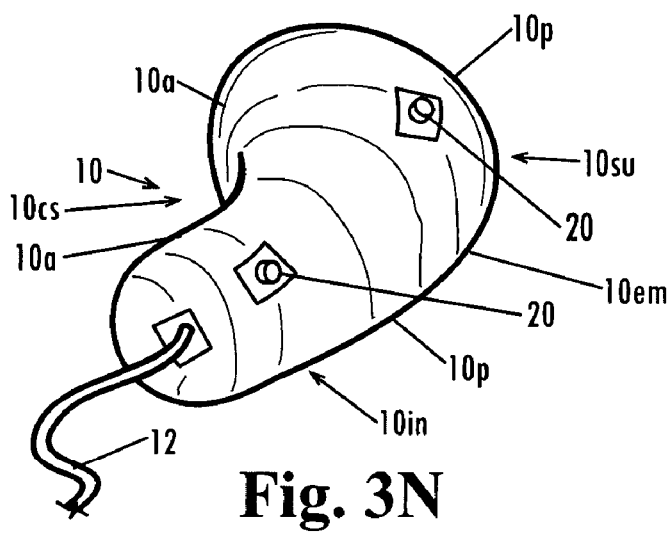

FIG. 3N illustrates another expandable member configuration in which expandable member 10em has a relatively large, bulbous superior portion 10su that tapers to an inferior tubular portion 10in. Tubular section 10in has a substantially smaller cross-sectional area than bulbous portion 10su. Bulbous portion 10su can have a substantially elliptical cross-sectional shape near the end of expandable member and tapers as it descends inferiorly toward tubular portion 10in, to form a concave groove or surface 10cs medially that is configured to deform the stomach to have a smaller, sleeve-shaped inner cavity, as described further below, and to force the stomach 120 to be more centrally located in the abdominal cavity. The bulbous portion is configured to be positioned in the sub-diaphragmatic space, between the diaphragm 116 and the stomach 120 and, as it is inflated, moves the fundus medially towards the liver. When device 10 is properly positioned, tubular portion 10in is inferior to bulbous portion 10su and, when inflated, applies pressure to the body of the stomach to effect conformational change by pushing it posteriorly against the spinal column. As inflated, device 10 fills in a sub-diaphragmatic space occupied by the omentum, a portion of the stomach, and a space into which the fundus is typically allowed to expand.

Figure 3O:
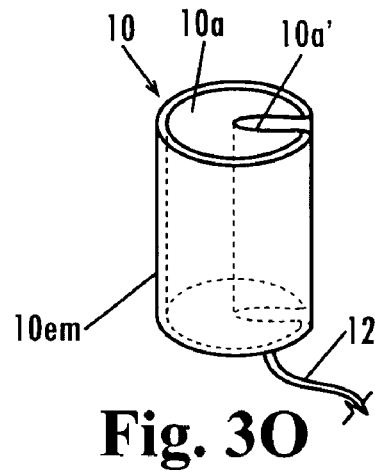

FIG. 3O shows an inflatable, expandable device 10 having expandable member 10em that is substantially cylindrical when inflated. Alternatively, this configuration can be made in the same shape with a mechanically expanding member 10em, such as by using metallic struts or wires to construct the expandable member 10em, similar to the construction used in the device 10 in FIG. 9 below. Device 10 is configured and dimensioned to be wrapped entirely around the stomach 120, and fastened around the stomach to provide a restraint that prevents the stomach from expanding beyond the boundary provided by the surface 10a of device 10 that interfaces with the stomach 120. Fastening may be performed by providing interengaging buckle features on multiple belts portions that extend from the end edges of device 10, VELCRO® or other hook and loop type fasteners provided on the overlapping edges, adhesives, hooks, suturing, buttons and button holes and/or other fastening expedients. Additionally, device 10 may be configured with a protrusion 10a' that protrudes radially inwardly from surface 10a into the spaced defined generally by the generally cylindrically-shaped device 10. Protrusion 10a' may be inflatable or solid. Protrusion 10a' is driven into the stomach wall upon wrapping and fastening device 10 around the stomach, so that it deforms the stomach wall inwardly, thereby reducing the volume of the cavity within the stomach. Additionally, the amount of inflation in device 10 can be varied to vary the amount of compression on the stomach to further limit the volume of the cavity in the stomach. In the example shown in FIG. 3O, when device 10 is installed around the stomach, protrusion 10a' forces a fold into the stomach 120, thereby reducing the volume of the cavity in the stomach 120. It should be noted that device 10, while shown to be generally cylindrical in FIG. 3O, may be modified to still be configured to wrap around the stomach, but to follow the contours of the stomach in its natural shape more closely. Also, the shape and/or amount of protrusion of protrusion 10a' may be varied. Multiple protrusions may also be employed.

Figure 4:
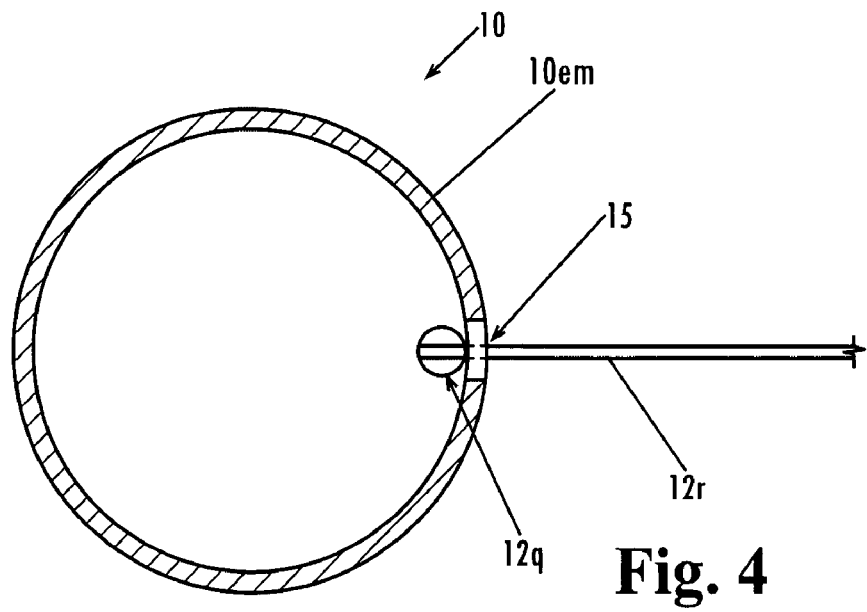
FIG. 4 illustrates a device having an inflatable member that has a valve in the wall thereof.

FIG. 4 illustrates an expandable member 10em of device 10 having a valve 15 in the wall thereof. The valve 15 is a self-sealing valve such as an elastomeric or gel membrane. Initially, a removable inflation tubing 12r with an expandable tip 12q is inserted through valve 15 and attached to the expandable member 10em by expanding tip 12q. The expandable member is positioned in the desired location with expandable tip 12q in its enlarged configuration. The expandable tip 12q can be an inflatable member or an expandable framework. After expandable member 10em is positioned, it is enlarged to the desired size using the removable inflation tubing 12r. When the desired size is reached, the expandable tip 12q is collapsed, the removable inflation tubing 12r is retracted and the tip 12q is removed through the self-sealing valve 15.

Other shapes and configurations of inflatable device can also be used, including football-shaped, hourglass shaped or substantially tubular shaped devices. Further alternatively, device 10 may include more than one expandable member, as noted above. Still further, device may be formed as a composite having one or more expandable members, and one or more non-expandable members. Further specific examples of such devices are described in the following co-pending, commonly owned applications: application Ser. No. 11/407,701 filed Apr. 19, 2006 and titled. "Devices and Methods for Treatment of Obesity", application Ser. No. 11/716,985 filed Mar. 10, 2007 and titled "Devices and Methods for Treatment of Obesity", and application Ser. No. 11/716,986 filed Mar. 10, 2007 and titled "Devices and Methods for Treatment of Obesity". Application Ser. Nos. 11/407,701, 11/716,985 and 11/716,986 are hereby incorporated herein, in their entireties, by reference thereto.

Figure 5A:
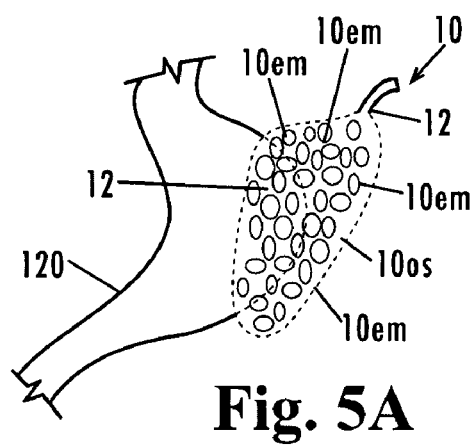
FIG. 5A illustrates a device that includes a plurality of expandable members 10em configured in a "grape bunch"-like structure.
Figure 5B:
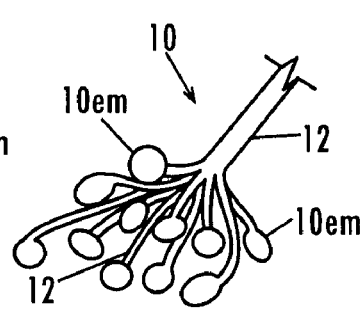
FIG. 5B is a partial, detailed view of FIG. 5A.
Figure 5C:
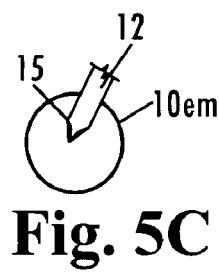
FIG. 5C shows an expandable member provided with a valve.

FIG. 5A illustrates a device 10 that includes a plurality of expandable members 10em configured in a "grape bunch"-like structure. Each of the expandable members is individually inflatable via its own conduit 12 connecting thereto, each of which is in fluid communication with a main conduit 12 used to input an inflation medium, as illustrated more clearly in the partial view of FIG. 5B. Further, each expandable member 10em may be provided with a valve 15, as illustrated in FIG. 5C, so that they are isolated, so that if one or more expandable members 10em bursts or otherwise fails, this will not cause the remainder of the expandable members to deflate or lose pressure, thus providing an advantage over a device that has a single inflatable expandable member. The plurality of expandable members 10em in the grape bunch-like structure may include three to five expandable members; up to 10 expandable members, up to twenty expandable members, up to 50 expandable members or up to 100 expandable members.

Optionally, an "over-shell" 10os (e.g., silicone layer or other atraumatic layer) may be provided over the grape bunch-like structure to provide a smoother, more continuous and/or more atraumatic interface with the tissues that it contacts.

Expandable members 10em may be inflated to variable amounts, according to need or placement of the structures. For example, if a right side of the grape bunch-like structure is positioned in contact with relatively rigid structures (e.g., tissues supported by the rib cage), then the expandable members 10em on the right side of the structure may expand less than the expandable members 10em on the left side of the structure, even given equal amounts of pressure inputted thereto via the main conduit 12. Valves 15 may be reversible or two-way, such that they allow deflation of the expandable members upon application of a negative pressure below a predetermined threshold pressure, to allow deflation of the expandable members 10em, or reduction in the pressures contained therein.

Inflatable members described herein can be inflated with fluid, e.g., gas or liquid or both. Examples of gases or liquids that can be used to inflate inflatable members/devices 10 include, but are not limited to: carbon dioxide, helium, isotonic dextrose solution, iostonic saline solution, air. It may be preferable to inflate with one or more gases, to minimize the weight of the implanted device 10, as a heavier, fluid-filled device may be more noticeable to the patient. Alternatively, the buoyancy of an implanted device 10 can be adjusted by the amount of gas that is inputted to an expandable member, relative to an amount of liquid inputted to that expandable member. Alternatively, devices 10 can be inflated with a porous gel that is porous or microporous to encapsulate air or other gas bubbles, thereby reducing the weight of the gel while still permitting it to apply volumetric pressure to expand an inflatable member. Such gels may be settable, such as ultra-violet (uv) curable or otherwise chemically curable, or, alternatively, can remain in the gel state, so that they can be readily removed or added to, to increase or decrease the amount of inflation/expansion of the expandable member. Gels can be made from a flowable viscoelastic substance made of a polymer mixture, such as silicone oil, boric acid, hyaluronic acid, polyacrylic acid or combinations thereof, for example. The gel, as delivered into the expandable member 10em (e.g., such as by injection or the like) can be aerated or infused with carbon dioxide or an inert gas to create a deformable or non-deformable cellular structure that encapsulates the gas in cells, and thus has relatively low mass but still has significant resistance to compression or deformation.

Device 10 can further include one or more reinforcing elements that can be attached externally of the inflatable member or can be molded into the inflatable member. For example, reinforcing elements can be made from hard plastics, such as polycarbonate, glass-filled polymers, polyvinyl chloride, or thicker layers of elastomers, such as polyester, polyurethane, etc, or from PTFE, biocompatible malleable metals, or fiber reinforced polymers. A reinforcing element can be positioned in a mold in a predetermined configuration and then molded into the inflatable member by molding the inflatable member around the reinforcing element. Alternatively, reinforcing elements can be bonded to the expandable member by heat, adhesives and/or solvents. Additionally, or alternatively, a portion of an expandable member may be made non-compliant or semi-compliant, while another portion is compliant. This can be accomplished by use of reinforcing element(s) as described above and/or by making a portion of an expandable member from a compliant material, while another portion is made from a semi-compliant or non-compliant material. Another method for making expandable members having preferentially expanding portions or preferentially expanding shapes includes creating wall thickness variations in different portions of the expandable member where the relatively thinner wall portions expand preferentially relative to the relatively thicker wall portions.

Figure 6A:
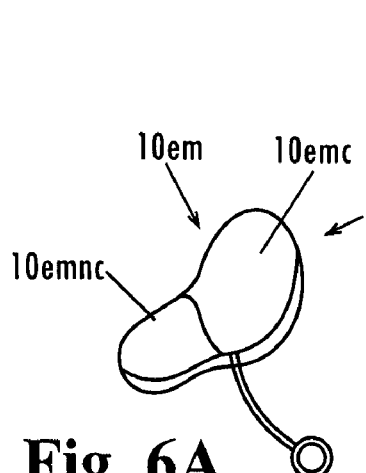
FIG. 6A shows a device having a compliant portion and a noncompliant or semi-compliant portion.
Figure 6B:
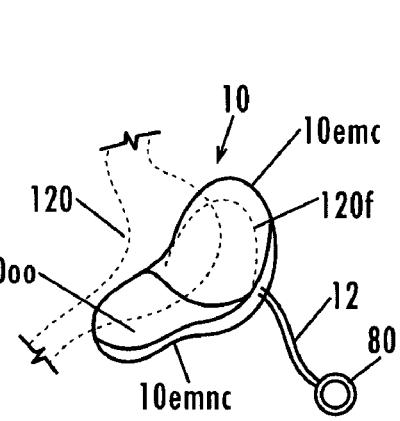
FIG. 6B shows a device having a compliant portion and a noncompliant or semi-compliant portion.

FIGS. 6A-6B illustrate a device 10 having an expandable member 10em that includes a compliant portion 10emc and a noncompliant portion 10emnc. Alternatively, device 10 could be modified so that noncompliant portion 10emnc is semi-compliant. In FIG. 6A, the compliant portion 10em is configured to be expandable by elastic deformation once the chamber has been fully filled. In contrast, noncompliant portion 10emnc does not elastically deform and thus only expands to the fully filled shape thereof, but does not elastically deform to expand further. Alternatively, noncompliant portion 10emnc may be a mechanically expandable portion that only expands to a predetermined size and configuration. FIG. 6B illustrates device 10 implanted relative to the stomach 120. The compliant portion 10emc of expandable member can be further expanded by increasing pressure inputted through conduit 12 to effect additional compression/restriction of the fundus portion of the stomach 10f. However, this will not increase or expand the noncompliant portion 10emnc. In this case, the noncompliant portion 10emnc is designed and configured so as not to be expandable by elastic deformation, so as not to close off the antrum, 120a, as this portion of the stomach needs to remain relatively unrestricted to allow normal movement of food into the small intestines.

Figure 6C:
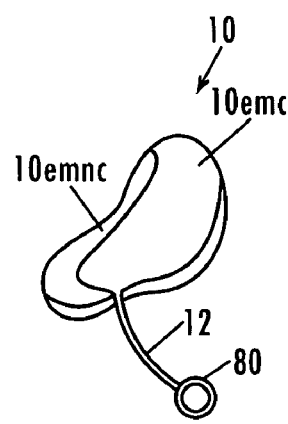
FIG. 6C shows a device having a compliant portion and a noncompliant or semi-compliant portion.
Figure 6D:
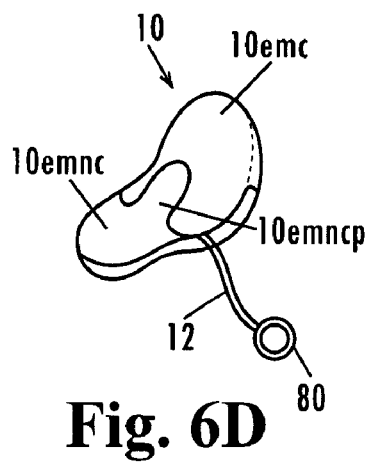
FIG. 6D shows a device having a compliant portion and a noncompliant or semi-compliant portion.

Various other arrangements of expandable members 10*em* having compliant 10*emc* and noncompliant 10*emnc* or semi-compliant portions can be configured, and are custom-designable to be appropriate for their intended use. For example, FIG. 6C illustrates a device 10 where less compression of the main or central portion of the stomach is desired, so that the noncompliant portion 10*emnc* extends superiorly along the medial side that will be placed in contact with the stomach. FIG. 6D illustrates an example, where noncompliant portion 10*emnc* extends superiorly on an anterior surface of the expandable member 10*em* to form a patch 10*emncp* configured to enhance tissue ingrowth from the anterior abdominal wall for anchoring device 10 thereto. Patch 10*emncp* may be provided with a roughened surface or other tissue ingrowth-enhancement features. Additionally the extent of the anterior portion of noncompliant portion 10*emnc* may be provided to prevent a bulging appearance on the external surface of the abdomen of the patient.

The different portions 10*emc* and 10*emnc* may be formed from different material, such as by co-molding, or the like. Alternatively, a noncompliant material (e.g., polyester mesh reinforced polymer, or the like) may be over-coated over a compliant balloon in the locations where the noncompliant portion is desired to be formed. Other structural reinforcements may be provided in the noncompliant portion, as already note above.

Figure 7:
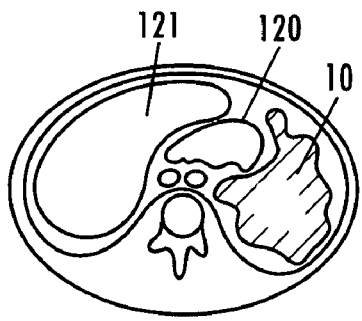
FIG. 7 diagrammatically illustrates the use of a space filling foam that can be use as the expandable member of a device described herein.

FIG. 7 diagrammatically illustrates the use of a space filling foam that can be used as the expandable member 10. For example, the foam can be sprayed in place or injected in order to form expandable device 10 that fills up substantially all of the sub-diaphragmatic space into which the fundus normally expands.

Figure 8A:
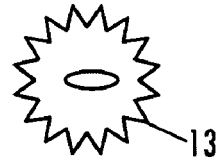
FIG. 8A illustrates a self-inflatable device in a deflated configuration.
Figure 8B:
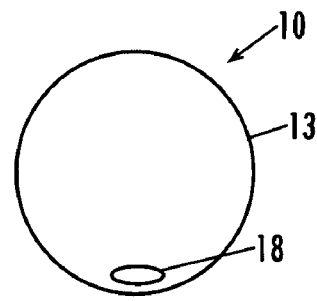
FIG. 8B illustrates the device of FIG. 8A after self-inflating.

Inflatable devices 10 can be inflated via a conduit 12 connecting device 10 with a source of inflation medium located outside of the patient, as mentioned above and as described in more detail below. Alternatively, device 10 can be configured to be self inflatable, such as by initiating a chemical reaction within device 10 to produce pressurized gas and expand the device, once the device has been properly implanted in an intended location. FIG. 8A illustrates an inflatable device formed from a noncompliant material (a device having a compliant inflatable member or semi-compliant inflatable member can also be used, and a compliant inflatable member may not have folds in it in the deflated configuration) in a deflated configuration and containing capsule 18. Once device 10 has been properly implanted, anchored and positioned as desired, capsule 18 is squeezed, crushed, or otherwise deformed, using graspers, or other similar surgical instrument. This deformation increases the pressure within capsule 18, causing a membrane separating reactants in the capsule to rupture, at which time the chemical reactants react with one another to generate pressurized fluid. For example, the reactants can combine to generate a chemical reaction that creates gas as an end product. Combining an acid and a base will produce a gas to inflate device 10. One such combination to produce $CO_2$ is acetic acid and bicarbonate of soda. The amounts of chemicals contained in capsule 18 can be predetermined to generate an amount of gas sufficient to inflate device 10 to a predetermined pressure, as illustrated after completion of the chemical reaction in FIG. 8B.

Figure 9:
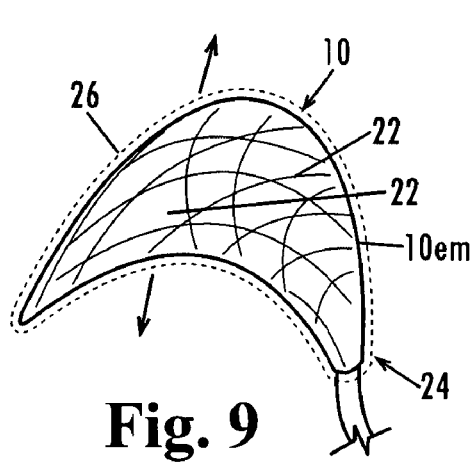
FIG. 9 shows a self expanding device comprising a self-expanding body formed of intersecting resilient structural elements.

As an alternative, or in addition to inflatable members, expandable devices 10 are provided to include expandable members 10*em* that are expanded via a mechanically expandable mechanism. For example, FIG. 9 shows self expanding device 10 comprising a self-expanding member 10*em* formed of intersecting resilient structural elements (in this case, struts) 22 that can be made of a resilient steel such as spring steel, nickel-titanium alloy, titanium or other biocompatible, resilient metal, or resilient biocompatible polymer, for example. Device 10 is collapsible to a compressed configuration so as to be deliverable through a sheath 24 to a target site where device is to be expanded and positioned for implantation. Device 10 is biased toward the expanded configuration, so that upon being ejected from sheath 24, device 10 self expands to the expanded configuration, in the directions of the arrows shown in FIG. 9. Device 10 can be optionally covered with an elastic membrane 26 to prevent adhesions or ingrowth into the lattice of struts forming the expandable cage or basket. Implantation of device 10 is reversible, as device 10 can be collapsed by drawing it back into sheath 24 in a subsequent procedure to remove the device, as tension of the device and drawing it into the opening of the sheath will cause struts to move back into the contracted configuration. Other examples of configuration of mechanically expandable devices 10 that can be employed in the present invention are described in application Ser. Nos. 11/407,701 and 11/716,986.

Figure 10:
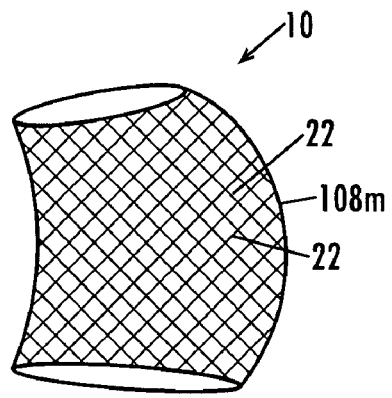
FIG. 10 illustrates one embodiment of a mechanically self-expanding member of an intra-gastric device.

FIG. 10 illustrates device 10 having a mechanically expandable member 10*em*, wherein device 10 is configured for intra-gastric implantation, as described in detail below. Expandable member 10*em* can be self-expanding, and may be formed of intersecting resilient structural elements (e.g., struts or wires) 22 that can be made of a resilient steel such as spring steel, nickel-titanium alloy, titanium or other biocompatible, resilient metal, or resilient biocompatible polymer, for example. Device 10 is collapsible to a compressed configuration so as to be deliverable through a sheath 24 to a target site where device is to be expanded and positioned for implantation. Device 10 can be biased toward the expanded configuration, so that upon being ejected from the sheath, device 10 self expands to the expanded configuration, as it is shown in FIG. 8. Device 10 can optionally be covered with an elastic membrane to prevent adhesions or ingrowth into the lattice of struts forming the expandable member 10*em*. Implantation of device 10 is reversible, as device 10 can be collapsed and withdrawn from the surgical implant location.

FIG. 11 illustrates a compound or "hybrid" expandable device 10 having been positioned between the diaphragm 116 and stomach 120 and expanded against the stomach to deform the stomach wall inwardly. As used herein, a "hybrid" device is one that may be expanded by different expansion media or techniques or mechanical features. As non-limiting examples, a hybrid device may be a device with a structural support and a fluidly inflatable member, a hybrid device may have mechanically and gas expandable aspects, a hybrid device may have mechanically and liquid expandable aspects, a hybrid device may have a chamber expandable via liquid plus a closed foam component, a hybrid device may have a chamber expandable via gas plus a foam component, etc. A compound expandable device includes hybrid expandable devices, but may also be a device, for example, having a expandable member that is expandable by gas or liquid or both, plus a foam member that is not typically expanded during use, but which is insertable into the expandable member, or is usable in conjunction externally of the expandable member. In the example of FIG. 11, expandable member 10*em* of device 10 includes a mechanically expandable portion 10*m* (shown as intersecting struts 22, although other mechanically expandable configurations can be substituted) with one or more inflatable portions 10*inf* connected thereto. In the example shown, inflatable members 10*inf* are attached to form surface 10*a*, and can be independently inflatable, or fluidly connected so as to be inflated through the same inflation lumen 12. Upon inserting device 10, the mechanically expanding portion 10m is first allowed to self expand, after which, the inflatable portion(s) can be adjustably inflated to produce additional deformation of the stomach, as well as to provide a softer interface between the stomach wall and device 10.

FIG. 12 illustrates another example of a hybrid expandable member in which a self-expanding, mechanically expandable portion 10m is provided as a stent-like structure of intersecting struts 22 that are self-expandable, like the self-expansion of a stent used in vascular procedures. The mechanically expandable portion 10m may be made of metal such as stainless steel or nickel-titanium alloy, but is more typically made of resilient polymer struts 22. The mechanical portion 10m is encapsulated by an inflatable portion 10inf, which may be a compliant material, such as silicone (preferably, high tear strength silicone, such as NUSIL 6400 silicone, or the like), or other material described herein, or may be or include a non-compliant or semi-compliant layer.

FIGS. 13A-13C illustrate another embodiment of a hybrid expandable member 10em. In this example, mechanical member 10m is self-expanding and is formed as a continuous coil 23. Coil 23 may be formed of any of the materials described above and is configured to self-expand to its expanded configuration shown in FIG. 13A. Upon application of compressive forces, which may be mechanical and/or applied by drawing a vacuum on inflatable member 10inf, mechanical member 10m compresses by collapsing like a SLINKY® as illustrated in FIG. 13B. This configuration has a smaller cross-sectional area than that shown in FIG. 13A and is used for implantation of the device 10. Once expandable member 10em has been positioned in or near a desired implantation target site, compressive forces on mechanical member 10m can be release, whereupon mechanical member 10m self-expands, as illustrated in FIG. 13C. The layer encapsulating mechanical member 10m may form an inflatable member 10inf that can be formed of any of the materials described above with regard to FIG. 12, or may be expanded only by the mechanical expansion forces of mechanical portion 10m. In examples where the encapsulating layer 10inf is an inflatable member 10inf, such as is shown in FIG. 13C, inflatable member 10inf can be inflated with any of the inflation media described previously, after self expansion of mechanical member 10m and/or concurrently with the self expansion of expandable member 10m.

The mechanical portions 10m of the embodiments illustrated in FIG. 12-13B may be sandwiched between two layers of the encapsulating polymer, or may be bonded to the inner wall surface of the encapsulating polymer layer, or may be freely movable with respect to the encapsulating polymer layer.

FIG. 14 illustrates another example of a hybrid device 10 in which an inner expandable member 10em1 is at least partially surrounded by an outer expandable member 10em2. At least fifty percent of the surface area of inner expandable member 10em1 may be surrounded by outer expandable member 10em2, or at least seventy percent, or at least ninety percent, or inner expandable member 10em1 may be completely encapsulated by outer expandable member 10em2. For example, inner expandable member 10em1 may be inflated with one or more gases, and outer expandable member 10em2 may be inflated with one or more liquids. Inner expandable member 10em1 may be made of a material that is more gas impermeable than that of outer expandable member 10em2. For example, inner expandable member 10em1 may be non-compliant or semi-compliant or be a compliant material with a thin metallic coating, and expandable member 10em2 may be compliant. For example, expandable member 10em2 may be made of silicone or polyurethane or the like. Other examples of materials for inner expandable member include, but are not limited to: co-extruded EVOH (ethylene-vinyl alcohol copolymer) and polyurethane, with or without a metallic coating. Further examples of materials that can be used to provide a relatively gas impermeable barrier by expandable member 10em1 can be found in provisional application Ser. No. 60/877,595; and application Ser. Nos. 11/407,701, 11/716,985 and 11/716,986.

Two conduits 12 may be separately provided for inflating expandable members 10em1 and 10em2, or a dual lumen conduit 12, as shown, may be provided, with adjustment member 80 being configured to deliver gas, as well as liquid, through different pathways, as explained in more detail below. A reinforcing portion, such as shape pad 16 may be provided to help maintain the desired shape of expandable members 10em1, 10em2, functioning somewhat like a backbone to provide some structural integrity. Additional reinforcing portions 16 may be provided, internally and/or externally of expandable member 10em2, or sandwiched between layers thereof. One or more attachment tabs may extend from the expandable member 10em for anchoring to one or more internal abdominal structures, such as by one or more of suturing, stapling, tacking, adhesives, tissue ingrowth. Reinforcement portions and attachment tabs may be made of reinforced silicone, such as mesh-reinforced silicone, for example.

FIG. 15A illustrates a device having an internal, relatively gas-impermeable expandable member 10em1 and external expandable member 10em2 filled at least in part with liquid, wherein the two expandable members are fillable via a dual lumen conduit 12. Inner lumen $12_1$ is in fluid communication with inner expandable member 10em1 and outer lumen $12_2$ is in fluid communication with outer expandable member 10em2. One or both expandable members 10em1, 10em2 may be optionally be provided with a check valve 15 at the interface between the respective lumen that it is in communication with and the expandable member, to help ensure prevention of leakage from the expandable member.

FIG. 15B illustrates an adjustment member 80 configured for delivery of gas to first expandable member 10em1 and liquid to second expandable member 10em2. A first port $84_1$ is provided for connection with a source of pressurized gas. Port $84_1$ is in fluid communication with conduit 12, and can therefore be used to input pressurized gas to expandable member 10em1. Port $84_2$ is provided for connection with a source of pressurized liquid. Port $84_2$ is in fluid communication with conduit $12_2$ and can therefore be used to input pressurized liquid to expandable member 10em2. Valve mechanisms 84v1, 84v2 are provided to maintain the pressure within the conduits $12_1$, $12_2$ and to only selectively allow fluids to be inputted to or extracted from expandable members 10em1, 10em2. For example, valve mechanisms 84v1, 84v2 can be any of a number of well-known mechanical valves. Additionally, an elastomeric seal 82 (e.g., made from "self-sealing" silicone) may be provided to allow entry into ports $84_1$, $84_2$ via a needle or other appropriately configured delivery mechanism.

Figure 16A:
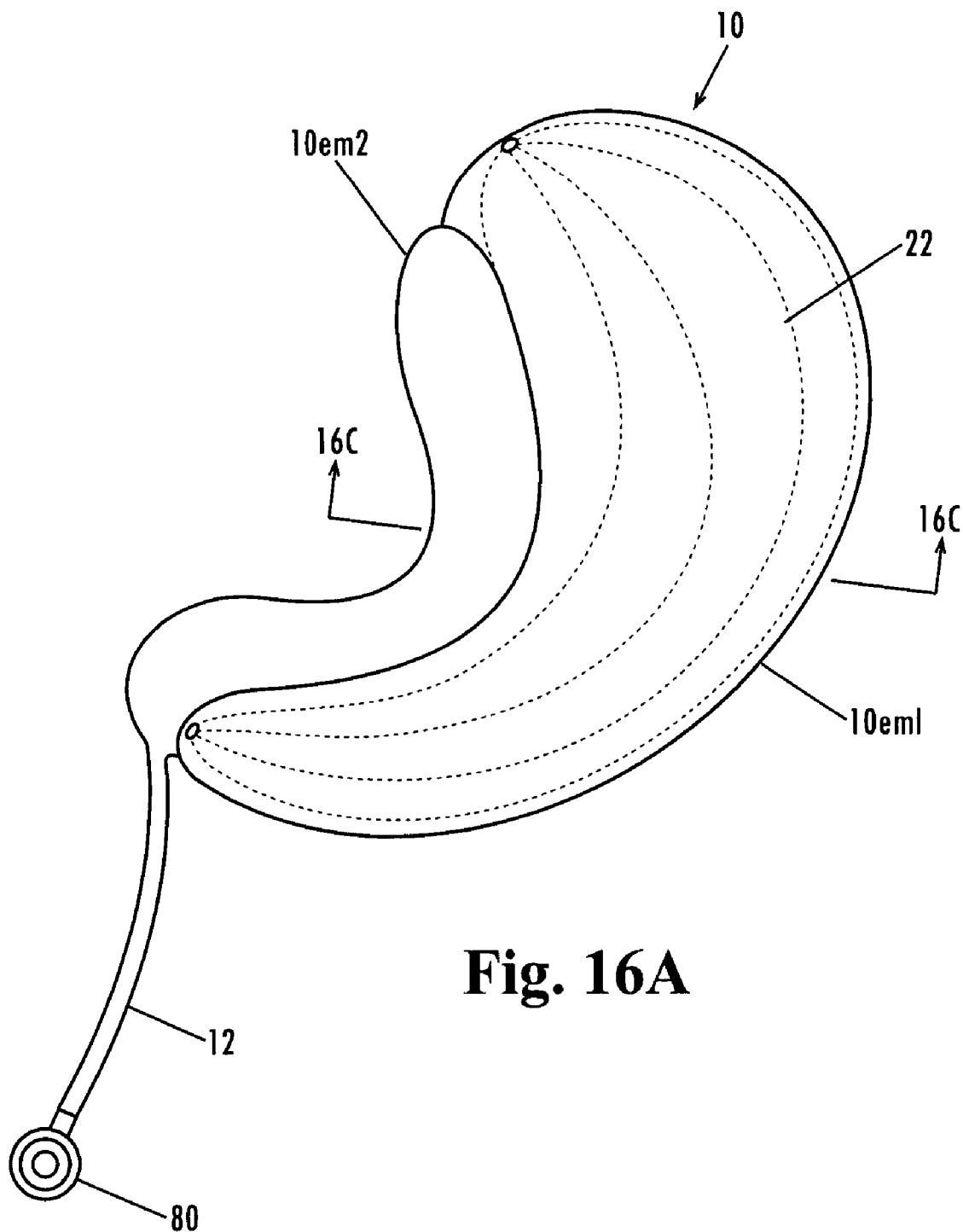
FIG. 16A illustrates another embodiment of a device.
Figure 16B:
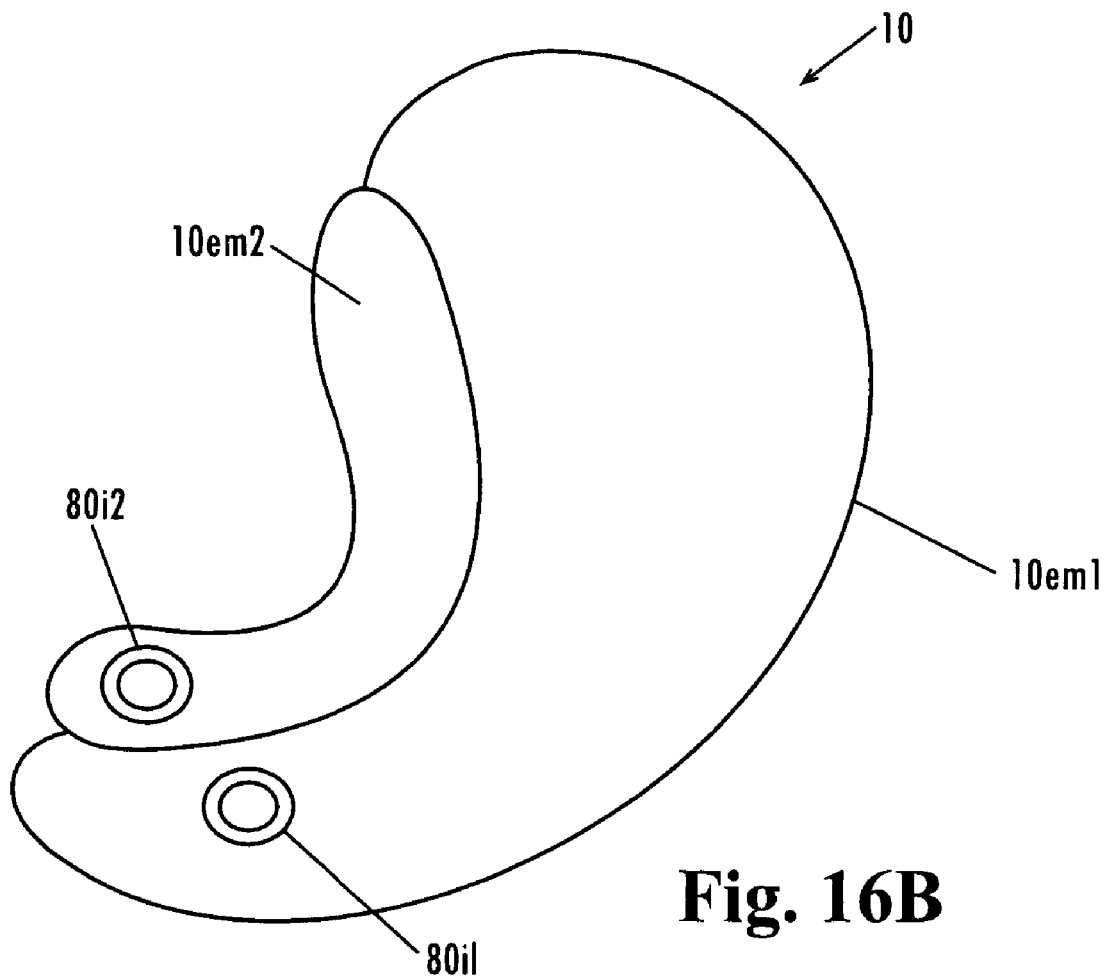
FIG. 16B illustrates a device in which each of the expandable members is provided with an integrated adjustment member.
Figure 16C:
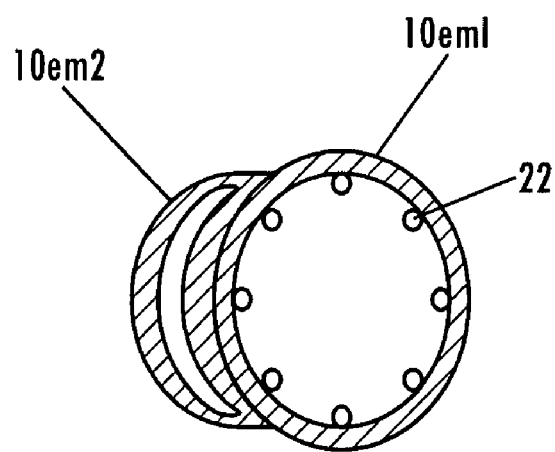
FIG. 16C is a cross-sectional illustration of the device of FIG. 16B.

FIGS. 16A-16C illustrate another embodiment of a hybrid device 10. Expandable member 10em2 is configured to be adjustable in volume and expandable member 10em1 is configured to expand to a relatively fixed volume. In the example shown, expandable member 10em2 is fillable with liquid to provide an adjustable volume thereof by varying the amount of liquid inputted thereto. Expandable member 10em1 is provided with a structurally supported chamber the external wall of which may be inflatable with gas, liquid or liquid and gas.

The material from which the wall of the expandable member 10em1 is made may be compliant, where the structural support members 22 help to maintain the expandable member 10em1 fully expanded to the desired volume. Alternatively, the wall of expandable member can be made non-compliant or semi-compliant. Although not shown, when inflatable, expandable member 10em1 can be inflated via a separate conduit and adjustment member. Alternatively, inflation can be performed through a conduit 12 and adjustment member 80 that is also used to inflate expandable member 10em2, and wherein the conduit 12 and adjustment member 80 is configured in an integrated manner, such as like described above with regard to FIG. 15B, for example, or in some other integrated construction. Further alternatively, expandable member 10em1 may be expandable solely by the mechanical, self-expanding action of struts 22.

Alternatively, one or both of expandable members 10em1 may be provided with an integrated adjustment member 80i. FIG. 16B illustrates a device 10 configured like that in FIG. 16A, except that adjustment members 80i1 and 80i2 are provided integrally with the walls of the expandable members 10em1 and 10em2. In this case, no external conduit 12 is required to extend between an expandable member and an adjustment member, nor does an adjustment member need to be placed at or external of the abdominal wall. Inflation can be performed with an inflation device having a extended needle like structure that can be inserted intra-abdominally, after placement of device 10 intra-abdominally, to inflate or adjust the amount of inflation pressure in an expandable member. The valve and sealing structure of adjustment member 80i can be like any of the examples described with regard to the external adjustment members 80 described herein.

FIG. 16C is a cross sectional view of device 10 of FIG. 16A, taken along line 16C-16C. The struts 22 may be sandwiched between two layers of the encapsulating polymer of expandable member 10em1, or may be bonded to the inner wall surface of the encapsulating polymer layer, like shown in FIG. 16C, or may be freely movable with respect to the encapsulating polymer layer.

FIGS. 17A-17B show views of another embodiment of a hybrid device 10. In this example, expandable member 10em1 is a relatively gas-impermeable chamber, which can be made of a non-compliant material. Any of the material configurations described above with regard to FIG. 15A, expandable member 10em1, can be used to form a relatively gas-impermeable barrier. Accordingly, expandable member 10em1 can be filled with gas to the configuration shown, wherein the expandable member does not substantially elastically deform. Accordingly, the amount of displacement by expandable member 10em1 is relatively fixed. Expandable member 10em2 is fillable with liquid and/or gas, and is elastically deformable/compliant so that the size/amount of displacement by expandable member 10em2 can be varied by the amount of pressurized liquid and/or gas inputted thereto. For example, expandable member 10em2 may be formed of silicone or polyurethane, or other compliant material or material combination.

As shown, expandable members 10em1 and 10em2 are fillable by separately provided adjustment members $80_1, 80_2$ and conduits $12_1, 12_2$, respectively. Alternatively, device 10 can be provided with a single adjustment member 80 and multi-lumen conduit 12 like that described above with regard to FIGS. 15A-15B. In either case, when both gas and liquid are used to fill expandable member 10em2, the gas and liquid can be premixed and inputted through lumen 122, but typically, liquid and gas are sequentially inputted through the same port and lumen 122, one after the other, in either order. Further, input of gas and liquid may be iteratively performed. As noted, expandable member 10em2 may be filled with liquid only, or with gas only, although typically the expandable member 10em2 will be at least partially filled with liquid. A silicone dipped or molded layer 10os may optionally be provided to provide a continuous atraumatic surface, particularly between the junctions between expandable members 10em1, 10em2.

Figure 18:
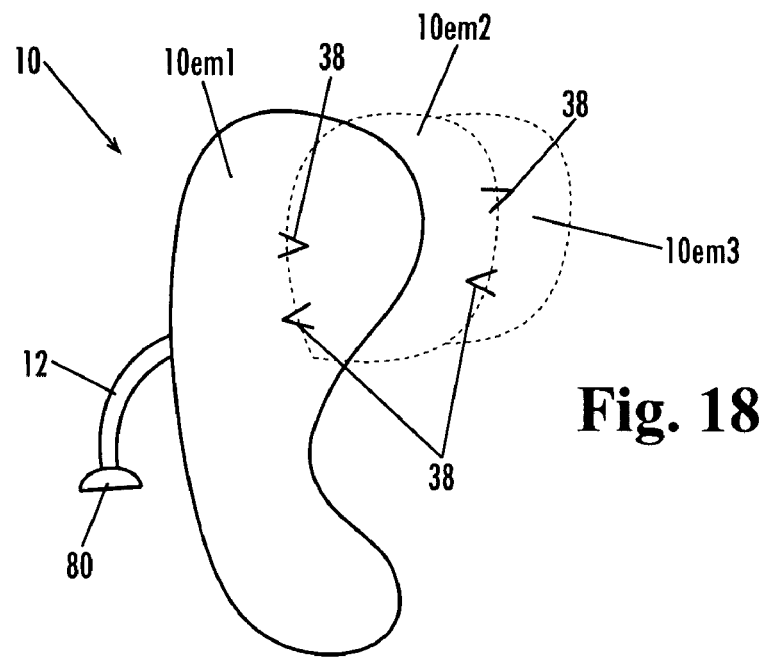
FIG. 18 illustrates an embodiment of a device in which multiple chambers or expandable members are provided, all made noncompliant so as to be relatively gas impermeable.

FIG. 18 shows an embodiment of device 10 in which multiple chambers or expandable members 10em1, 10em2, 10em3 are provided, all made noncompliant so as to be relatively gas impermeable. Although three expandable members are shown, two, four, or more than four expandable members can be provided according to the same principles, to provide a device that is adjustable to change the amount of volume/displacement of the device 10 within the abdominal cavity. Since the expandable members are not elastically deformable, device 10 is made adjustable by the provision of valves 38 between the chambers 10em1/10em2 and 10em2/10em3. An expansion valve 38 between expandable members 10em1 and 10em2 opens at a first predetermined pressure, which is lower that a second predetermined pressure at which expansion valve 38 between expandable members 10em2 and 10em3 opens. Accordingly, expandable member 10em1 is first filled by inputting pressurized gas through adjustment member 80 and conduit 12. Although this embodiment is designed particularly for inflation by gas, it can be alternatively filled with liquid or liquid and gas. Device 10 can be used in the configuration shown by the solid line, where only expandable member 10em1 is inflated and expandable members 10em2 and 10em3 are collapsed and substantially conform to the perimeter of expandable member 10em1.

To increase the volume of device 10 and thus the amount of displacement thereby, pressurized medium (typically gas, but, as noted, liquid or liquid and gas may be used) is added through adjustment member 80 and conduit 12. When the pressure reaches or exceeds the first predetermined pressure, the input valve 38 between expandable member 10em1 and 10em2 opens and expandable member 10em2 begins to fill. Once expandable member 10em2 is filled, if additional displacement is still desired, pressurized medium is continued to be inputted through adjustment member 80 and conduit 12. When the pressure reaches or exceeds the second predetermined pressure, the input/expansion valve 38 between expandable member 10em2 and 10em3 opens and expandable member 10em3 begins to fill. Further details about "this nested chamber" design can be found by referring to application Ser. No. 11/716,985, FIG. 7, and the description thereof. As shown, a pair of valves 38 are provided at the interfaces between chambers. One of each pair (the input valve) functions as described above, while the other of the pair is a deflation valve, that allows the chambers to be deflated. Accordingly, when the relative pressure between expandable member 10em1 and 10em2 reaches a predetermined threshold, where the pressure in 10em1 is less than the pressure in 10em2 by at least the predetermined threshold pressure differential, the deflation valve 38 between chamber 10em1 and chamber 10em2 opens to begin deflating chamber 10em2. Similarly, when the relative pressure between expandable member 10em2 and 10em3 reaches a predetermined threshold (which may be the same or different from the predetermined threshold relative pressure difference between 10em1 and 10em2), where the pressure in 10em2 is less than the pressure in 10em3 by at least the predetermined threshold pressure differential, the deflation valve 38 between chamber 10em2 and chamber 10em3 opens to begin deflating chamber 10em3.

Optionally, a catheter, or guidewire or the like (not shown) can be inserted through adjustment member 80 and conduit 12, and through one or more valves 38 to physically opening the valves for inflation or deflation of one or more chambers.

Figure 19A:
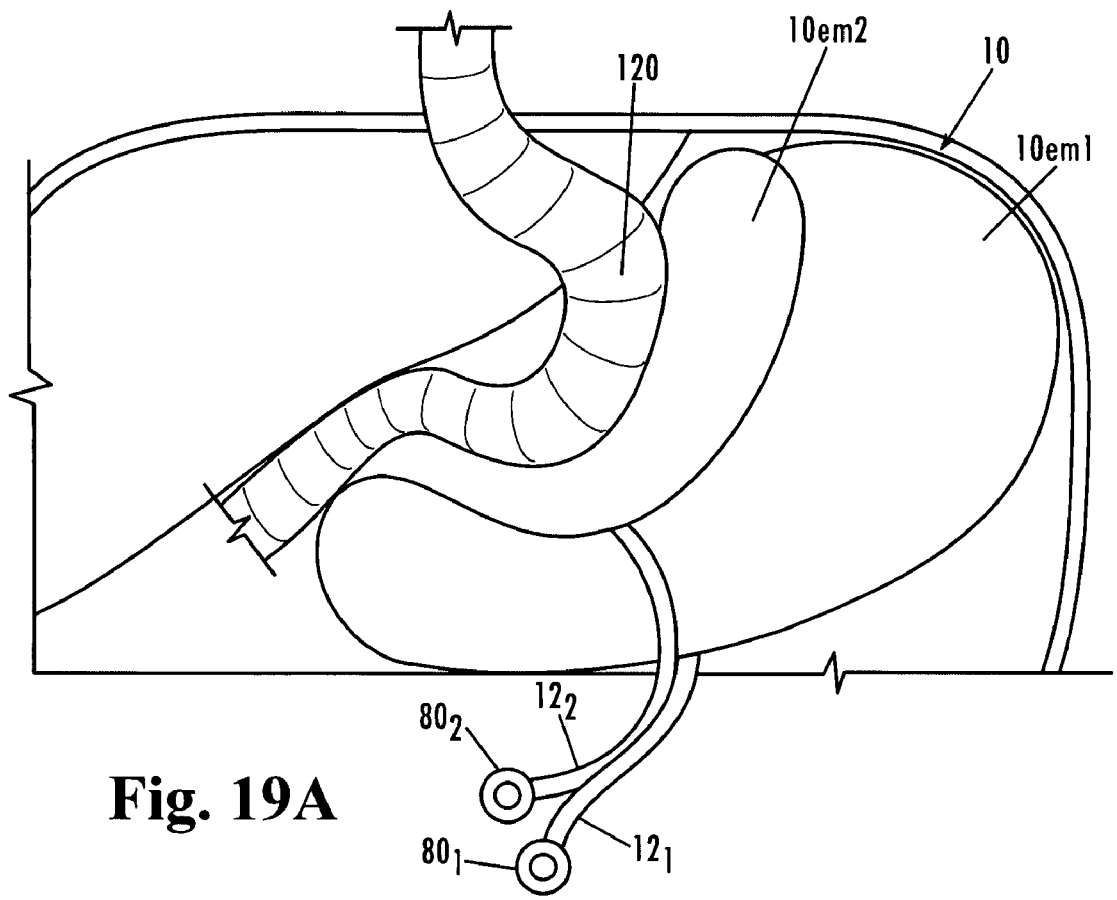
FIG. 19A illustrates a device similar to that described above with regard to FIG. 17A, but wherein expandable member 10em2 has a different shape/conformation.

FIGS. 19A-19E are various views of another embodiment of a hybrid device 10 according to the present invention. FIG. 19A illustrates a device 10 similar to that described above with regard to FIG. 17A, but wherein expandable member 10em2 has a different shape/conformation. Expandable member 10em1 is noncompliant and thus has a fixed size/volume when it is completely filled. Expandable member 10em1 is typically filled with gas, but could alternatively be filled with liquid or liquid and gas. Expandable member 10em2 is compliant and therefore its volume/displacement can be adjusted by adding or removing pressurized medium thereto/therefrom. Typically, expandable member 10em2 is filled with a fluid and adjusted by the amount of fluid inputted thereto. Alternatively, expandable member 10em2 can be filled with liquid and gas, or gas alone, although the compliancy of expandable member 10em2 will typically allow gas leakage/seepage, so that adjustment or "topping off" of the expandable member 10em2 with gas may be required on a periodic basis. This is not the case when expandable member 10em2 is filled with liquid. FIG. 19A shows device 10 implanted in the abdominal cavity in a target location where it restricts the ability of the stomach 120, and particularly the fundus and central portion of the stomach 120, from expanding beyond a predetermined amount. From this view, it can be seen that by increasing the volume of inflation medium to expandable member 10em2, this will increase the displacement thereof, further restricting the amount of space that the stomach 120 is allowed to occupy. Conversely, if the amount of inflation medium is reduced, the stomach will be allowed to expand more than before. The volume of expandable member 10em1, and thus the displacement thereby, is fixed, as noted above.

Figure 19B:
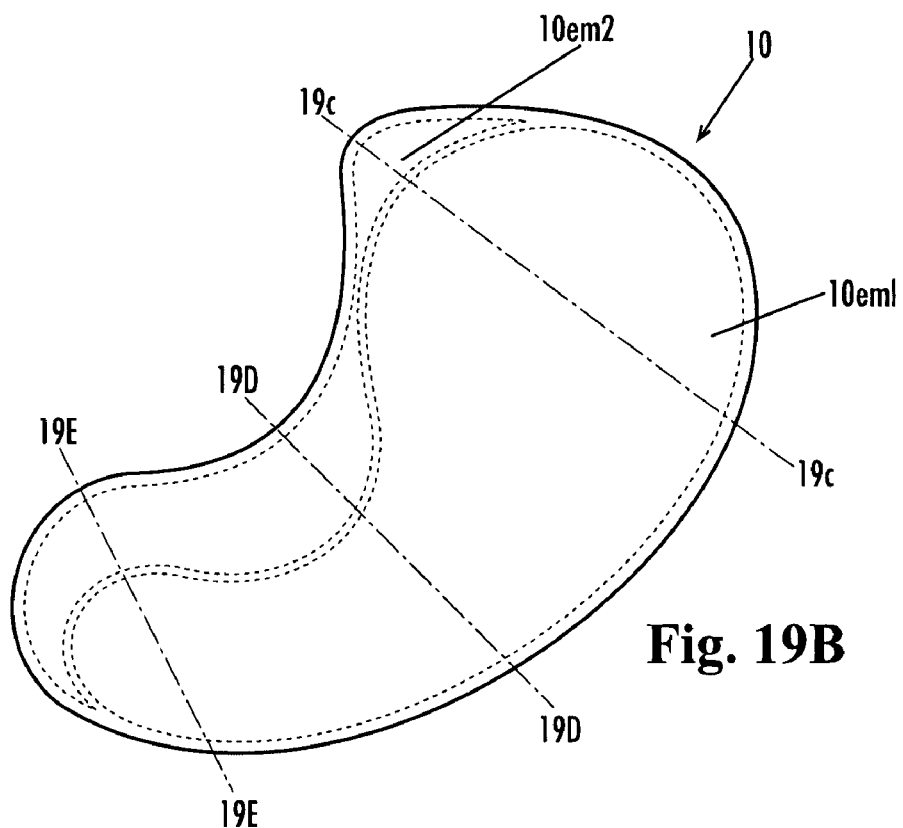
FIG. 19B shows a view of the device of FIG. 19A showing the walls of the expandable members.
Figure 19C:
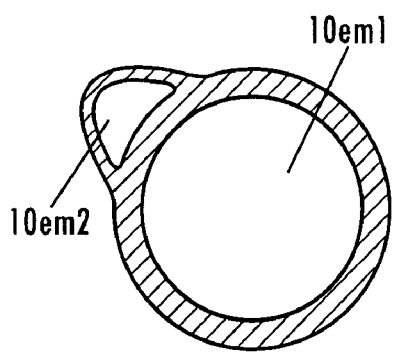
FIGS. 19C-19E are cross-sectional views of the device of FIG. 19B taken along lines 19C-19C, 19D-19D and 19E-19E, respectively.
Figure 19D:
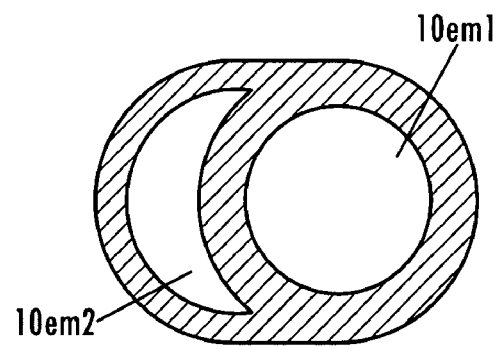
Figure 19E:
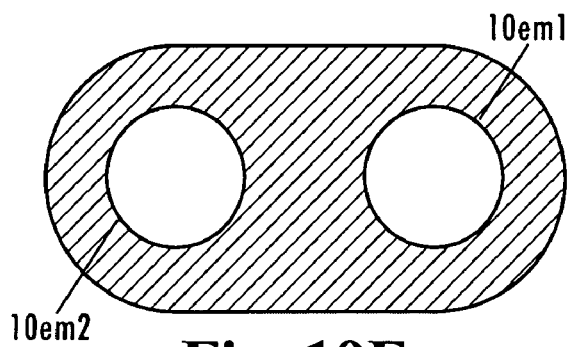

FIG. 19B shows a view of the device of FIG. 19A showing the walls of the expandable members. The conduits $12_1$, $12_2$ and adjustment members $80_1$, $80_2$ are not shown in this view for clarity of the view of the sizes of the expandable members relative to one another. FIGS. 19C, 19D and 19E are cross sectional views of device 10 of FIG. 19B taken along lines 19C-19C, 19D-19D and 19E-19E, respectively, to better illustrate the variability of the cross sectional areas of the expandable members 10em1 and 10em2. At FIG. 19C, expandable member 10em2 is configured to protrude from expandable member 10em1 prominently to engage the Angle of His location of the stomach 120. At FIG. 19D, expandable member 10em2 contours concavely at the interface of the stomach 120 to engage the greater curvature of the stomach 120. Expandable member 10em2 has a relatively large volume at this location to prevent a signification amount of expansion by the stomach 120 at this location, as the stomach 120 can typically expand greatly in this area. At FIG. 19E, expandable member 10em1 is significantly reduced in cross-sectional area compared to FIG. 19D, and expandable member 10em2 is configured to engage the stomach 120 near the pylorus.

Expandable Member Construction

The inflatable members of the inflatable devices described herein can include compliant, noncompliant or semi-compliant materials, or any combination of these. Examples of compliant materials suitable for use in an inflatable member as described herein include, but are not limited to: silicone, latex rubber, and polyurethane. Examples of useable semi-compliant materials include, but are not limited to: nylon, polyethylene, polyester, polyamide and polyurethane, see for example, U.S. Pat. No. 6,500,148, which is hereby incorporated herein, in its entirety, by reference thereto. Polyurethane, nylon, polyethylene and polyester can be compliant or semi-compliant materials, depending upon the specific formulation and hardness or durometer of the material as produced. Examples of noncompliant materials that can be used in the construction of inflatable members described herein include, but are not limited to: polyethylene terephthalate (PET) and urethane. Urethane can be a compliant, semi-compliant or non-compliant material depending upon its specific formulation and hardness or durometer. Compliant, semi-compliant and noncompliant categories are not solely material limited, but are better defined by their expansion characteristics, as noted above. Some materials are best suited for use in one of these categories (e.g., silicone and latex work well to make compliant structures), but other materials can be formulated and/or constructed to provide compliant, semi-compliant or noncompliant properties.

The expandable member 10em of device 10 can have a soft and atraumatic outer surface to prevent damage to nearby organs and structures. In at least one inflatable embodiment, expandable member 10em must be able to hold carbon dioxide ($CO_2$) gas without significant leakage. Silicone is one example of a compliant material that can provide the desirable soft and atraumatic outer surface of an expandable member, and is desirable due to its mechanical properties as well as its successful history as a long term implant material. However, silicone is somewhat porous and thus may not be ideal to hold $CO_2$ gas, even at low pressures. Accordingly, the inner surface of an expandable member 10em having an outer silicone layer can have a lining or coating which has minimal gas permeability, as described in further detail below. Such a lining can be provided in the form of a dual layer or multilayer construction, where the layers are covalently bonded to each other by co-extrusion, co-molding, solvent bonding, dip coating, spray coating, etc. or to where the two or more layers are independent of each other, allowing relative movement.

The inflatable member 10em of a device 10 can be constructed primarily of a compliant material such as silicone, for example, in which case, the expandability of the inflatable member is substantially isotropic, so that the inflatable member expands outwardly by equal amounts in all directions. Alternatively, the wall thickness of the inflatable member can be varied so as to vary the expansion characteristics of the inflatable member, to tailor its expansion properties to a desired performance. As one example of this, the wall including surface 10p can be formed thicker than the wall including surface 10a. In this instance, upon inflation, surface 10a will expand outwardly by a greater distance than surface 10p. A device 10 having a substantially flat surface, such as the one shown in FIG. 3M, for example, can have a thicker wall that includes the flat surface 10p, relative to the wall that includes the surface 10a. Further complexities can be introduced into the expansion properties of an inflatable member by varying the thickness of the wall along the same surface. For example, in a football shaped device, the central portion of the wall that includes surface 10a can be formed thinner than the end portions of the wall that includes surface 10a. As will be readily apparent, numerous variations in wall thicknesses at various locations can be designed to provide a custom expansion profile. Additionally, the provision of a thicker wall adds strength to the device 10. For example, by making the wall containing surface 10p relatively thicker, this provides added support for maintaining the device in contact with an internal structure in the abdominal cavity, and for maintaining some integrity to the shape of the inflatable member.

Another technique for producing an inflatable member with a customized expansion profile includes forming the inflatable member from a combination of two or more of a compliant material, a semi-compliant material, and a non-compliant material. For example, the end portions 10e of device 10 can be made from a semi-complaint material or noncompliant material, while the central portion 10c can be made of a compliant material. In this way, end portions 10e expand less than central portion 10c when device 10 is inflated. Additionally, especially when a noncompliant material is used, ends 10e provide greater lateral support in contacting the wall of the stomach, and are less deformable than if made of a compliant material. The portions of the inflatable member that are formed of different materials can be co-molded together, or bonded together using adhesives and/or solvents, or heat sealed to provide an integral inflatable member as illustrated in the devices of FIGS. 3A-8B, for example. Volume of a device is increased by stretching or deforming in response to a force or pressure, such as by inputting a fluid into the inner cavity defined by the device. In addition to the non-expanded shape and size of the expandable member of the device prior to inputting fluid, volume can also be influenced by the compliance of the material used to make the expandable member, as well as the wall thickness of the material used to make the expandable member. As another example, end portions 10e can be formed of a material that is less compliant (e.g., noncompliant or semi-compliant) than the material that central portion 10c is formed of. For example, portions 10e can be formed of polytetrafluoroethylene (PTFE) or PET, and central portion 10c can be formed of silicone, or other compliant material. Alternatively, end portions 10e can be solid and thus noncompliant. End portions 10e can be joined to central portion 10c by solvent bonding, heat bonding, adhesives, etc. End portions 10e can be in fluid communication with central portion 10a, or they can be independently inflatable through a second lumen, as described above. In this arrangement, end portions 10e remain substantially in their present configuration, and thereby maintain an intended distance therebetween to fit the perimeters of the stomach wall as intended, while central portion 10a expands to deform the stomach wall inwardly.

Further alternatively, end portions 10e can be integral with and in fluid communication with one another, and wrap around the surface 10p of central portion 10c. This construction provides even greater structural rigidity in the end members, since they are interconnected or integral with a portion made from the same noncompliant (or semi-compliant) material. End portions 10e can be in fluid communication with central portion 10c so as to be inflated via the same input lumen. Alternatively, end portions 10e can be independently inflatable. The integral end portions can be glued or otherwise fixed to central portion 10c. As another alternative, the end portions (and/or the piece integrally connecting them) rather than being inflatable, can be foam filled, or solid polymer.

When inflating an inflatable member with a pressurized gas, some materials, especially the compliant materials such as silicone and the like, may have an inherent porosity that may not adequately maintain a desired pressure within the membrane or wall of the inflatable member over an extended period of time. This seepage or slow leakage of gas from the inflatable member may require a patient to have the implant checked more frequently then required for other physiological concerns, to ensure that it is maintaining adequate pressure and thus is expanded to the extent desired to perform the desired amount of deformation of the stomach. One way of eliminating or substantially reducing such seepage is to coat an inner or outer surface of the inflatable member with a "gap-filling" substance, such as a gel or an oil, to fill in and seal the porosity of the material used to form the inflatable member.

Another way of eliminating or substantially reducing such seepage is to provide an inner liner inside the wall of the inflatable member. FIG. 20A illustrates an inflatable member 10em of device 10 having an inner liner 14 that is less porous that the outer membrane 13. As shown in FIG. 20B, liner 14 is made of a material that has less porosity than the outer layer of inflatable material 13 forming inflatable member 10em, that is relatively more porous (see pores 13a). Layer 14 can be bonded to layer 13, or not. One way of bonding layer 13 to layer 14 is to overmold layer 13 on liner 14. In one example, layer 13 is formed from silicone and layer 14 is formed from polyurethane. In another example, layer 13 is formed from silicone and layer 14 is formed from polyester. Of course, other materials can be substituted for layers 13 and 14 to perform similar functions. Outer layer 13 should be inflatable, and relatively non-porous, with outer surface characteristics suitable for contacting the stomach and other structures in the abdominal cavity. In this regard, silicone and other relatively soft, elastic materials provide good atraumatic interfaces. The inner liner 14 should be less porous than the outer layer, and can be compliant, semi-compliant or non-compliant.

An example where inner liner 14 is separate from outer layer 13 is illustrated in FIG. 11. In the example shown, liner 14 is a relatively non-compliant or semi-compliant layer relative to compliant layer 13. The view of FIG. 21 shows expandable member 10em of device 10 in an inflated configuration. The walls of liner 14 are wavy, and may have folds and creases, as the fully expanded liner 14 can be designed to be as large or larger than the outer layer 13. In this way, outer layer 13 can begin to stretch without fully inflating the inner layer 14. For example, in a partially expanded configuration, neither layer is stretched. As fluid is inputted into the expandable member, the outside layer 13 becomes stretched prior to fully inflating the inner layer 14, as shown in FIG. 21. This may be sufficient expansion of the device, depending upon the application. The device can be further expanded so that the walls of layer 14 no longer have folds or creases therein, as layer 13 expands still further under the greater pressure applied. If layer 14 is semi-compliant, it can even be stretched somewhat under increased pressure. As a polymeric layer expands and its wall becomes thinner, the seepage rate through the layer of a gas under pressure increases. Since the inner layer is not stretched (or stretched very little), or is essentially non-permeable, it retains its maximum ability to prevent seepage therethrough, while, at the same time, the outer layer 13 becomes fully expanded and smooth for interfacing with the structures in the abdominal cavity.

For example, layer 14 can be made from polyurethane and layer 13 can be made from silicone, although substitutes for each layer can be made, as already noted. Further, even by forming layers 13 and 14 both from a compliant material such as silicone, some reduction in seepage rates is achieved.

FIGS. 22A-22B illustrate another approach to reducing or minimizing the seepage rate through an inflatable member. FIG. 22A illustrates expandable member 10em of inflatable device 10 in a compact, deflated configuration, wherein no or a minimal amount of inflation medium exists within the inflatable member 10em. Upon inflation of device 10, the inflatable member is inflated only up to a maximum pressure before the wall 13 begins to elastically deform. Because the wall 13 does not elastically deform, the inflated device of FIG. 22B maintains the same porosity and seepage performance that it had in the deflated configuration, as opposed to elastically deforming the inflatable member, which may increase the seepage rate, as discussed above. The wall thickness and or material for constructing the inflatable member of device 10 in this situation can be chosen so that the maximum pressure before elastic deformation is sufficient to fill a space into which the stomach would normally expand if the device were not placed there, and to prevent the stomach from expanding into the space. In one embodiment, in order to occupy the space to prevent the stomach from expanding into the space, device 10 is inflated, but not to elastic deformation, and positioned adjacent the stomach to fill a volume of space that device 10 then prevents the stomach from expanding into. Alternatively, device 10 can be made from a compliant material and configured to fill the space when in an elastically deformed configuration.

Figure 23A:
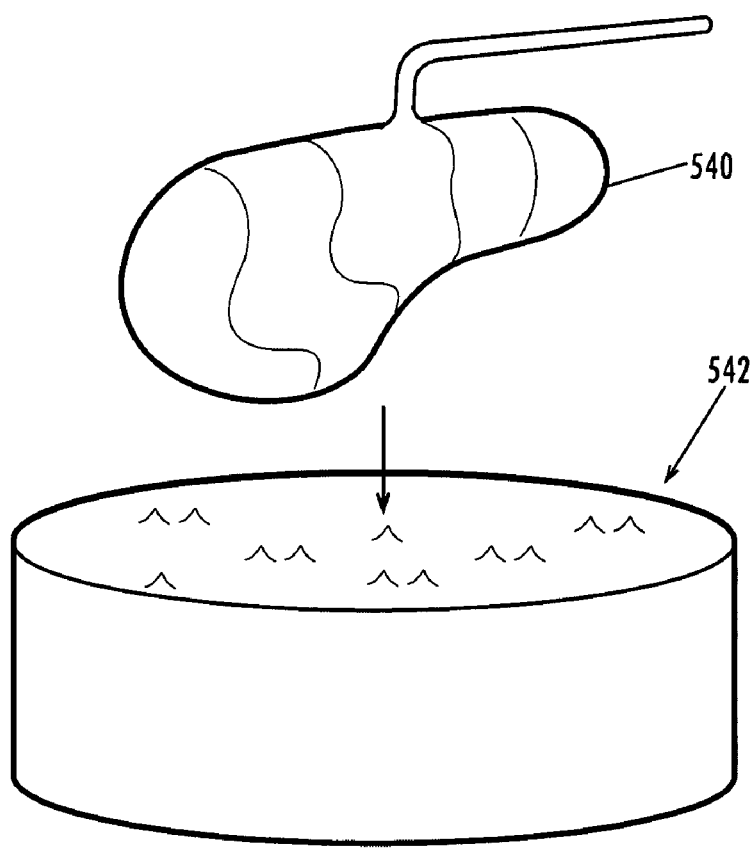
Figure 23B:
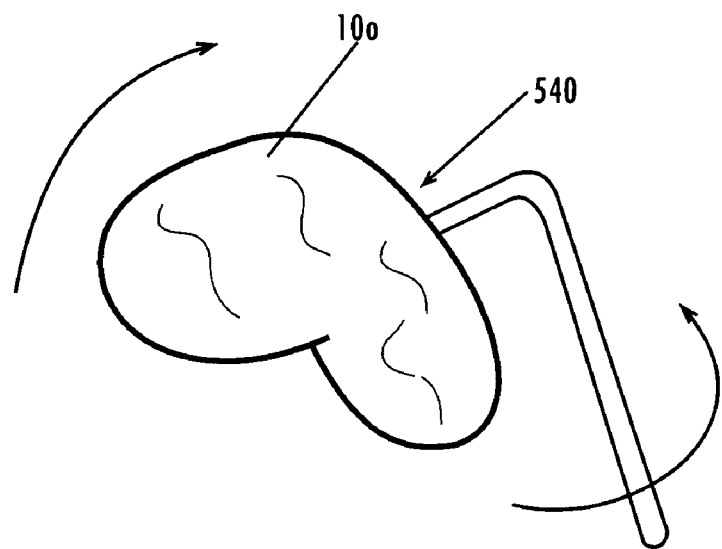

FIGS. 23A-23H illustrate one approach to fabricating a dual layer inflatable member 10em for device 10. The outer layer 10o is preferably formed from a compliant, relatively soft polymer to provide an atraumatic interface with the stomach wall. For example, outer layer 10o can be silicone, latex rubber, or other soft, compliant elastomer. FIGS. 23A-23C illustrate one method of manufacturing outer layer 10o. A mold 540 that has an outer surface conformation that is what matches the desired conformation of outer layer 10o is dipped into a vat 542 of liquid polymer of the material that layer 10o is to be formed of. After a predetermined time, mold 540 is pulled out of vat 542 and agitated to equally distribute the polymer layer that has accumulated on the mold, while the polymer cures or solidifies, see FIG. 23B. The steps in FIGS. 23A and 23B can be repeated until layer 10o has obtained the desired wall thickness. Other materials and/or structures (such as fiber reinforcement, anchoring structures, etc.) can be optionally molded into the layer 10o by placing such materials or structures on the outer surface of the polymer accumulated on the mold, between dips, and then dipping and agitating for one or more repeated cycles.

After finishing the cycles of steps 23A and 23B, and after sufficient curing, the layer 10o is cut from mold 540, such as by cutting a slot or opening 10s1 aligned with the shaft 541 that extends from mold 540 and peeling layer 10o from the mold 540, as illustrated in FIG. 23C. Opening 10s1 is dimensioned to permit the passage of an inner layer therethrough, in a manner as described below. Outer layer 10o, as removed from mold 540, is illustrated in FIG. 23D. In the example shown in FIG. 23D, opening 10s1 is a slot that generally extends between ends 10e. The inner layer can be formed of a somewhat less compliant material, such as a semi-compliant or noncompliant material. In the example shown in FIG. 23E, inner layer 10j is formed from polyurethane. A conduit 12i configured to connect with conduit 12 is provided that extends from and is in fluid communication with inner layer/liner 10j. Inner layer 10j may be less porous than outer member 10o, for reasons discussed above, and is inflatable to expand member 10j. However, inner liner 10j may or may not be elastically deformed when inflating device 10 to its expanded configuration, while outer layer 10o typically will be elastically deformed upon inflation of device 10 to an expanded configuration. Alternatively, device 10 can be inflated to an expanded configuration where neither inner liner 10j nor outer layer 10o are elastically deformed or stretched.

FIG. 23F shows element 16 that can be used to integrate the two inflatable layers 10j and 10o. In the example shown, element 16 comprises a silicone strip having a conduit 12 that connects with an opening through the strip. To further enhance the impermeability of the completed inflatable member 10em, element 16 may be made from a semi-compliant or noncompliant material (e.g., polyurethane, in this example) and coated on the external surface with a compliant material such as silicone or the like, or dip-coated so that the strip is completely encased with the compliant material. Optionally, element 16 may be fiber-reinforced, and include anchoring elements as taught in application Ser. No. 11/407,701 with reference to FIG. 13G in that application. For device 10 to be deployed through a small opening in the stomach wall, however, element 16 will typically be designed to be as flexible as possible, such as by being formed from a compliant material, or semi-compliant or non-compliant material coated with a compliant material, as described above. Further optionally, element 16 may be made from a semi-compliant or non-compliant strip and not coated with a compliant material.

Figure 23G:
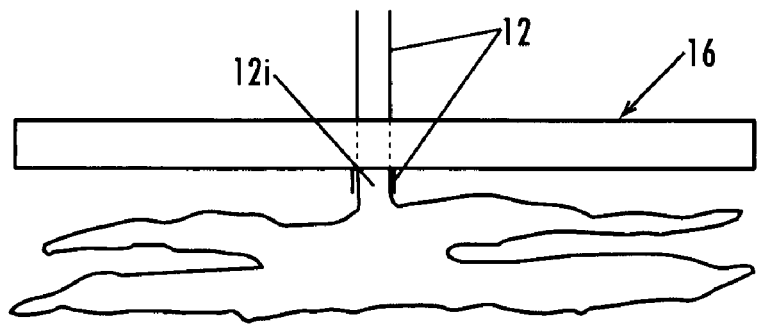
Figure 23H:
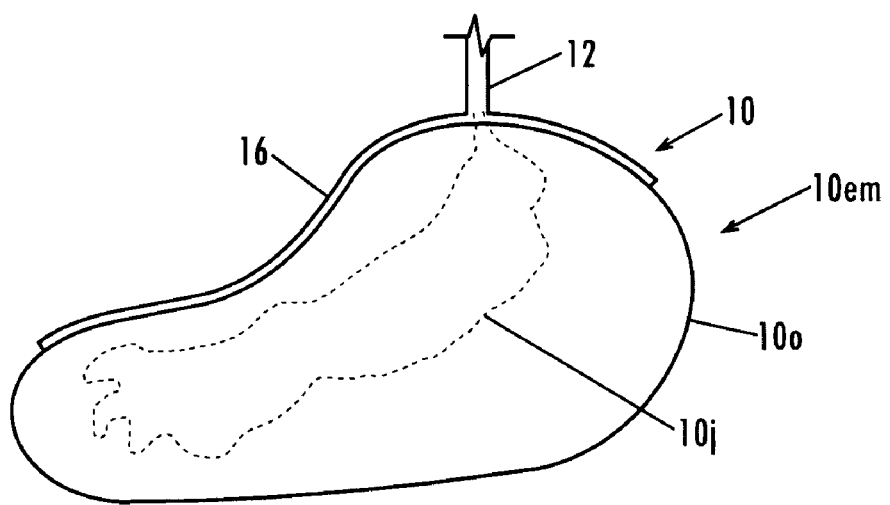
Figure 23I:
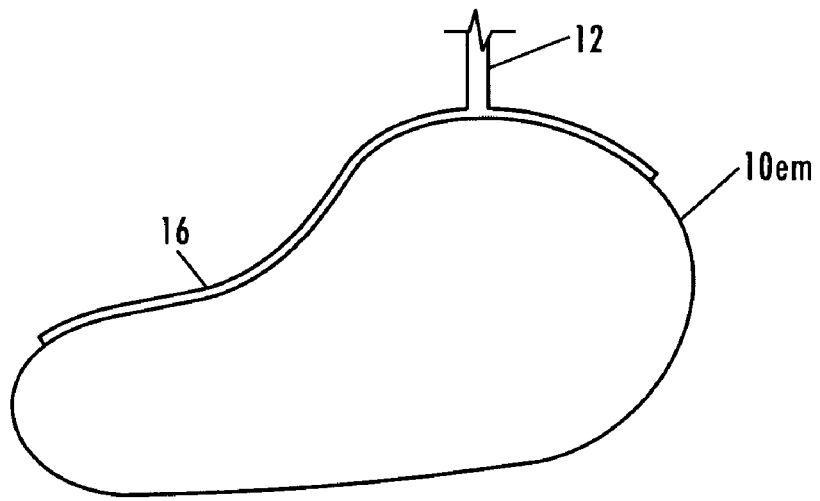
FIG. 23I illustrates a single layer inflatable member manufactured according to one method embodiment described herein, including steps described with regard to FIGS. 23A-23E.

Conduit 12 extends proximally from reinforcing element 16, with also a distal end (not shown) opening from a bottom surface 16b thereof that is configured to be in fluid communication with conduit 12i. To assemble the inflatable member, conduit 12i is connected in fluid communication with the distal end of conduit 12 and sealed, such as by a pressure or friction fit and/or adhesives. Inner inflatable member is deflated to a compressed configuration, and may be further compacted by folding or scrunching the walls together, as illustrated in FIG. 23G. Next, inner inflatable member 10j and conduit 12i are inserted through opening 10s1 and element 16, which overlaps opening 10s1, is adhered over opening 10s1 to seal the outer member 10o so that an enclosed, inflatable space that is substantially leak-proof to fluid and/or gas under pressure results. The resulting inflatable expandable member 10em is illustrated in FIG. 23H. Although the above steps have been described with regard to manufacturing a dual layer inflatable member, it is noted that a single layer inflatable member can be manufactured similarly. Also, an inner layer of a dual layer inflatable member can be manufactured using techniques as described with regard to FIGS. 23A-23C, for example. To manufacture a single layer inflatable member, the layer generated by steps shown in FIGS. 23A-23C is then sealed with an element 6, as illustrated in FIG. 23I. In any of these embodiments, element strip 16 can be prefabricated to incorporate fixation structures (e.g., anchors), conduit 12, internal valve structures for controlling pressure within expandable member 10em via conduit 12 and/or radiopaque markers.

Figure 24A:
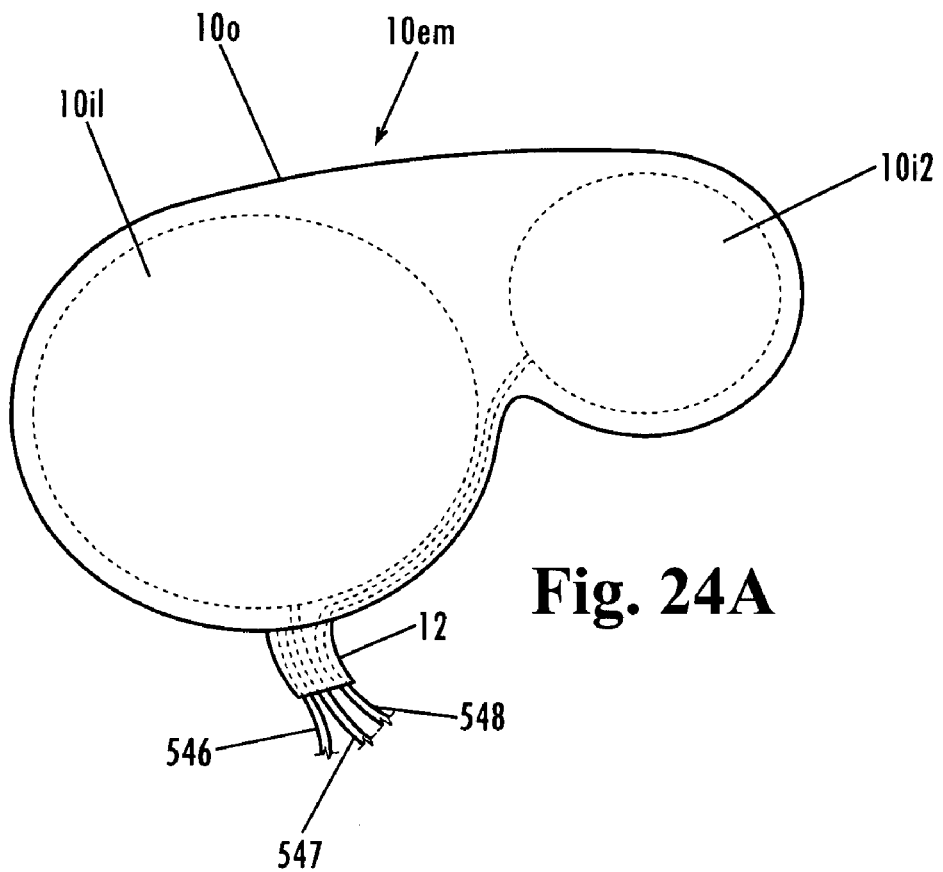
FIG. 24A illustrates an expandable member that is provided as a dual layer expandable member, wherein an outer layer surrounds both inner inflatable elements, each of which are independently inflatable.

Expandable member 10em can be configured to have more than one independent inflatable member or chamber. For example, FIG. 24A illustrates expandable member 10em that is provided as a dual layer expandable member, wherein outer layer 10o surrounds both inner inflatable elements 10i1 and 10i2, each of which are independently inflatable. In the embodiment shown, each of members 10o, 10i1 and 10i2 is independently inflatable via dedicated inflation tube 546, 547 and 548 that pass through conduit 12 and connect to the three respective inflatable members, respectively. This allows differential expansion of expandable member 10em. For example, if more displacement of the stomach 120 is desired in the area contacted by member 10i1 and outer member 10o than what is desired in the area contacted by member 10i2 and outer member 10o, then member 10i1 can be inflated to a higher volume than member 10i2 to effect more movement by member 10i1. Also, it is noted that similar functionality can be obtained in a single layer arrangement, for example, like that shown, only without the outer layer 10o. In such an arrangement, members 10i1 and 10i2 would still be independently inflatable. Members 10i1 and 10i2 can be connected together, for example using fixation structures and techniques described herein or in any of application Ser. Nos. 11/407, 701, 11/716,985 and 11/716,986, to prevent the members from migrating away from one another.

Figure 24B:
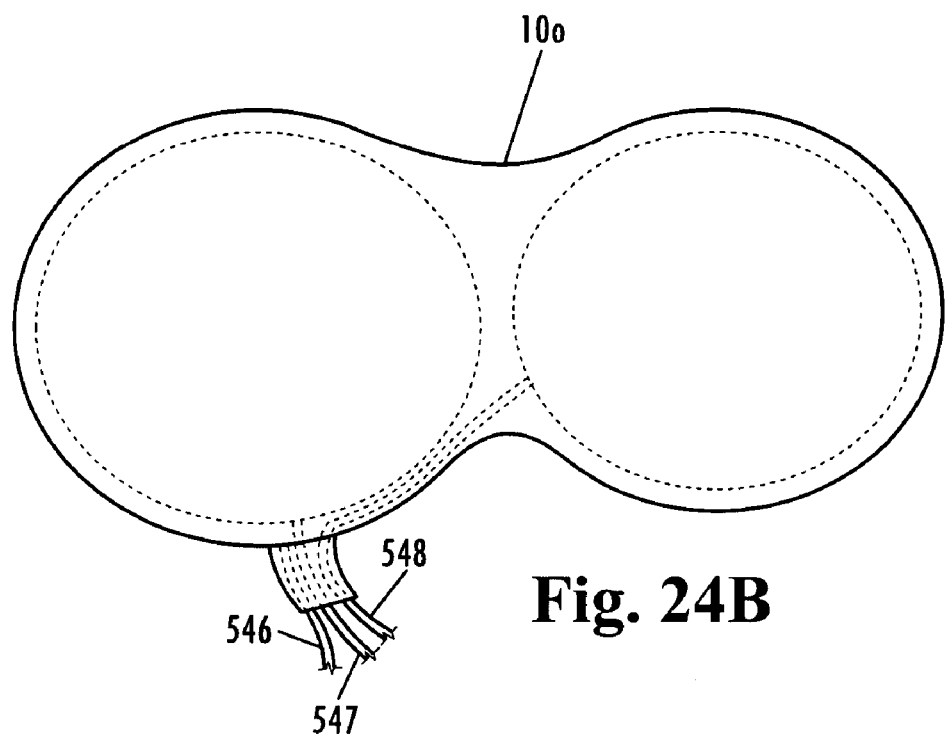
FIG. 24B illustrates an example where the expandable member of FIG. 24A has been resized.

FIG. 24B illustrates an example where the expandable member 10em of FIG. 24A has been resized (such as by reducing the volume in member 10i1 and/or increasing the volume in member 10i2) so that the members 10i1 and 10i2 are approximately the same size.

Reinforcing elements 16 can be configured to provide a more rigid frame or structure to maintain the inflatable member in a desired orientation or configuration when inflated and when applying forces to the stomach. The reinforcing elements can be arranged to provide a relatively rigid "exoskeleton" or "endoskeleton" of the inflatable member, as described in further detail in application Ser. No. 11/407,701.

Surface Features

The external surfaces of devices 10 are designed to provide atraumatic, non-irritating interfaces with the internal structures in the abdominal cavity that are to be contacted with. Surface 10a, designed to interface with the stomach wall, can be smooth and designed to reduce friction therewith. Similarly, surfaces 10p can be designed to abut another internal structure, such as the diaphragm, abdominal muscles, or other structure, and can be designed to be smooth and to reduce friction between the device surface and the internal structure. These smooth features, as with other surface features described herein, can be designed into the existing surfaces of the device, or can be provided by attaching an additional layer to a portion of the surface of the device where the feature is desired. For example, smooth, non-frictional surfaces can be provided by the surface of the balloon material of an inflatable device, or by polishing metallic struts of a mechanically expanding device and/or radiusing edges thereof. Alternatively, all or a portion of a surface can be coated with a low friction material, e.g., PTFE, hydrogels, covalently-bonded lubricant or jelly, etc., or can be modified so that the surface has a microporous, sponge-like quality able to microabsorb body fluids and thereby create a low friction surface. A porous polymeric layer can be coated over all or a portion of a device surface and impregnated with a lubricious material, such as hydrogels, for example.

Figure 25:
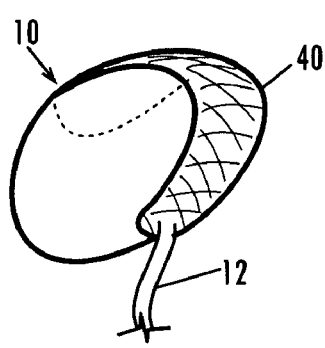
FIG. 25 shows an example of a device having a backing or patch to provide additional structural integrity to a portion of the device.
Figure 26:
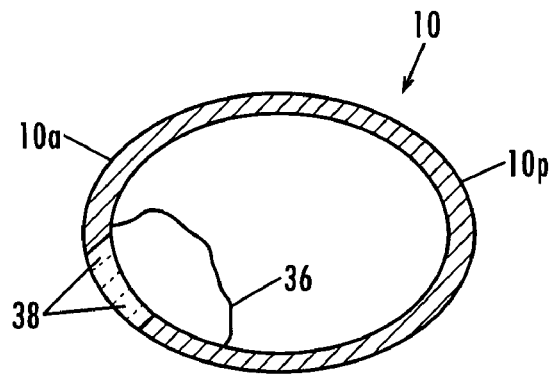
FIG. 26 illustrates a device provided with a reservoir.

In addition to providing a low friction surface, reduction of irritations and/or prevention of adhesions with hydrogels, linked surface polymers, phosphorylcholine, or other treatments can be provided by a treatment- or drug-eluting coating 40 over all or a portion of a device surface, as illustrated in FIG. 25. Additionally, at least the portion of conduit 12 that contacts tissue may be coated with coating 40. Such a coating 40 can be impregnated with a substance to be diffused out of the coating over time, or can be provided with other known time-release mechanisms. Examples of substances that can be provided in such a coating include, but are not limited to: anti-obesity drugs, other drugs for treating co-morbidity that can be associated with the patient's obesity, antiproliferative drugs such as rapamycin, TAXOL®, MYCITAXOL®, or the like; heparin; anti-inflammatory drugs such as ibuprofen, acetaminophen or aspirin; steroidal anti-inflammatories such as fluticasone, mometasone, triamcinalone, prednisone, methylprednisone or the like; other non-steroidal anti-inflammatory drugs; and/or pain medications, such as lidocaine, bupivicaine, etc. Additionally, or alternatively, device 10 can be provided with a reservoir 36 (as illustrated in FIG. 26) to hold one or more of the treatment substances just described. Treatment substances can be delivered to the surface of device 10 through one or more pores or channels 38 via diffusion, or by an active drug delivery pump of a type currently known in the art, which can be configured for continuous or intermittent timed release of the substance.

Figure 27:
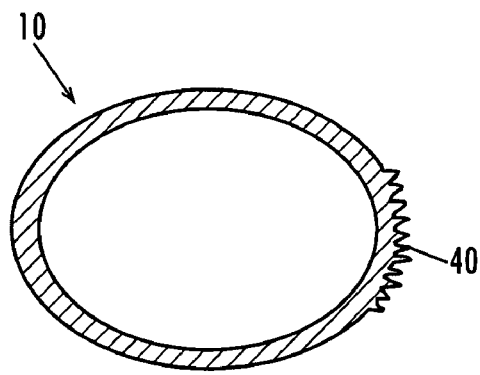
FIG. 27 illustrates a device having a roughened surface portion.

Referring to FIG. 27, one or more surface portions can be roughened, or made to have increased porosity, relative to the remainder of the surface, to increase friction when contacted with an internal structure to help prevent migration of device 10 and/or to promote a healing response and subsequent ingrowth of tissue into the roughened or porous surface to function as an anchor of the device, as also described below with regard to anchoring. Such roughened or increased porosity surface can be formed into the surface of inflatable device 10, as shown in FIG. 27, or can be formed by attaching an additional layer of material to the surface, such as a fiber-reinforced silicone patch, a patch of fiber-lined polyester, a patch of a material that is more porous than the porosity of the surface of the device, or other layer configured to provide the desired characteristics. In addition to providing a roughened, more porous, and/or drug eluting function, a backing or patch 40 can also provide additional structural integrity to a portion of device 10 to reduce the amount of expansion of that portion of the device relative to the remainder of the expandable body. Further, backings, patches or reinforcing layers 16, 40 can be used to reinforce attachment of other structures to the expandable device, such as anchors for example. One or more locations on the surface of a device 10 can also be configured to be radiopaque, as described in more detail below.

Anchoring

Figure 28:
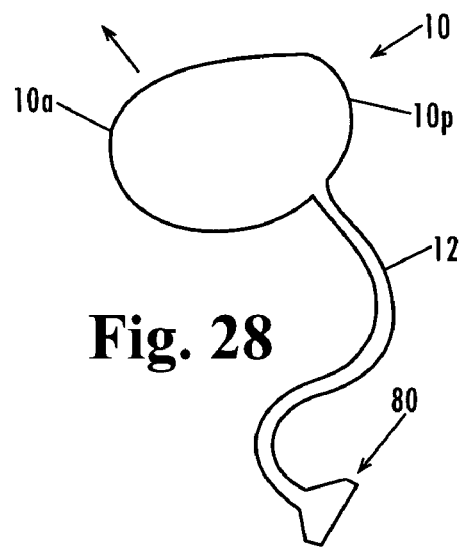
FIG. 28 illustrates a device and shows an expandable member conduit and adjustment member of the device.

In some embodiments of the present invention, device 10 is anchored via expansion forces of the expandable member 10em against the internal stomach wall lining. Additionally, the conformation of expandable member 10em of these embodiments can provide a mechanical type of anchoring, wherein the inferior end portion of expandable member 10em is too large to pass further inferiorly within the stomach or into the intestines. Additional fixation members may also be applied. In some embodiments where device 10 is an extra-gastric device, device 10 may be primarily anchored relative to the stomach 120 via conduit 12 that passes through the wall of the stomach. In other extra-gastric embodiments, it may be desirable to allow the stomach and other organs in the abdominal cavity to move relative to device 10. With regard to the extra-gastric embodiments, it may be desirable to anchor device 10 relative to at least one internal body structure to prevent migration of the positioning of device 10. FIG. 28 illustrates a device that can be used according to some extra-gastric method embodiments described herein, with expandable member 10em including surfaces 10a and 10p, and an adjustment member 80 (described in further detail below) including an inflation port, wherein adjustment member 80 is in fluid communication with the expandable member by conduit 12. Conduit 12 is typically flexible and can be made from any of the polymeric materials described above for making the inflatable, expandable member 10em, which can also be used to make conduit 12 in embodiments where conduit 12 passes through the wall of the stomach 120. Typically silicone or reinforced silicone can be used. In any case, conduit 12 is constructed to be flexible and kink-resistant, and for connection to an inflatable, expandable member, to have low or no permeability to pressurized fluids to be used to inflate expandable member 10em. Further, in this embodiment conduit 12 is formed to have sufficient length to interconnect the expandable member with adjustment member 80 when the expandable member is positioned in a target surgical area within the abdominal cavity, adjacent the stomach and in an expanded configuration, and when adjustment member is positioned outside of the abdominal cavity, typically fixed to the abdominal muscles, externally of the abdominal cavity, or in some other subdermal location outside of the abdominal cavity. In these situations, anchoring of adjustment member to the abdominal wall or other location external of the abdominal cavity can prevent migration of the expandable member in a direction indicated by the arrow in FIG. 28, although this is typically not the case, since conduit 12 is not typically designed as a tether and is intended to be left slack when the expandable member is properly positioned and adjustment member is anchored. In any event, conduit 12 will not prevent migration of the expandable member in any other direction, including downwardly, which can be a direction that the expandable member can be urged to migrate by forces such as peristaltic activity of the stomach, gravity, etc. Accordingly, adjustment member 80 and conduit 12, in the arrangement described, without further fixation, do not provide an anchor. However, other arrangements are described herein where conduit 12 (and optionally, an adjustment member) can be arranged to anchor the expandable member 10em.

In order to prevent or minimize the potential of migration, it is desirable to anchor the expandable member 10em in at least one location to an internal structure in the abdominal cavity. Anchoring techniques described below can be carried out by themselves, or in combination with one or more other anchoring techniques described. As noted above, one way of providing an anchor is to provide a roughened surface or surface of increased porosity to increase friction between the expandable member and the internal structure it is contacting and/or to promote tissue ingrowth. Additionally or alternatively, adhesives can be applied to one or more surfaces of the expandable member of device 10 to be fixed to one or more internal structures. Additionally or alternatively, adhesives can be applied to the surface(s) of the internal structure(s) where contact by the device is to be made for anchoring device 10 thereto. Adhesives can be applied to such structures via a conduit inserted into the abdominal cavity from a location external of the patient, wherein adhesives can be flowed or sprayed onto such structures.

Another anchoring mechanism can be provided by placement of one or more suction members 44 on the surface of the expandable member of device 10 (an example of which is shown in FIG. 30 of application Ser. No. 11/407,701). Alternatively, one or more suction members 44 can be fixed to the internal structure (such as by suturing, hooks, adhesive, etc.) to which the expandable member is to be anchored. Suction members may be suction cups, although other configurations of suction producing features can be substituted as suction members (e.g., members having elongated suction chambers, etc.).

Figure 29A:
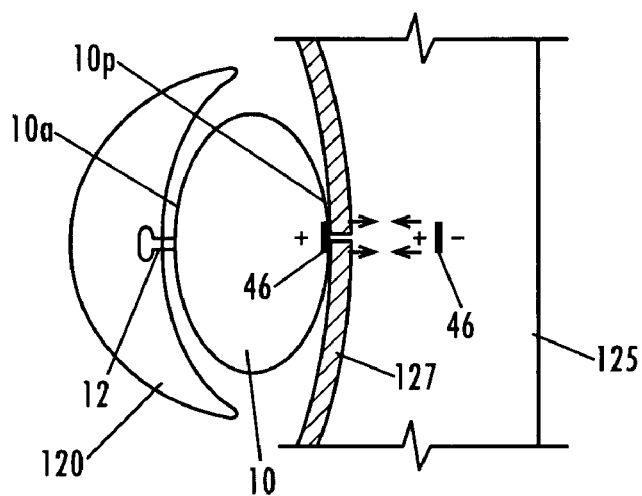
FIG. 29A illustrates that anchoring can be performed using one or more pairs of magnets oriented to attract to one another.

FIG. 29A illustrates that anchoring can be performed using one or more pairs of magnets 46 oriented to attract to one another. In the example shown in FIG. 29A device 10 is anchored to an internal surface of the abdominal wall or abdominal muscle by fixing a first magnet to surface 10p of the expandable member of device 10, while fixing another magnet 46 subcutaneously in a position to align with the other magnet 10 at a location where surface 10p is desired to be anchored, and with opposite poles of the magnets 46 facing each other. It will be readily understood that more than one pair of magnets can be arranged to establish the anchoring. The magnets can be fixed by adhesives, suturing, or other alternative fixing means. When the expandable member includes a polymeric surface, magnet(s) 46 can be molded into the polymeric wall of the expandable member, or fixed to the internal surface of the polymeric wall. Further alternatively, the magnet(s) 46 opposing the magnet(s) 46 on the expandable member can be fixed to the opposite wall of the structure (i.e., outside of the abdominal cavity) to which device 10 is to be anchored (e.g., the external wall of the abdominal muscle in this example), embedded within the internal structure to be anchored to, or fixed to the skin, on the internal side of the skin layer.

Figure 29B:
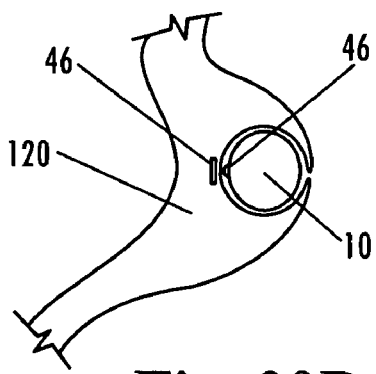
FIG. 29B illustrates anchoring a device to the stomach wall using one or more pairs of magnets.

Further alternatively or additionally, surface 10a of device 10 can be anchored to the stomach wall using one or more pairs of magnets 46, as illustrated in FIG. 29B. Magnet(s) can be attached to the stomach wall either on an internal surface of the wall, external surface of the wall, or embedded between layers of the wall. Magnet(s) 46 can be fixed to the wall of device including surface 10a in any of the manners described above with regard to attaching magnet(s) to the wall of device 10 that includes surface 10p.

The conduit 12 interconnecting the expandable member 10em and adjustment member 80 of device 10 can be configured to anchor the expandable member to an internal structure, such as the stomach 120, for example, as shown in FIG. 29A, with or without additional fixation structures as described. In the example illustrated in FIG. 29A, the expandable member of device 10 is anchored against the external surface of the stomach 120, by fixing conduit 12 against the internal layer of the stomach via adjustment member 80. Additionally, this example shows magnetic anchoring of surface 10p. Alternatively, or additionally, other forms of additional anchoring may be provided as described herein. Further alternatively, device 10 may be anchored solely via the anchoring of conduit 12 that passes through the stomach wall. Conduit 12 can be reinforced, especially in the location between the fixation to the stomach wall, such as by connection of adjustment member 80 thereto, to withstand being maintained under tensile forces to anchor the expandable member. Reinforcements can include fiber reinforcement, steel or polymer meshes or coils, etc.

FIG. 30 illustrates device 10 using a combination of attachment/anchoring features. The superior end portion of device is indicated by 10s, the inferior portion by 10i and the anterior surface of the device is indicated by 10a. Device 10 of FIG. 30 is configured to be inserted intra-abdominally, such that the left lobe of the liver 121 is positioned anteriorly of, and contacts the liver attachment patch 40l, and attachment patch 40a contacts the anterior abdominal wall. These patches 40a, 40l are configured to encourage tissue ingrowth and thereby anchor device 10 to the anterior abdominal wall and the left lobe of the liver. Additionally, an attachment flange or fin 150f extends around at least a portion of the surface 10p of the expandable member 10em of device 10, and extends tangentially therefrom, thereby being configured to be placed in contact with the anterior abdominal wall and lateral abdominal wall (and, optionally a portion of the diaphragm 116) for attachment thereto.

The outwardly directed surface of attachment flange 150f may be provided with a roughened/tissue ingrowth enhancing surface 150fr (e.g., polyester felt or mesh, or the like) while the inwardly directed surface 150fs that is not intended to contact and anchor to a structure is smooth, such as smooth silicone, for example, such as high tear strength silicone, e.g., NUSIL 6400 silicone, or the like. Attachment tabs 150 may be made of high tear strength silicone, e.g., NUSIL 6400 silicone, or the like, and extend from flange 150f to facilitate further anchoring by stapling, tacking, suturing, gluing, etc. these tabs to one or more internal structures. Additionally, or alternatively, stapling, tacking, suturing and/or gluing, etc, can be performed on or through the flange 150f itself.

When implanted, device 10 overlies (i.e., lies anteriorly of and in contact with) a portion of the stomach 120, the inferior portion of attachment flange 150f is attached to the anterior abdominal wall, with the intermediate and superior portions of the attachment flange 150f being attached laterally to the abdominal wall and to a portion of the diaphragm 116. Attachment pad 40a abuts the anterior abdominal wall and, over time, tissue ingrowth occurs, thereby anchoring patch 40a to the anterior abdominal wall. Similarly, the left lobe of the liver overlying and contacting patch 40l results in tissue ingrowth into patch 40l, thereby anchoring it to the liver 121.

FIGS. 31A-31C illustrate various stapling patterns that may be employed for stapling an attachment flange 150 or attachment tabs 150 to one or more internal body structures for anchoring device 10/expandable member 10em. Although the patterns shown are for application of staples to perform anchoring, the same patterns can be applied for anchoring by suturing, and/or tacking, which may also be in combination with stapling and/or any of the other fixation/anchoring means described herein. In FIG. 31A, multiple staples 150s (rows of two staples each, as shown, although three or more staples may be used, per row) are provided in rows that extend radially outwardly from expandable member 10em, through attachment tab(s)/flange 150. The rows are separated by substantially equal distances 150d, about two to three cm, as shown. In FIG. 31B, multiple columns of staples 150s are provided (two columns as shown, although three or more columns may be provided). These columns generally follow the contour of the attachment tab(s)/flange 150 and/or the surface of the expandable member 10em that the attachment tab(s)/flange is connected to. In FIG. 31C, reciprocal patterns of staples 150s are used. In the top two patterns shown, staples 150s are arranged in a cross pattern. In the bottom two patterns shown, staples 150s are arranged in a box pattern. Alternative reciprocal patterns may be employed, such as triangular, circular, etc.

Figure 32A:
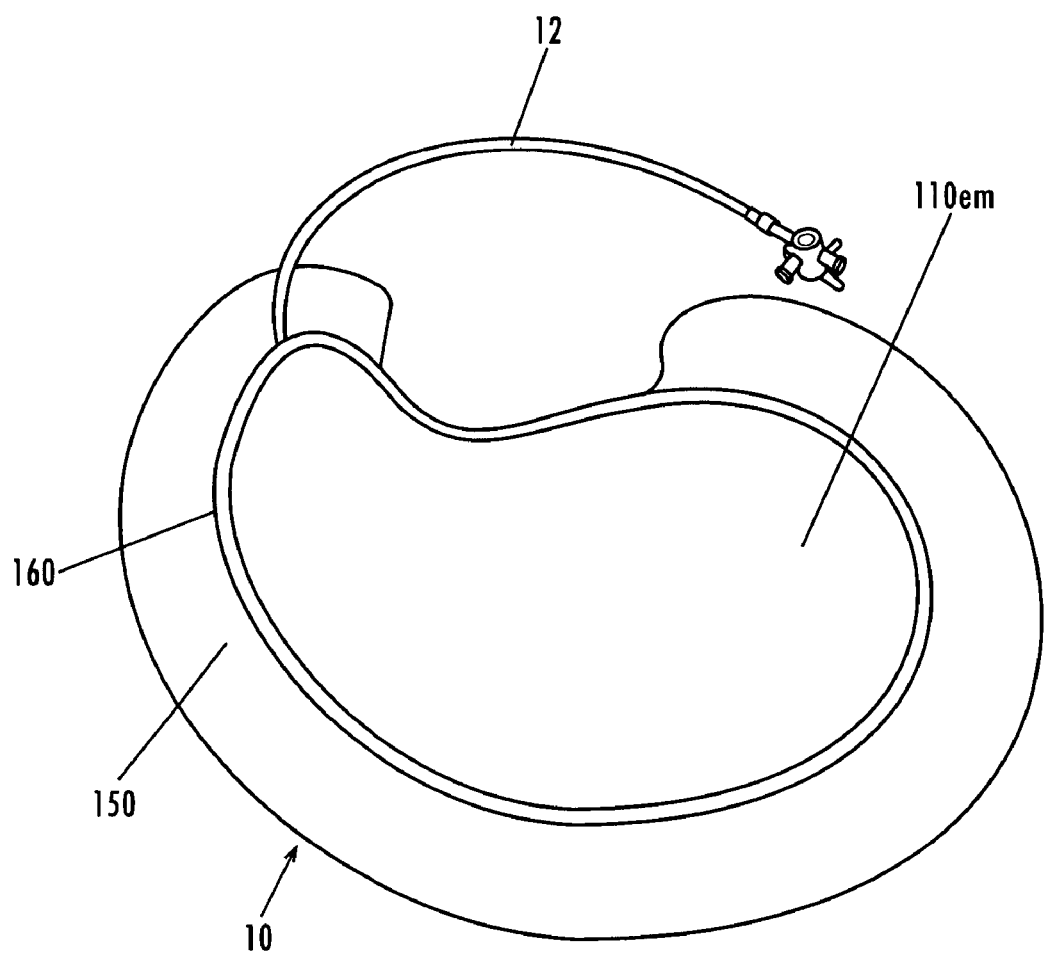
FIGS. 32A-32B illustrate a device in a deflated configuration and an inflated configuration, respectively, in which an attachment flange has been integrated into the weld seam of the expandable member.
Figure 32B:
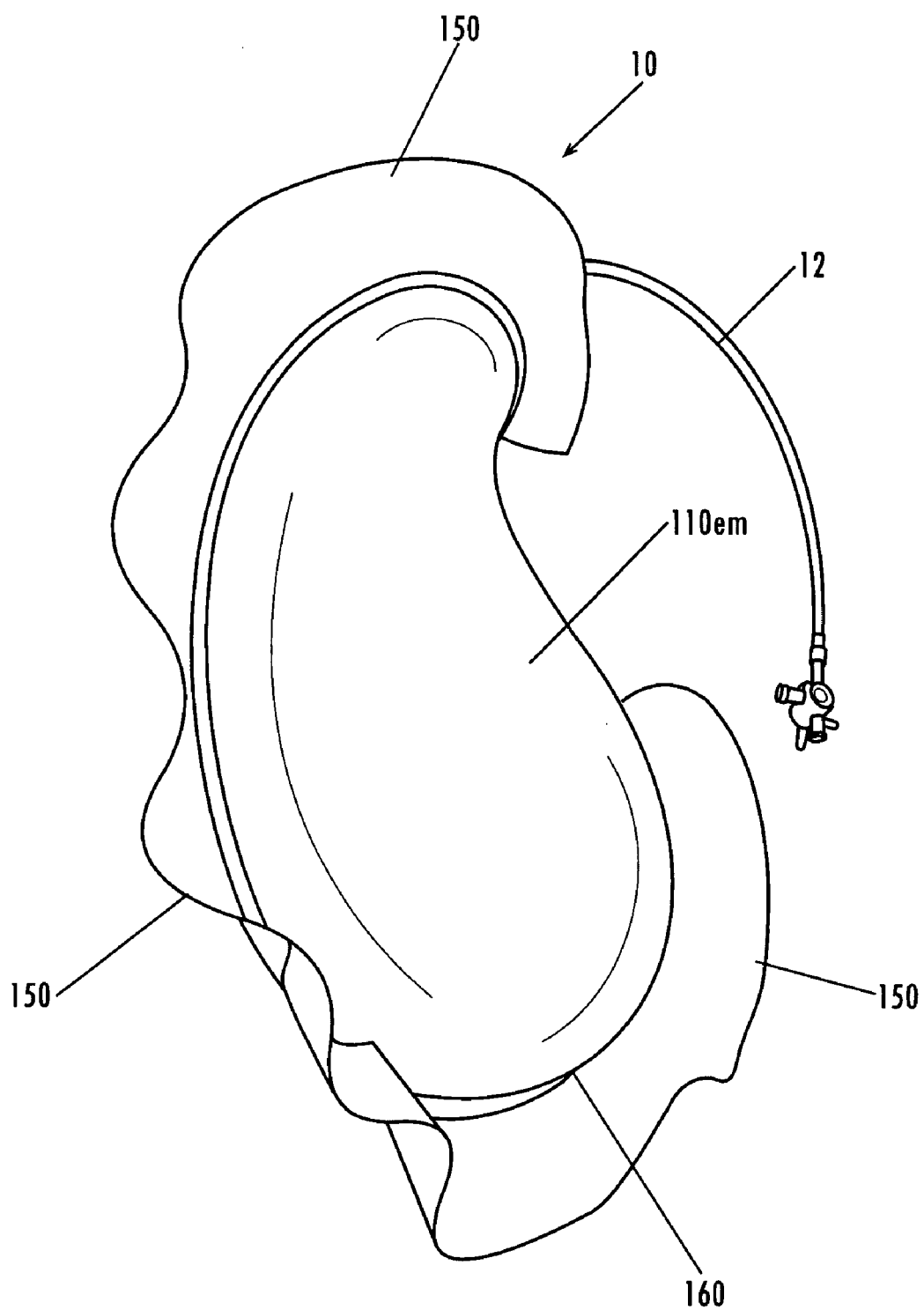

FIGS. 32A-32B illustrate a device 10 in a deflated configuration and an inflated configuration, respectively, in which attachment flange 150 has been integrated into the weld seam 160 of the expandable member. In the example shown, expandable member 10em is formed of a metallized, compliant material, examples of which are described in more detail in application Ser. Nos. 60/877,595 and 11/716,985, both of which were incorporated by reference above. Accordingly, rather than bonding attachment tab(s) or attachment flange 150 to the outer surface of the expandable member 10em. When an expandable member is formed by welding two portions together (such as by thermal bonding, RF energy weld, etc.), a peripheral portion of the attachment tab(s)/flange 150 is positioned between the peripheral portions of the walls of expandable member 10em to be welded together, thereby sandwiching the attachment tab(s)/flange(s) 150 between the expandable member layers and bonding all together during the welding process. In the example shown, the expandable member walls are of a polyurethane base material, with a metallic coating (e.g., titanium or the like) thereover, which is then dipped in silicone. However, integration of one or more attachment tabs 150 and or attachment flanges 150 can be performed in the same manner described above when performing a weld seam during forming an expandable member comprised of materials other that those described with regard to the example shown. Further, this sandwiching technique is particularly advantageous in instances when an external silicone dip layer is not needed or used over the expandable member material.

Figure 33A:
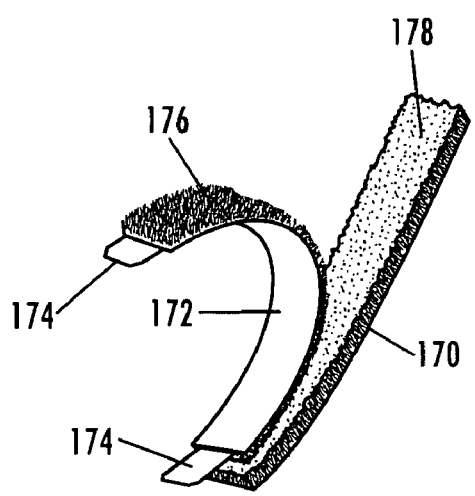
FIGS. 33A-33B illustrate different views of another attachment mechanism that can be employed for anchoring a device according to the present invention.
Figure 33B:
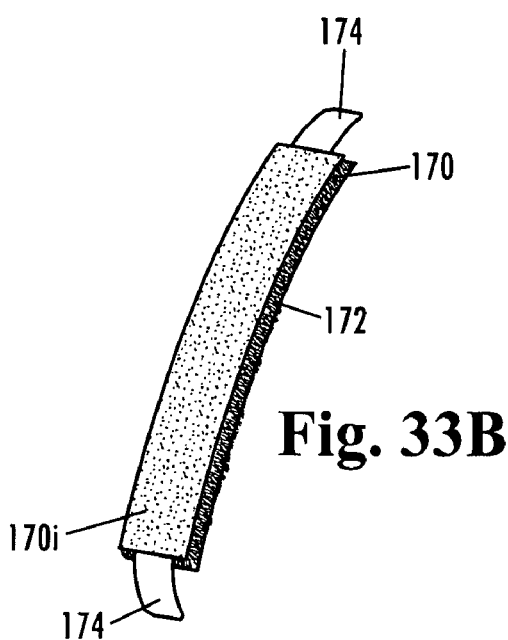

FIGS. 33A-33B illustrate different views of another attachment mechanism that can be employed for anchoring a device 10 according to the present invention. FIG. 33A illustrates an anchor strip 170 that is configured to be anchored to an internal body structure, and protective strip 172 that is configured to be fixed to the fixation surface of anchor strip 170 to protect the fixation surface during anchoring of the strip 170 to an internal abdominal structure, such as the abdominal wall, or other structure, and optionally (typically) during a period to allow tissue ingrowth into surface 170i of strip 170, prior to anchoring device 10 to strip 170. As shown in FIG. 33A, protective strip 172 is only partially fixed to anchor strip 170, as a portion thereof has been peeled away from anchor strip 170, such as by applying tension to tab 174 with sufficient force to break the releasable bonds between the strips 170,172. In the example shown, the releasable bonds are achieved with hook 176 and loop 178 type fastener material. Tabs 174 may be provided at any locations along the perimeter of protective strip 172 and are provided at the ends thereof in the example shown in FIG. 33A. Tabs 174 are features provided for conveniently manipulating the protective strip 172, such as by graspers or the like.

FIG. 33B shows protective strip 172 fully attached to anchor strip 170 with the back, or tissue engaging surface of anchor strip 170 being shown. Thus, FIG. 33B shows the flip side of the arrangement of FIG. 33A. The tissue engaging surface of anchor strip 170 may be provided with a tissue ingrowth material that is roughened, porous and/or otherwise configured to encourage tissue ingrowth. For example, Dacron felt, Dacron mesh or other polymeric woven, felt or material having porosity of a size configured to encourage tissue ingrowth may be used.

Figure 33C:
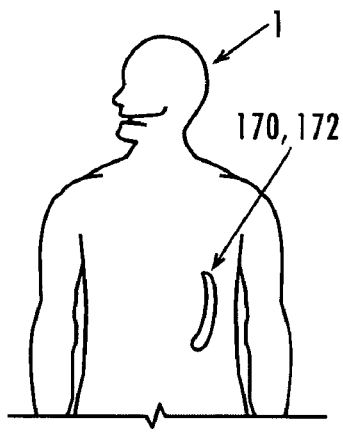
FIG. 33C is an illustration of a partial anterior view of a patient, in which the anchor strip and protective strip shown in FIGS. 33A-33B have been fixed at a left anterior location of the abdominal wall.
Figure 33D:
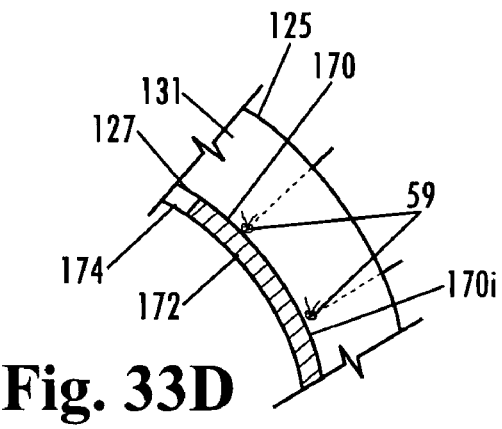
FIG. 33D is a partial, cross-sectional illustration showing the anchor strip attached to the abdominal wall using sutures, and protective strip removably fixed to anchor strip via hook and loop type fasteners.

FIG. 33C is an illustration of a partial anterior view of a patient 1, in which anchor strip 170 and protective strip 172 have been fixed at a left anterior location of the abdominal wall. Anchor strip 170 may be initially fixed to an internal body structure, such as the abdominal wall, for example, using sutures, staples, tacks or other mechanical fixation. FIG. 33D is a partial, cross-sectional illustration showing anchor strip 170 attached to the abdominal wall 127 using sutures 59 and protective strip 172 removably fixed to anchor strip 170 via hook and loop type fasteners. When the tissue engaging surface of anchor strip 170 is placed into contact or near the target site on the abdominal wall 127 where it is to be fixed, graspers or a hooked-needle type of tool (not shown, but this technique is described in more detail in application Ser. Nos. 11/716,985 and 11/716,986) can be inserted through the skin 125, fat 127 and abdominal wall 127 to engage a suture and pull it through the abdominal wall. In order to carry out this technique, sutures 59 may be pre-placed through anchor strip 170 to extend from the tissue contacting surface of anchor strip 170, as illustrated in FIG. 33E. Sutures may be fixed to the strip, with free ends extending therefrom, as shown, or the free ends may be tied together to form a loop. Note that tab features can also optionally be provided on anchor strip 170. When used on either anchor strip 170 or protective strip 172, tabs 174 are typically rounded at their free ends, as shown, to reduce potential trauma that might otherwise be caused by interaction of sharp or acute surface edges with tissue.

After pulling the sutures 59 through the abdominal wall, the sutures are then tied down against the fascia externally of the abdominal wall, thereby holding the anchor strip in contact with the inner surface or the abdominal wall. Subsequently, tissue ingrowth into the tissue ingrowth surface 170i of the anchor strip reinforces the anchoring of the anchor strip 170 to the abdominal wall 127. This tissue ingrowth can be so substantial that the sutures are no longer needed to maintain the strip in place.

Figure 33F:
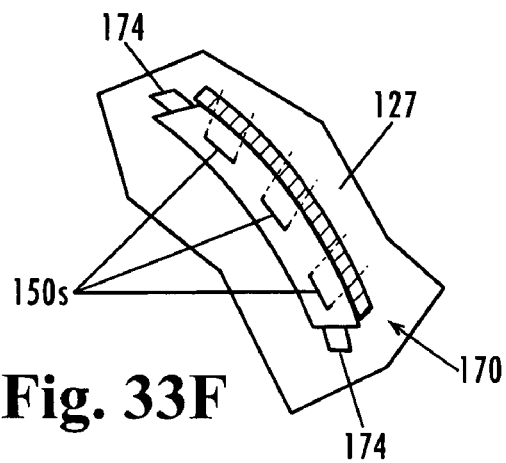
FIG. 33F illustrates use of staples to initially fix the anchor strip to the inner surface of the abdominal wall.
Figure 33E:
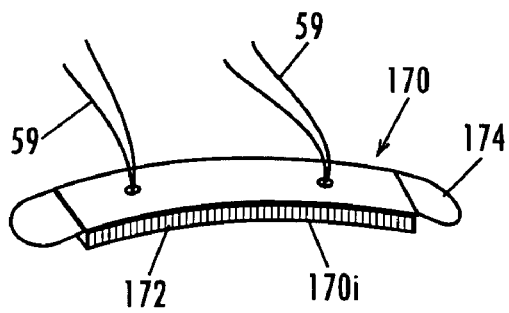
FIG. 33E illustrates sutures having been pre-placed through the anchor strip to extend from the tissue contacting surface of the anchor strip.

FIG. 33F illustrates use of staples 150s to initially fix the anchor strip 170 to the inner surface of the abdominal wall 127. Staples can be driven through the anchor strip 170 and abdominal wall 127 from a location in the abdominal cavity.

Staples can be driven through the protective strip 172 and anchor strip 170 as shown, as protective strip can be removed with sufficient force to cause the staples to pull through the material of the protective strip 172. Alternatively, staples may be driven through the anchor strip 170 to fix it to the internal abdominal structure, and then the protective strip 172 can subsequently be attached to the anchor strip 170. Staples 150s may be preloaded in anchor strip 170, without extending out of the tissue engaging surface of the anchor strip 170, prior to insertion of anchor strip 170 into the abdominal cavity. Alternatively, anchor strip 170 may be first placed into contact with the abdominal wall or other target internal structure to be anchored to, and then staples 150s can be delivered from a stapling tool to drive the staples through the anchor strip 170 and abdominal wall 127.

If the tissue ingrowth surface 170i is provided with a fast reacting tissue adhesive material (such as cyanoacrylate, or the like), initial attachment in this case may not need sutures or staples or any mechanical fixation means, as anchor strip 170 can be adhered to the target internal abdominal structure and held there by the adhesive bonding during the period of tissue ingrowth.

An anchoring strip 179 is fixed to device 10 in a location where it can be used to connect to anchor strip 170, in the same location covered by protective strip 172, after removal of protective strip 172, thereby anchoring device 10 relative to the internal abdominal structure that anchor strip 170 is fixed to. This anchoring of the device 10 is typically accomplished after tissue ingrowth has occurred within the tissue ingrowth surface 170i of anchor strip 170. However, anchoring of device 10 by attaching strip 179 to strip 170 can be performed prior to tissue ingrowth when strip 170 has been adequately secured by mechanical and/or chemical means.

FIG. 33G illustrates removal of protective strip 172 from engagement with anchor strip 170. Graspers 784 in this example are used to grasp tab 174 and, by pulling/retracting graspers away from anchor strip 170, protective strip 172 is peeled away from anchor strip 172 and removed. As noted above, this procedure is typically carried out after sufficient time has passed to allow ingrowth of tissue from the internal abdominal structure (in this example, the internal surface of abdominal wall 127) into the tissue ingrowth material on anchor strip 170. Alternatively, protective strip 172 can be removed from anchor strip 170 in this manner immediately after fixing strip 170 to the internal body structure, such as by mechanical and/or chemical means, or at any time after fixing strip 170 to the internal body structure.

Anchoring strip 179 is fixed to device 10 and anchor strip 170 is fixed to an internal body structure, both in strategic locations that allow anchoring strip 179 to be fixed to anchor strip 170 to position device 10 in the desired location and orientation within the abdominal cavity. FIG. 33H illustrates anchoring strip having been fixed to a surface of expandable member 10em in a location to be placed over and attach to the attachment feature of anchor strip 170, so as to properly place and orient device 10 as intended. Anchoring strip 179 will typically have about the same size and shape as protective strip 172, so as to fix to anchor strip 170 over substantially the same area where protective strip 172 was attached, prior to removal. Thus, if protective strip 172 has the loop portions of the hook and loop type fastening mechanism, then anchoring strip 179 will also have loop portions, but if protective strip 172 has the hook portions of the hook and loop type fastening mechanism, then anchoring strip 179 will also have hook portions.

This same type of anchoring mechanism and techniques described above with regard to FIGS. 33A-33H can also be applied to anchor strips 170, protective strips 172 and anchoring strips 179 having different shapes that those described. For example, FIG. 33I illustrates an anchor pad 170 and protective pad 172 that are substantially circular. In this case, anchoring pad 179 would be provided with a similar size and shape. This configuration increases the attachment area, thereby increasing the strength of the fixation of anchor pad 170 to the internal abdominal structure by tissue ingrowth and/or mechanical and/or chemical fixation, and also increases the strength of the fixation of anchoring pad 179 to anchor pad 170. Multiple tabs 174 are provided on protective pad 172 in FIG. 33I (five shown, although this number may vary). Further alternatively, anchor pad 170, anchoring pad 179 and protective pad 172 may be formed in other shapes and sizes, including oval, hourglass, crescent shaped, irregular, etc.

Further alternatively or additionally, the expandable member of device 10 can be anchored to one or more internal structures by one or more conduits, rods, tethers, or other elongated structure designed to support a sustained tensile force to maintain one or more surfaces of the expandable member anchored against one or more internal structures. Further details of these fixation structures and still other variations of fixation structures that may be employed with the devices described herein are described in application Ser. Nos. 11/407,701, 11/716,985 and 11/716,986.

As indicated above, device 10 can be adhered to the stomach 120 without penetrating the inner surface of the stomach. FIG. 34 shows one embodiment in which device 10, like device 10 shown in FIG. 3N, wherein expandable member 10em may be inflatable, mechanically expandable, or a composite of both, is configured and dimensioned to be wrapped around the stomach, to deform a portion of the stomach inwardly, under the area covered by protrusion 10a' to create a narrow pathway 102w for food to travel through. The effects of this procedure are thus similar to that provided by a sleeve gastrectomy, but without having to surgically remove a portion of the stomach 120, or cut into the stomach 120 or staple the stomach 120. Device 10 can be adhered to the stomach 120 and/or the peritoneum or diaphragm or chest wall or ribs, using a cyanoacrylate-based adhesive or other biocompatible, surgically-approved adhesive. The surface of the device 10 to be adhered to the stomach or other structure can be adhered, for example, by injecting adhesive through a lumen of a multi-lumen port, such as through a lumen in conduit 12 when conduit 12 is provided with multiple lumens, to deliver the adhesive to the surface to be adhered, thereby adhering it to the intended structure. Additionally, or alternatively, device 10 can be anchored using any of the other mechanical fixation members described herein, including cinching belts or straps, and/or inflatable member shapes configured to perform an anchoring function.

Alternatively, device 10 can be shaped to have an anterogastric limb 10an and a retrogastric limb 10r, each of which are inflatable and shaped to match the curvature or follow the contours of the stomach 120. FIG. 35 illustrates a cross-sectional view of such a device 10. Limbs 10an and 10r are interconnected by an intermediate section 10i, all of which can be in fluid communication to provide a single inflatable member, having the appearance of a curved hot dog bun or taco shell. Alternatively, the intermediate section can be a structural member that is not inflatable, but is resiliently biased, which can include spring steel or other resiliently biased structural element(s), to maintain limbs 10an and 10r in a predetermined, juxtaposed configuration. In either case, anterogastric limb 10an, when device 10 is positioned on the stomach, would cover a portion of the anterior surface of the stomach 120, and retrogastric limb 10r would cover a portion of the posterior surface of the stomach 120 in substantially a mirror image of that of the anterogastric limb 10an. Upon expansion, limbs 10an and 10r expand to compress the anterior and posterior wall portions of the stomach together, with the resulting effects as described in FIG. 34. The device 10 of FIG. 35 can be adhered to the stomach 120, as described with regard to the embodiment of FIG. 33, but alternatively, the clamping action of limbs 10an and 10r can function to anchor device 10 with respect to the stomach 120 without the use of adhesives. Further optionally, intermediate section 10i (and/or one or both limbs) can be anchored to an internal structure other than the stomach using any of the techniques and/or fixation structures described herein, or in application Ser. Nos. 11/407,701, 11/716,985 and/or 11/716,986.

Further optionally, one or more resiliently biased members can be incorporated into or around the limbs and intermediate section of device 10. For the arrangement where all sections are inflatable, such resiliently biased members can be molded into the walls of the inflatable member. Resiliently biased members can be biased toward a configuration wherein the limbs 10an, 10r apply compressive force to the walls of the stomach.

It should be further noted that the geometry or shape of the expandable member itself can function as an anchor by engaging or wedging of a portion thereof against an internal structure in the abdominal cavity. For example, device 10 can be anchored by wedging expandable member 10em in a location where it is prevented from easily migrating, due to the size, shapes and locations of the surrounding abdominal organs, In one example, expandable member 10em is expanded to a size large enough to nearly fill the subdiaphragmatic space, so that it becomes wedged between the diaphragm, the stomach, the spleen, the posterior and/or lateral and/or anterior abdominal walls and the aorta, and the pancreato-splenic ligament.

An adjustment member 80 can be connected to the expandable member via a conduit 12, as already described. Although an adjustment member is not necessarily required for a mechanically expandable device, one can optionally be provided to allow reversal of the procedure by collapsing the expanded member using a draw wire or cable attached to the expandable frame, in any of the manners described above, or in application Ser. No. 11/407,701. An adjustment member is not necessarily required for an inflatable device, either, e.g., such as in the case of the self-inflating device described above with regard to FIGS. 8A-8B or in FIG. 4. However, an adjustment member 80 will typically be provided for convenient, repeatable accessibility to adjust the amount of pressure or degree of expansion of the expandable member.

Figure 36:
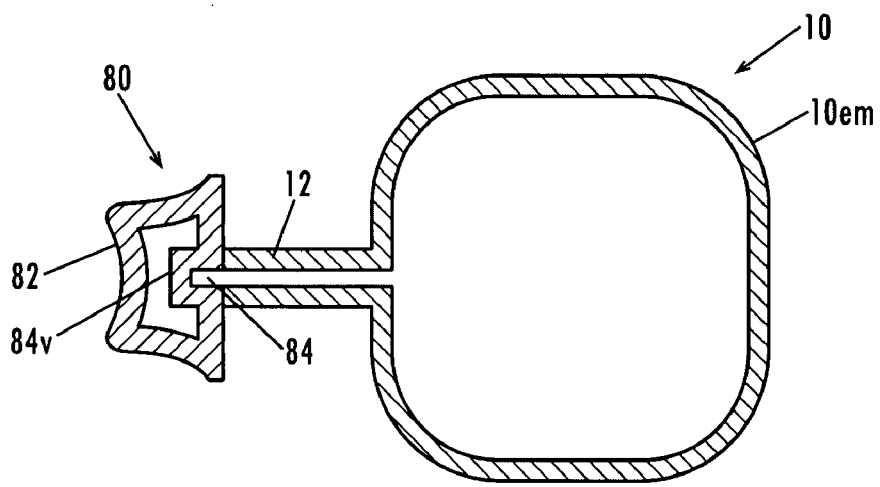
FIG. 36 illustrates a device configured and dimensioned to be anchored to the stomach wall via the adjustment member and conduit connected thereto.

FIG. 36 illustrates a sectional view of device 10 having an inflatable expandable member 10em in fluid communication with adjustment member 80 via conduit 12. Adjustment member 80 includes a port 84 through which fluid such as liquid and/or gas can be inputted into conduit 12 for delivery to the expandable member 10em. A valve mechanism 84v is provided to maintain the pressure within expandable member 10em and to only selectively allow fluid to be inputted to or extracted from expandable member 10em. For example, valve mechanism 84v can be any of a number of well-known mechanical valves. Additionally, an elastomeric seal 82 (e.g., made from "self-sealing" silicone) may be provided to allow entry into port 84 via a needle or other appropriately configured delivery mechanism and valve mechanism 84v.

In order to provide assistance in locating adjustment member 80 and properly align an inflation tool with port 84, various homing mechanisms may be incorporated, as described in detail in application Ser. No. 11/407,701. Adjustment member 80 can be fixed in place by suturing and/or other fixation features, as described above. Alternatively, in embodiments where conduit 12 passes through the wall of the stomach, adjustment member 80 can be fixed by attaching it to conduit 12 so that the surface of adjustment member in contact with the stomach wall and surface 10a of expandable member 10a maintain the relative positioning of device 10 by their respective locations on opposite sides of the stomach wall. Optionally, adjustment member 80 and surface 10a may hold the stomach wall under slight compression when expandable member 10em is expanded. Further details about various configurations of adjustment member 80 that may be employed with the devices described herein, as well as inflation tools and needles that can be used to access adjustment member 80 for altering the amount of expansion or pressure within expandable member 10em are described in application Ser. Nos. 11/407,701, 11/716,985 and 11/716,986.

Intra-Gastric Sizing

Visualization of the deformation of the stomach caused during one or more procedures described herein can be carried out endoscopically, fluoroscopically, ultrasonically, or using some other visualization technology (or can be viewed directly if an open surgical procedure is performed through a large incision), as a measure of how much to expand the one or more expandable members, and consequently how much deformation of the stomach is to be accomplished. Intra-gastric sizing procedures can be carried out alternatively, or in addition to these visualization monitoring techniques to provide the surgeon with a more well-defined, objective feedback regarding when to halt the deformation of the stomach caused by expansion of one or more expandable members, or a tool used to deform the stomach prior to placing one or more expandable members.

Figures 37A, 37B, 37C:
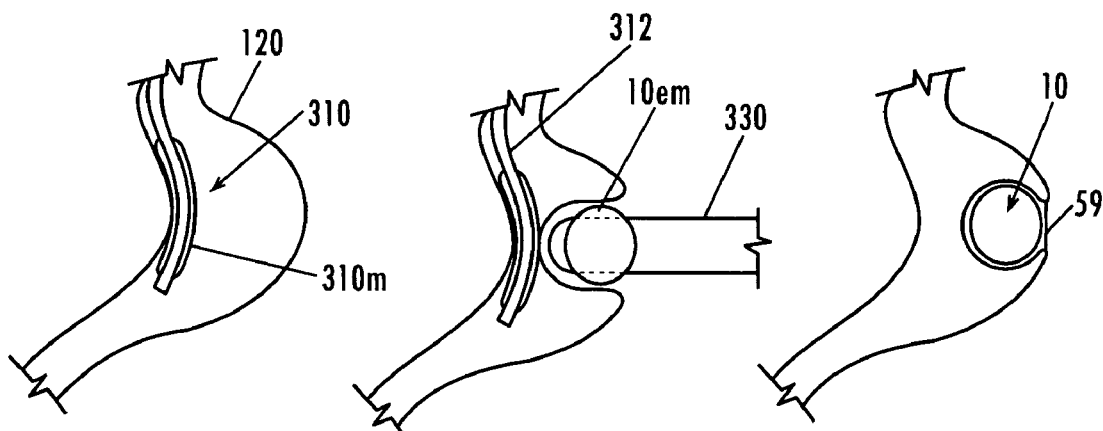
FIG. 37A illustrates placement of an intra-gastric sizing device.
FIG. 37B illustrates gauging or sizing the appropriate amount of deformation of the stomach wall using the intra-gastric sizing device placed in FIG. 37A.
FIG. 37C illustrates completion of implantation of a device using the techniques illustrated in FIGS. 37A-37C.

FIGS. 37A-37C illustrate three stages of a procedure for implanting an extra-gastric, expandable device 10 with the aid of an expandable, intra-gastric sizing device 310. Prior to deformation of the stomach wall, which can be before or after positioning tool 330 (such as an introducer or pusher, for example) having expandable member 10em mounted thereon is introduced to the desired surgical target area, intra-gastric sizing device 310 is passed trans-orally into the patient and advanced until sizing member 310m is positioned within the cavity of the stomach 120, see FIG. 23A. Sizing member 310m is configured to assume a compressed or deflated configuration to facilitate passing it trans-orally and through the esophagus of the patient, and an expanded configuration, as shown in FIG. 37A, having an enlarged cross-sectional area configured to define a dimension of the reduced-volume intra-gastric cavity to be established by deformation of the stomach wall. Sizing member 310m can be inflatable (such as the example shown in FIG. 37A) or mechanically expandable, using any of the construction configurations discussed above with regard to expandable members 10em. Sizing member 310m can be expandable to a predetermined expanded size, or can be adjustably expandable, to vary the cross-section area of sizing member over a range of expanded sizes.

When sizing member 310m has been properly positioned within the stomach as desired, which can be confirmed using visualization techniques, tool 330, with expandable member 10em mounted on a distal end portion thereof, is next pushed against the stomach wall to begin deforming the stomach wall inwardly. Pushing can be continued until it has been visually confirmed that the inner surface of the wall of the stomach 120 that tool 330 is pressing against/contacts sizing member 310m. Alternatively, sizing member 310m can include a pressure sensor that measures the pressure within sizing device 310, particularly when sizing member 310m is inflatable, or one or more strain gauges can be mounted on the surface of expandable member 310m that is to be contacted by the inner surface of the stomach wall, and compression of the stomach can continue in this case until a predetermined amount of pressure or strain has been measured. Further alternatively, sizing member 310m can be provided with a sensor (e.g., an ultrasonic sensor or the like) that can measure the distance between the inner wall surface of the stomach wall and sizing member 310m, wherein pushing by tool 330 can be halted when a predetermined distance between the inner surface of the stomach wall and the sizing member 310m has been achieved.

Upon halting, portions of the stomach wall abutting opposite sides of tool 330 can be maintained in their current positions by joining them with sutures 59 or other connectors to prevent these portions of the stomach from moving away from one another. Then expandable member can be expanded to further deform the stomach superiorly and inferiorly, as illustrated in FIG. 37C. Once expandable member 10em has been expanded to the desired size, as can be confirmed by visualization, tool 330 is removed, leaving the installed device as illustrated in FIG. 37C. Sizing device 310 can be deflated and removed just prior to or after removal of tool 330. Other variations of sizing devices 310 that may be used with this and other procedures described herein are described in U.S. application Ser. No. 11/407,701.

Radiopacity

Figure 38:
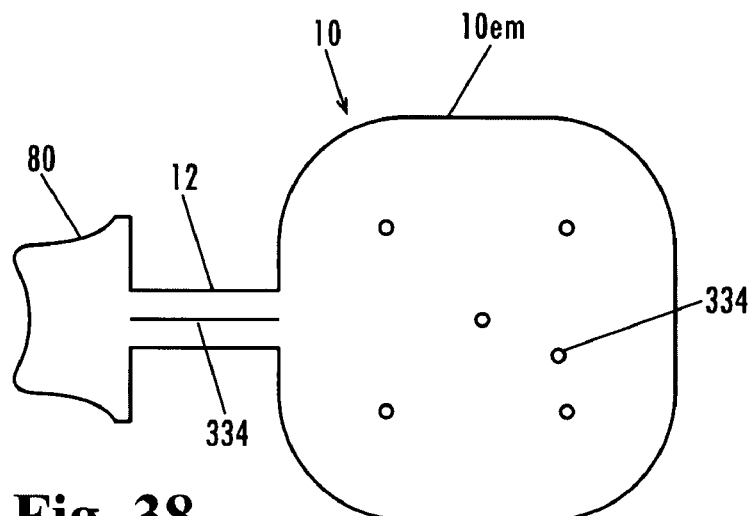
FIG. 38 illustrates a device where at least a portion of the device is radiopaque.

Portions of device 10, as well as device 310 and other devices that are either temporarily or permanently placed within the body of the patient can be provided with radiopaque markers and/or constructed partially or in whole from materials that are radiopaque. "Radiopaque" refers to the ability of the marker or material to be visualized under X-ray visualization. In FIG. 38, the adjustment member 80 is formed partially of metal and can thus be detected radiographically. Conduit 12 can be provided with a radiopaque stripe 334 running the length thereof, bands circling the conduit in a transverse direction to the longitudinal axis of the conduit and/or dots so that the conduit can be visualized under X-ray when the conduit has been placed into the abdominal cavity of a patient. Likewise, expandable member 10em can be provided with radiographic dots, stripes, bands or other marker 334 to indicate the perimeter of the member, whether inflated or not, under X-ray, when placed inside the patient. Expandable member 310m and conduit 312 can be similarly provided with radiopaque markers.

The radiopaque markers can be adhered to the surfaces of the components, or, for polymeric components molded into the polymer of the components. Further, radiopaque contrast agent can be delivered into the cavity of the stomach to visualize the stomach cavity volume under X-ray. As the stomach cavity volume is compressed by one or more expandable members 10em, the reduction in volume of the stomach cavity is readily observed the reduction in the area of the contrast agent visualized.

Methods

In addition to the methods already described above, this section describes details of methods that can be employed to implant the devices described herein. It is to be understood that the methods described herein are only examples of methods that can be employed, as alternative techniques, placement of devices, anchoring of devices, locations or structures to which devices are anchored, etc. can be employed.

Figure 39A:
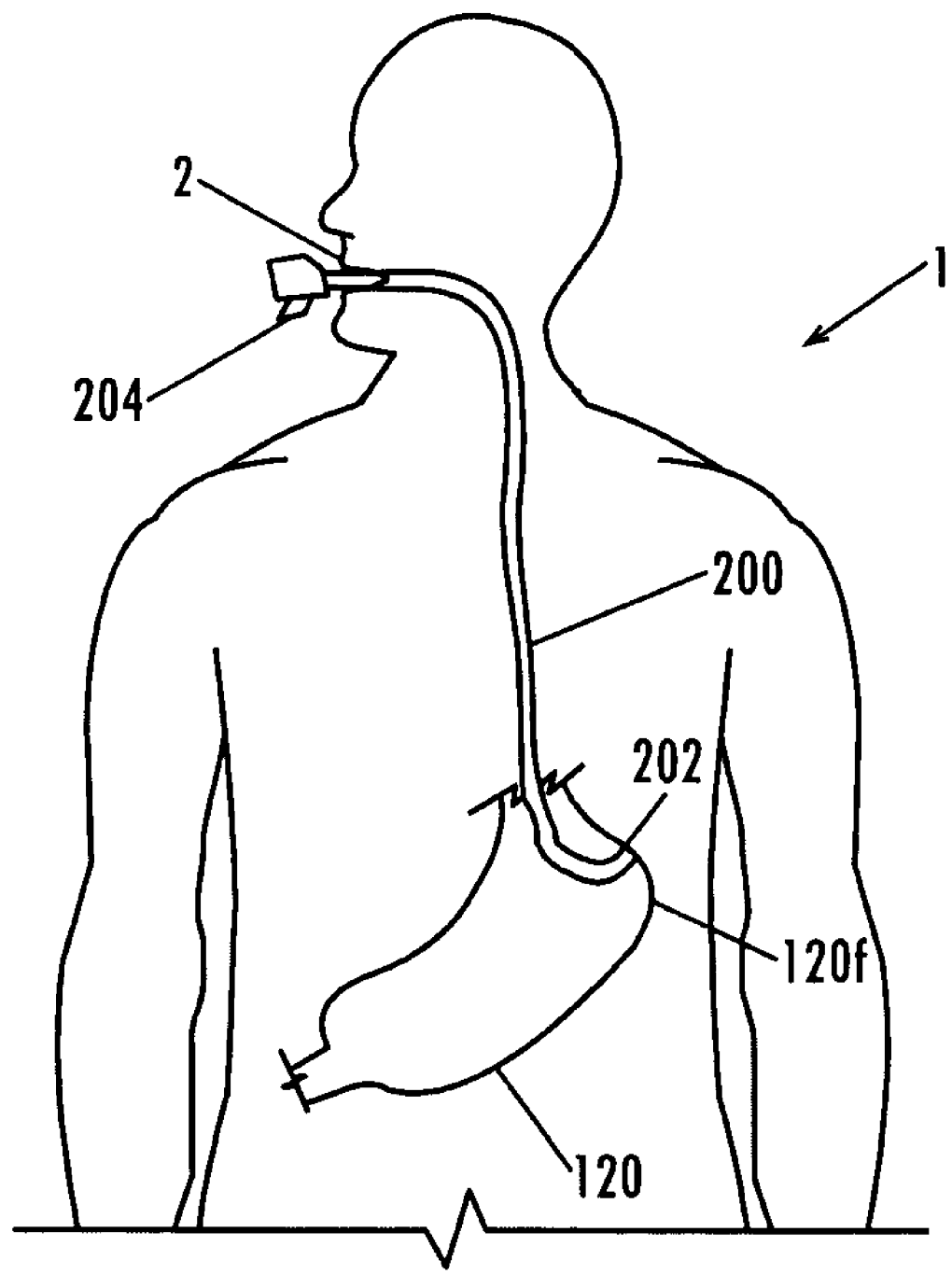
Figure 39A:
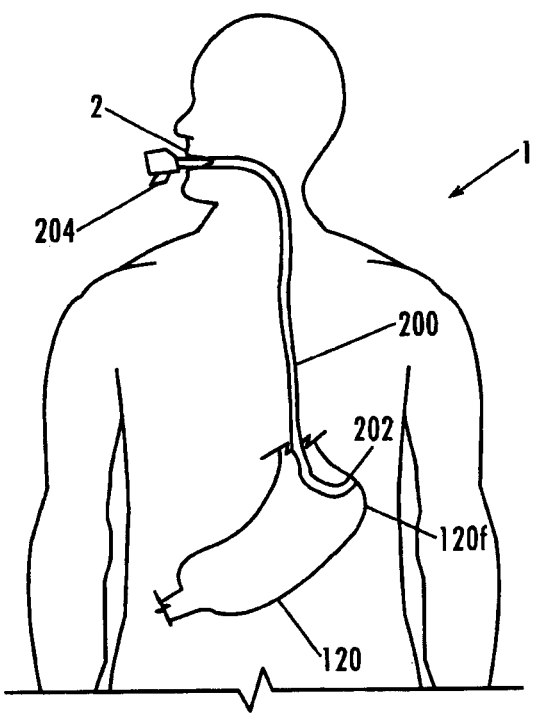
Figure 39B:
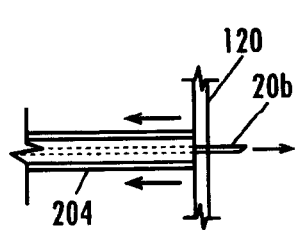
Figure 39C:
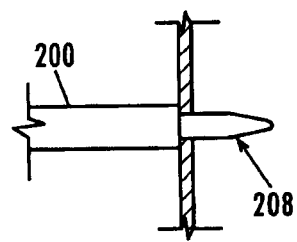

FIGS. 39A-39C illustrate steps of methods of transoral delivery and implantation of an expandable extra-gastric device according to one embodiment (with two variations) of the present invention. At FIG. 39A, a catheter 200 is inserted through the mouth 2 of a patient 1 and advanced down the esophagus and into the stomach 120, as illustrated. The distal tip 202 is maneuvered into contact with the inner lining of the stomach wall in a target location where the procedure is to be performed. A vacuum line/lumen 204 is provided with catheter 200 and vacuum is delivered to tip 202 to draw the inner wall against tip 202 as shown in FIG. 39A. Catheter 200 also includes a lumen through which a needle or other cutting or piercing instrument 206 is deliverable to the distal tip 202 of the catheter. Instrument 206 is delivered to distal tip 202 and extended distally therefrom to puncture, pierce or cut through the stomach wall, as illustrated in FIG. 39B, while vacuum is maintained to provide a counter force to the force applied by the cutting/piercing action.

Next, the opening through the stomach wall is dilated by inserting a dilator 208 (or a series of dilators 208 with progressively larger outside diameters) through the opening in the stomach, as illustrated in FIG. 39C. Dilator 208 may be inserted through catheter 200 after removal of instrument 206, or, alternatively, may be passed over the instrument 206 which in this case, functions like a guide wire.

After sufficient dilatation of the opening through the stomach wall, device 10 is next introduced, in a contracted state, in through the proximal opening of catheter 200 and delivered trans-orally into the stomach 120. Device 10 is pushed out the distal end of catheter 200 and through the opening in the stomach wall, to be delivered externally of the stomach wall. Suction can be maintained during this part of the procedure to maintain the distal end of catheter 200 in contact with the inner lining of the stomach wall around the opening that was made through the wall. An introducer or sheath or nosecone can be used to direct the device 10 through the opening through the stomach wall. Once expandable member 10em has been delivered through the wall of the stomach, expandable member 10em is then expanded, as illustrated in FIG. 39D. In this example, expandable member is an inflatable member and is expanded by delivery of fluid through conduit 12, which may be detachably connected to another conduit (not shown) running the length of catheter 200 through catheter 200 and connected to a source of fluid outside of the patient. As already noted, expandable member 10em may alternatively be a mechanically expandable member (which may then automatically self-expand upon passing it through the wall of the stomach, or expand after a sheath is removed, for example), or a composite member including at least one mechanically expandable component and at least one inflatable component. All of the above steps can be performed under visual guidance such as by fluoroscopy, ultrasound, or endoscope, for example. Prior to, or after expansion, expandable member 10em can optionally be additionally anchored at one or more locations using any of the anchoring techniques and features described above.

After expansion of expandable member 10em by the desired amount, adjustment member 80 (in this example, which includes an inflation port 84) is attached to the proximal end of conduit 12 as illustrated in FIG. 39E. The inflation conduit that passes through the catheter can be used to inflate the expandable member 10em and the adjustment member 80 can be attached thereto without substantially losing inflation pressure in the expandable member 10em by using an electromagnet on the catheter that mates with the adjustment member 80 when electrical power is supplied to the electromagnet. A needle extends from the catheter into the adjustment member 80 for adjusting the expandable member 10em.

After inflation, the electromagnet is turned off and the catheter is removed. Adjustment member 80 functions to anchor device 10, as well as to seal the opening through the stomach 120 on the inner layer of the stomach.

The expansion member 10em may be expanded only so far as to occupy a space that the stomach would normally expand into as it is being filled, to thus prevent such expansion. FIG. 39F illustrates an example, where expandable member 10em has been expanded only so far as to occupy the space that the fundus normally expands into when the stomach is being filled. Thus, expandable member 10em, in this case, does not substantially deform the stomach wall in its unfilled state. Additionally, in the example shown in FIG. 39F, surface 10p can optionally be anchored to the wall of the diaphragm, using adhesives, hooks, sutures, suction members, and/or tissue ingrowth surface and/or any of the fixation members discussed herein or in application Ser. Nos. 11/407,701, 11/716,985 and/or 11/716,986. Further optionally, additional anchoring may be provided by wedging expandable member 10em between the diaphragm 116 and stomach 120 and possibly the spleen.

FIG. 39G illustrates a variation of the method described above. In this instance, expandable member 10em is expanded sufficiently to deform the stomach wall inwardly, as shown. Thus, expandable member 10 is expanded until the desired amount of stomach deformation has been observed, prior to removing catheter 200. Observation of the deformation may be by any of the visualization techniques described above. Additionally, or alternatively, gastric sizing member 310 may be employed to gauge the appropriate amount of stomach wall deformation, in a manner as described above. Additionally, in the example shown in FIG. 39G, surface 10p can optionally be anchored to the wall of the diaphragm, using adhesives, hooks, sutures, suction members, or any of the fixation members discussed herein or in application Ser. Nos. 11/407,701, 11/716,985 and/or 11/716,986. Further optionally, additional anchoring may be provided by wedging expandable member 10em between the diaphragm 116 and stomach 120 and possibly the spleen.

Figure 40A:
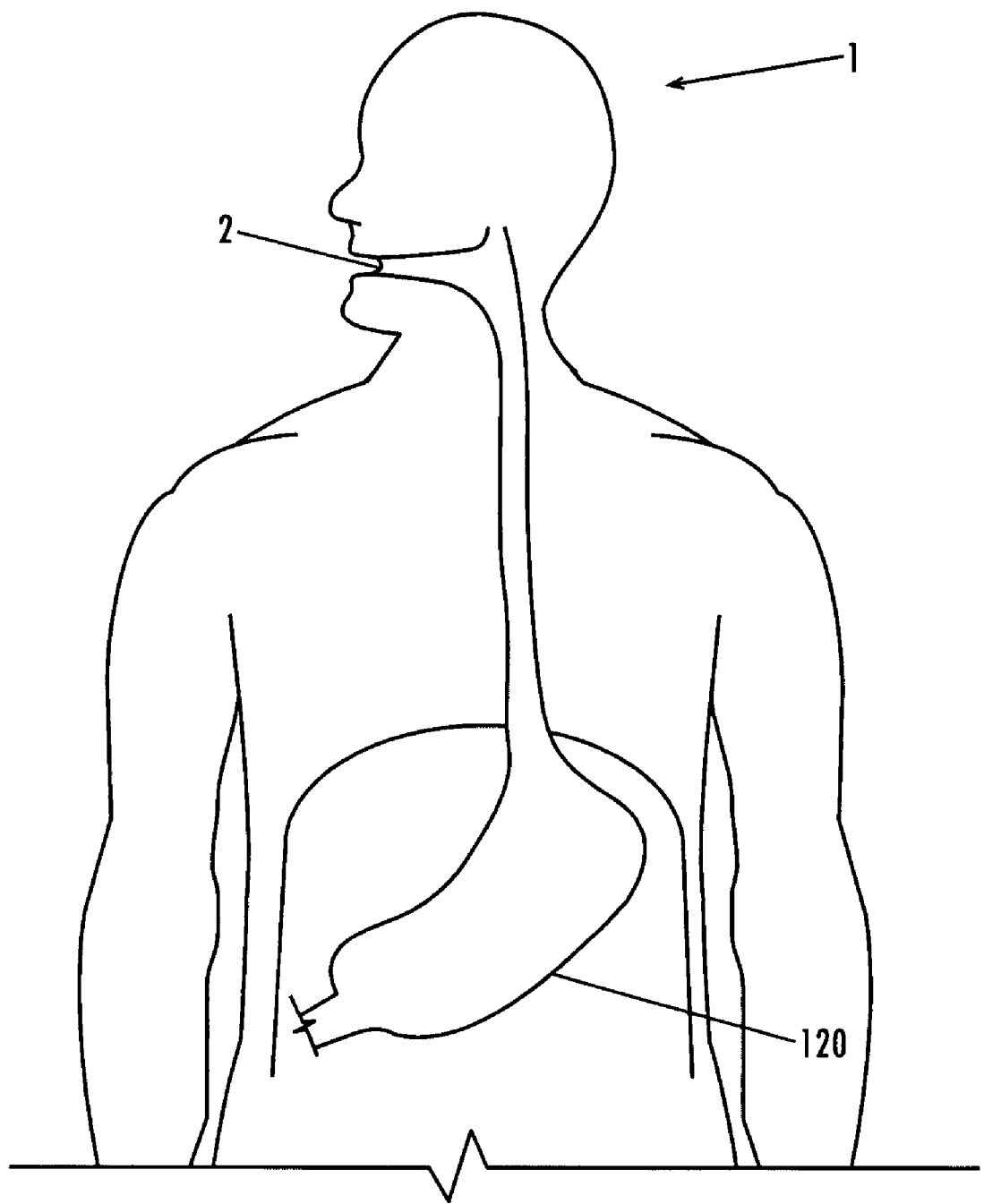
FIGS. 40A-40X illustrate steps of a method and devices for performing implantation of an extra-gastric device by a trans-oral procedure.
Figure 40B:
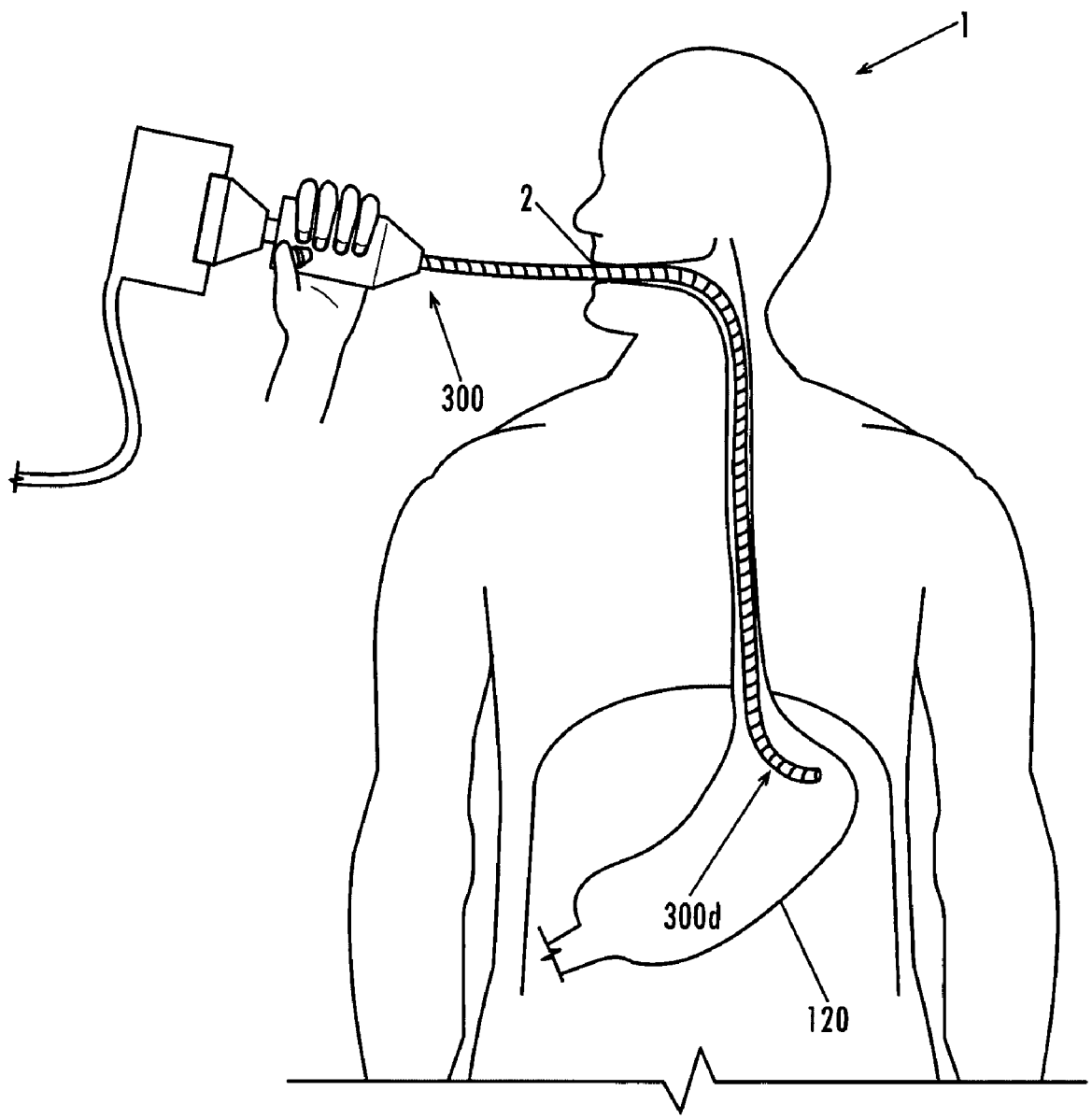
FIG. 40Y illustrates a device in a compact configuration with rotationally deployable talons deployed.
Figure 40C:
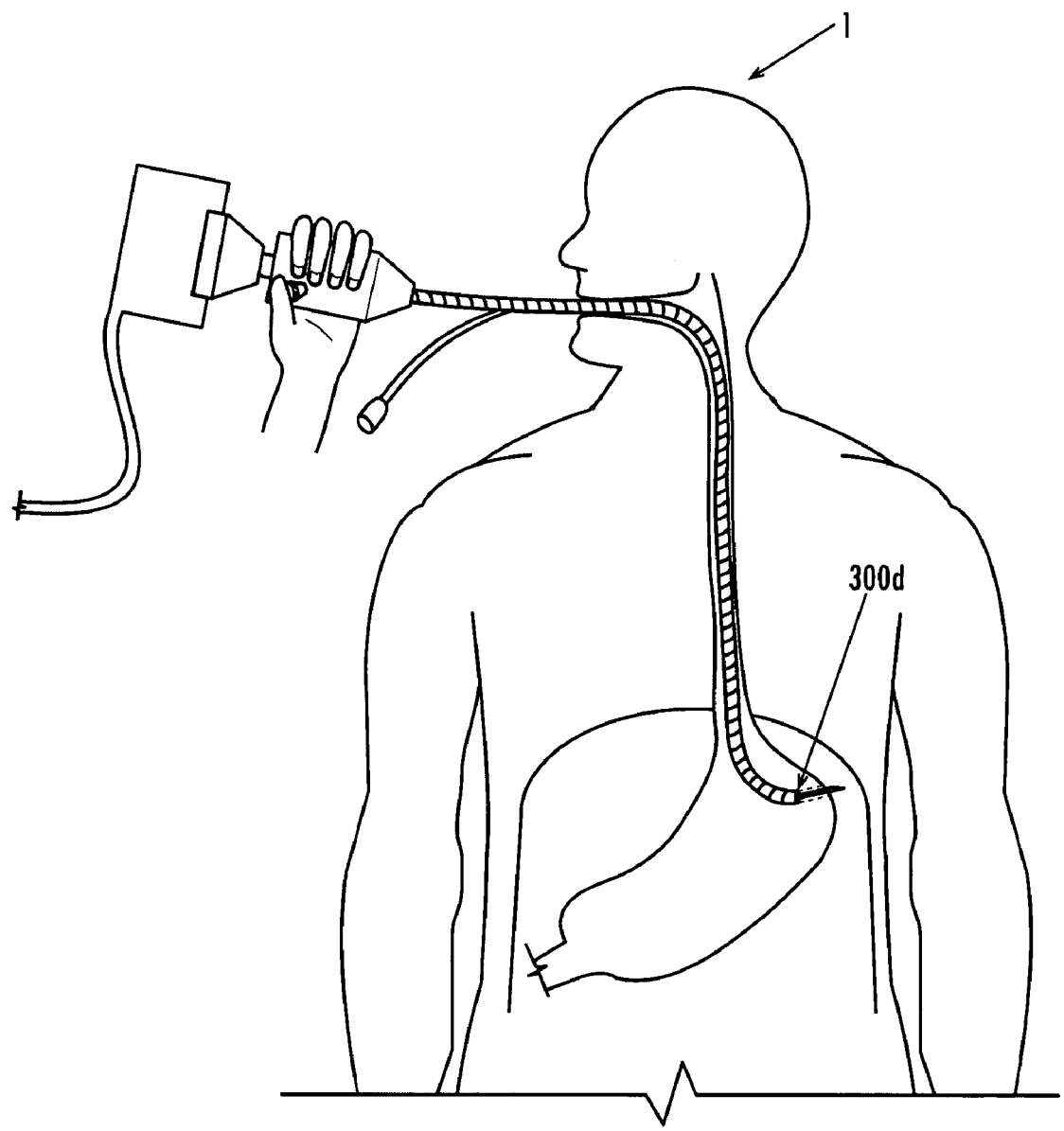
Figure 40D:
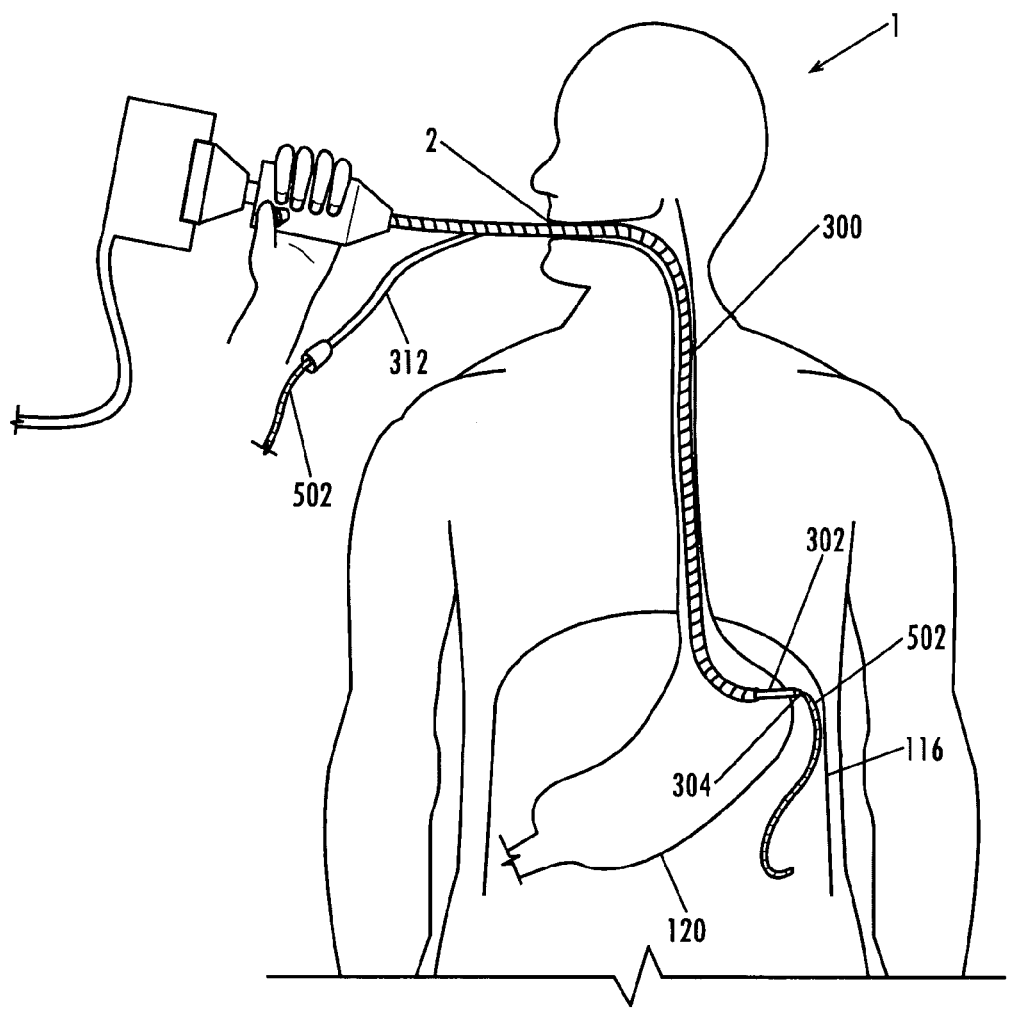
Figure 40E:
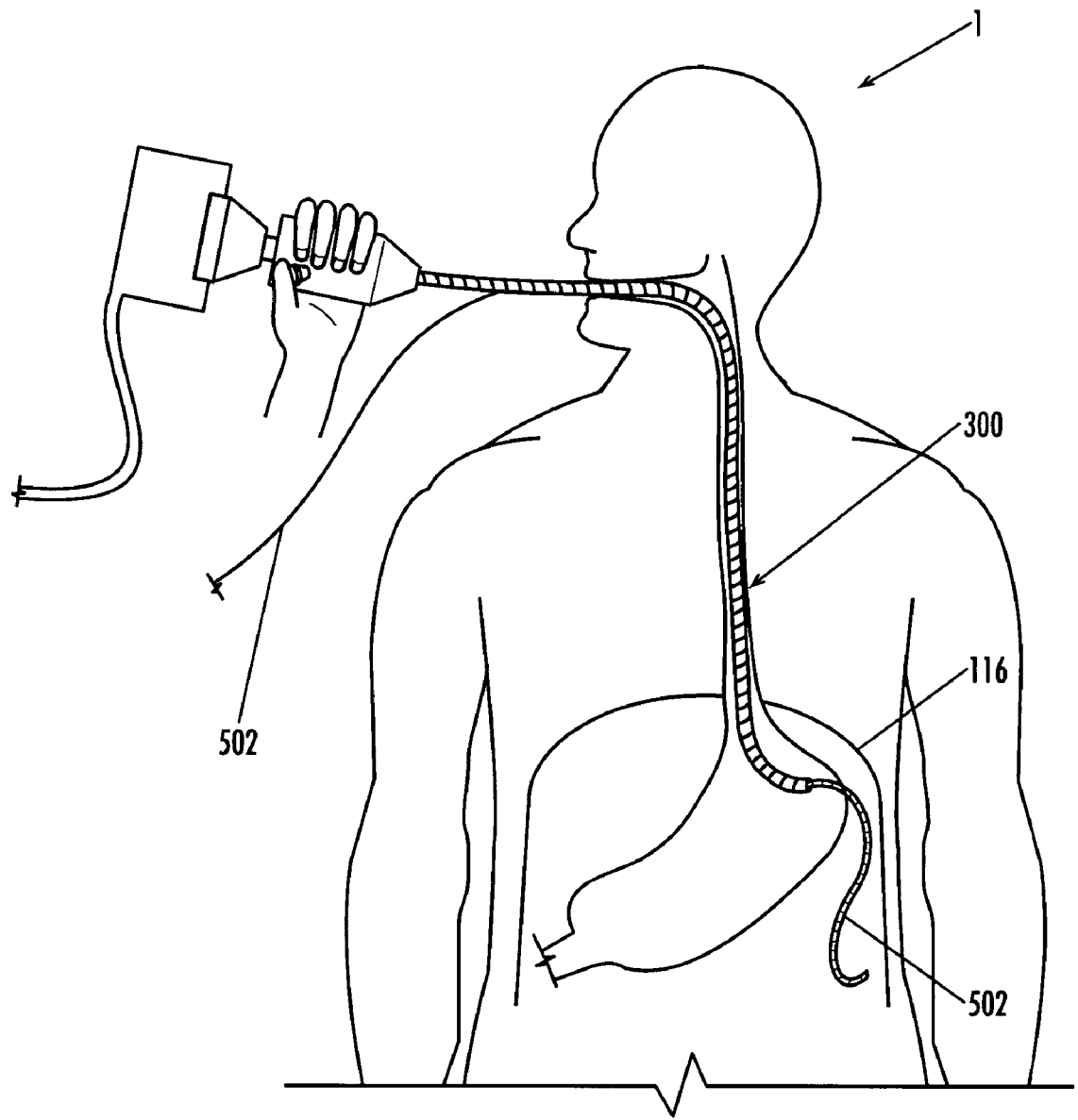
Figure 40F:
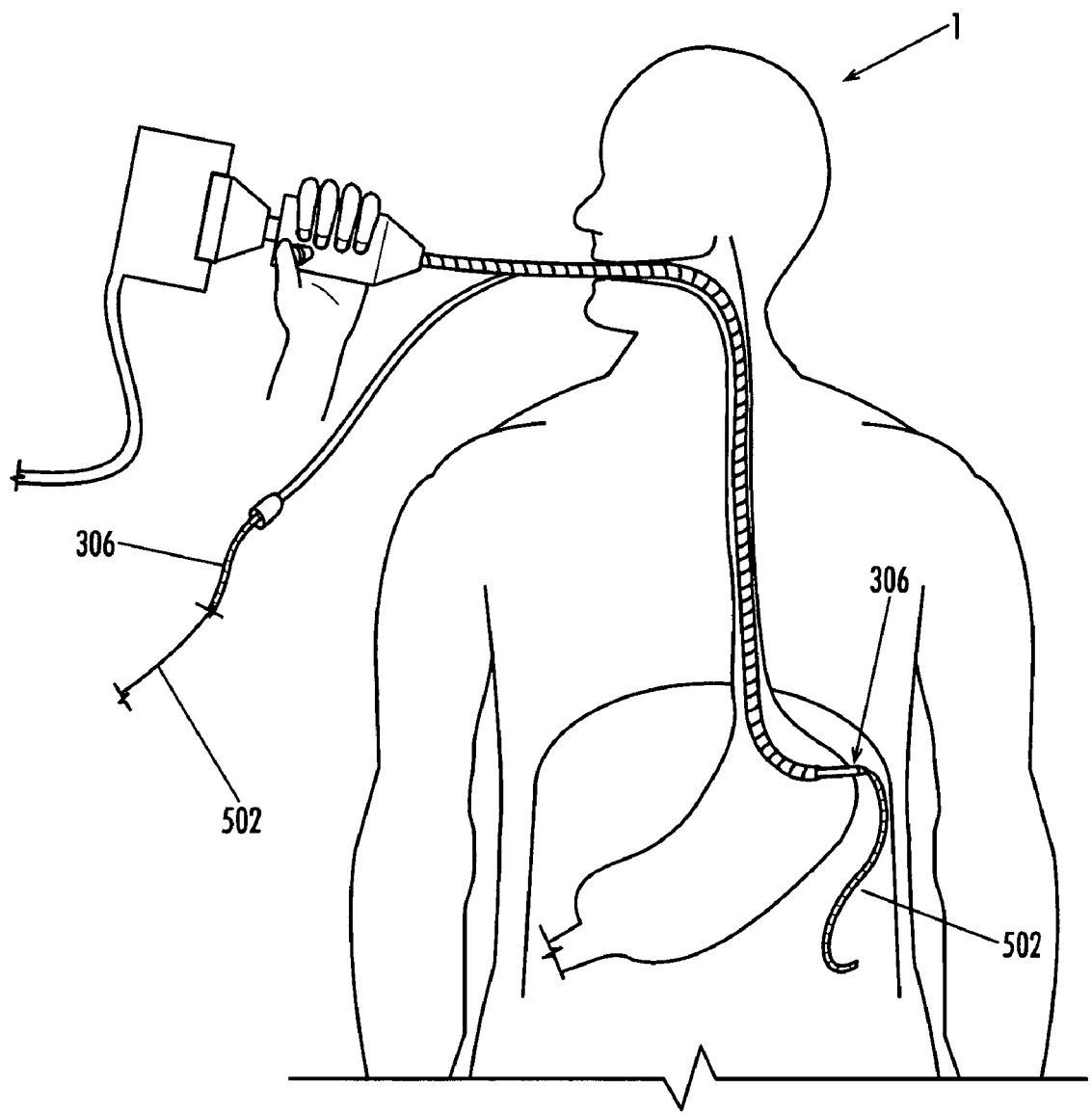
Figure 40G:
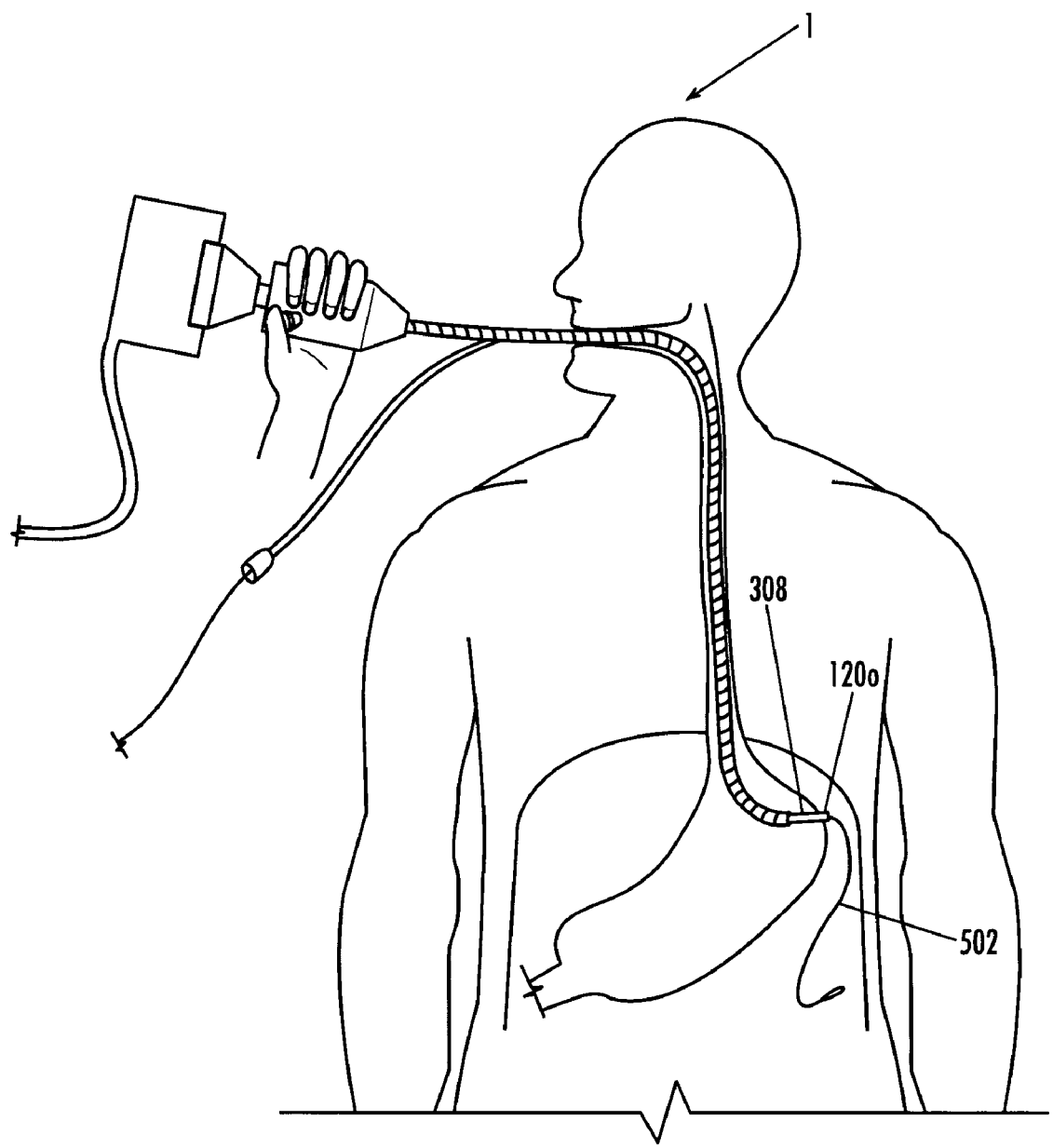
Figure 40H:
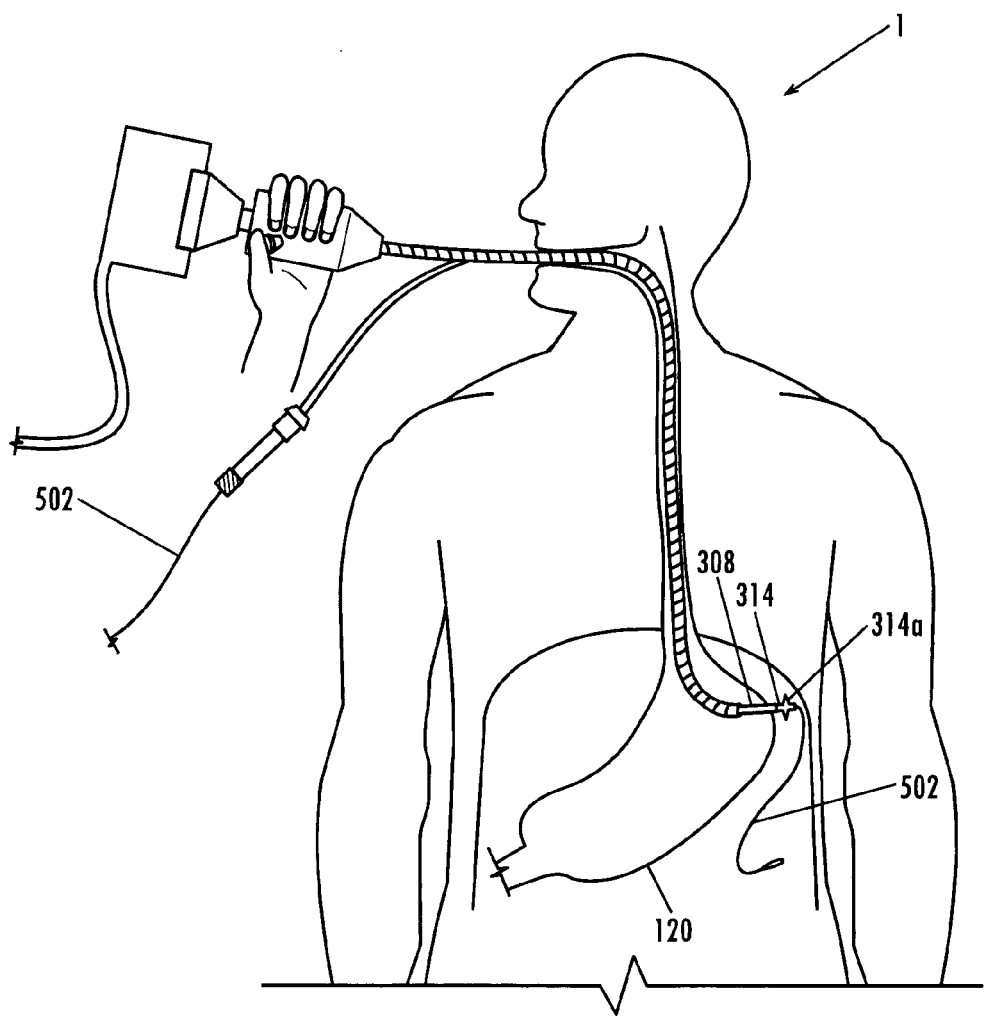
Figure 40I:
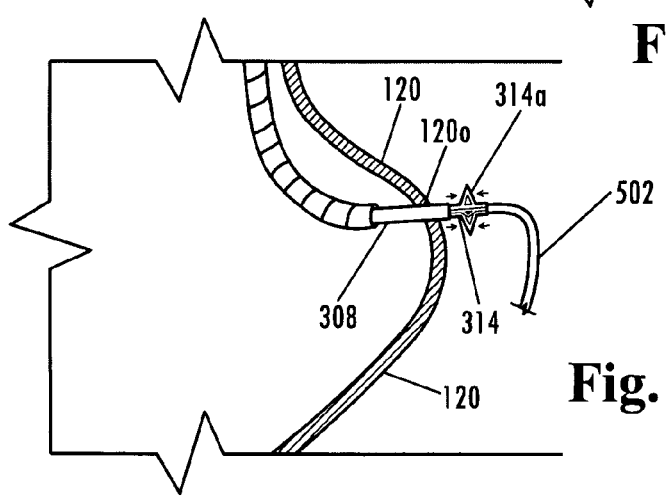
Figure 40J:
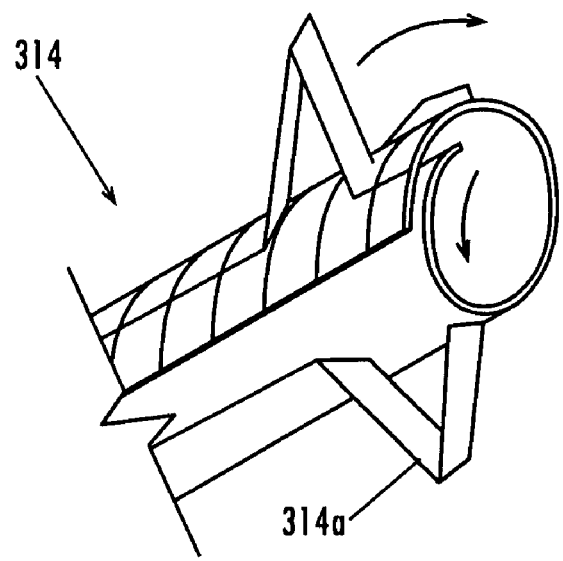
Figure 40K:
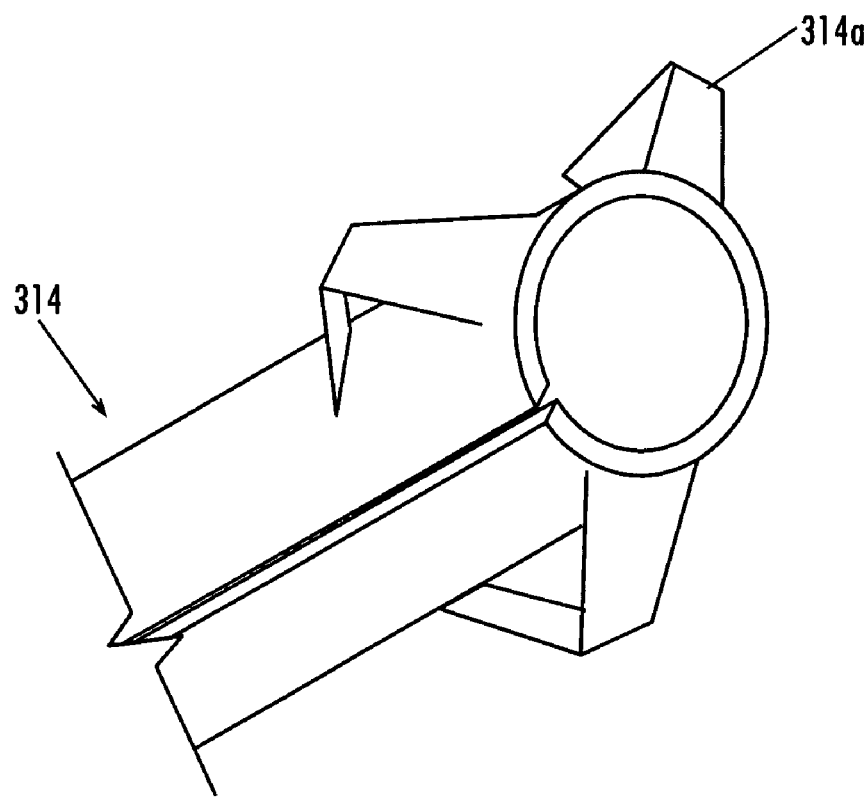
Figure 40L:
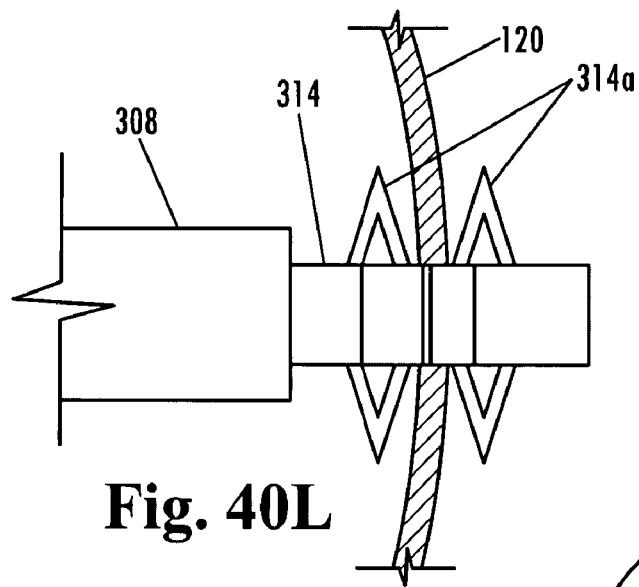
Figure 40M:
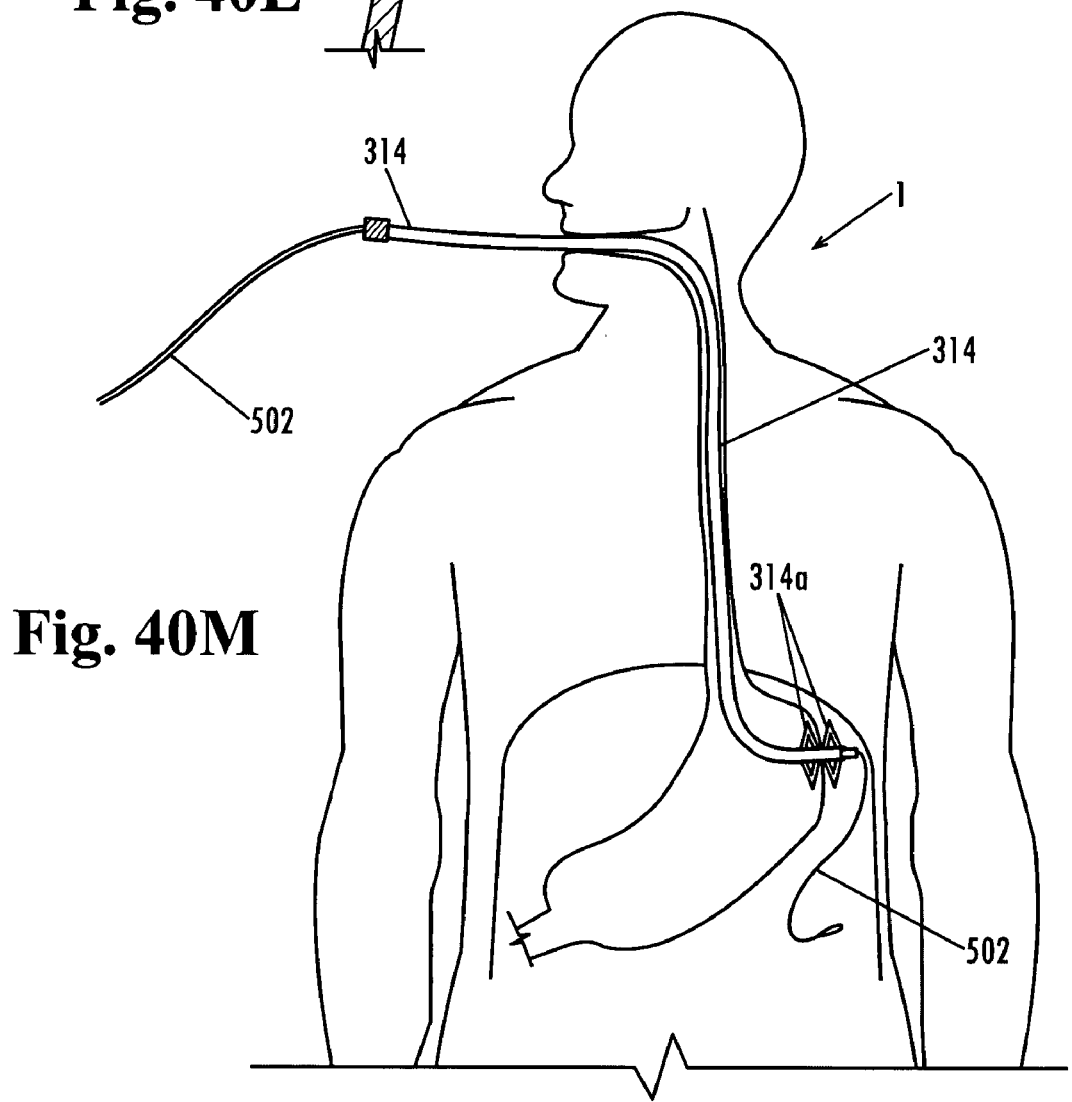
Figure 40N:
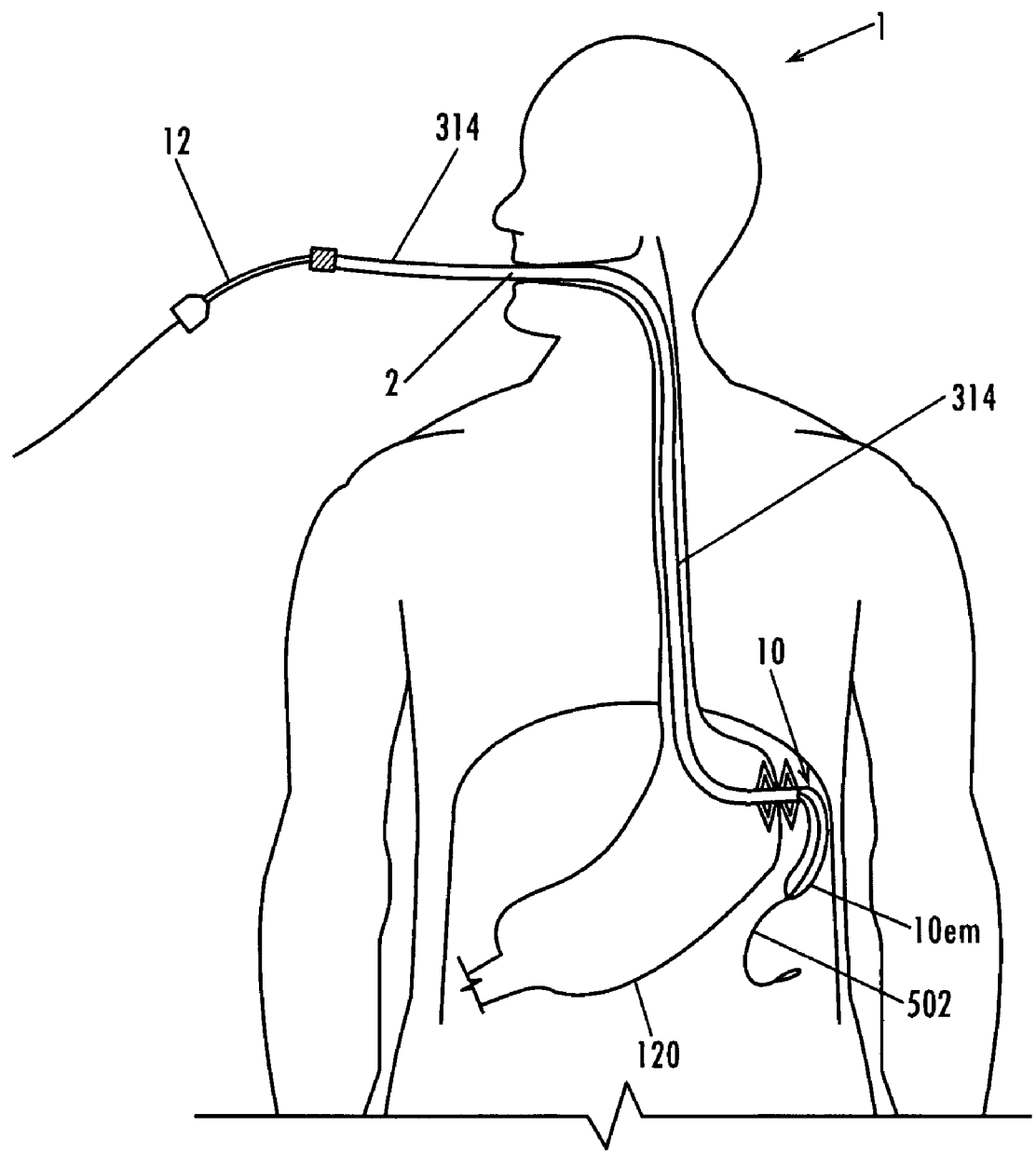
Figure 40O:
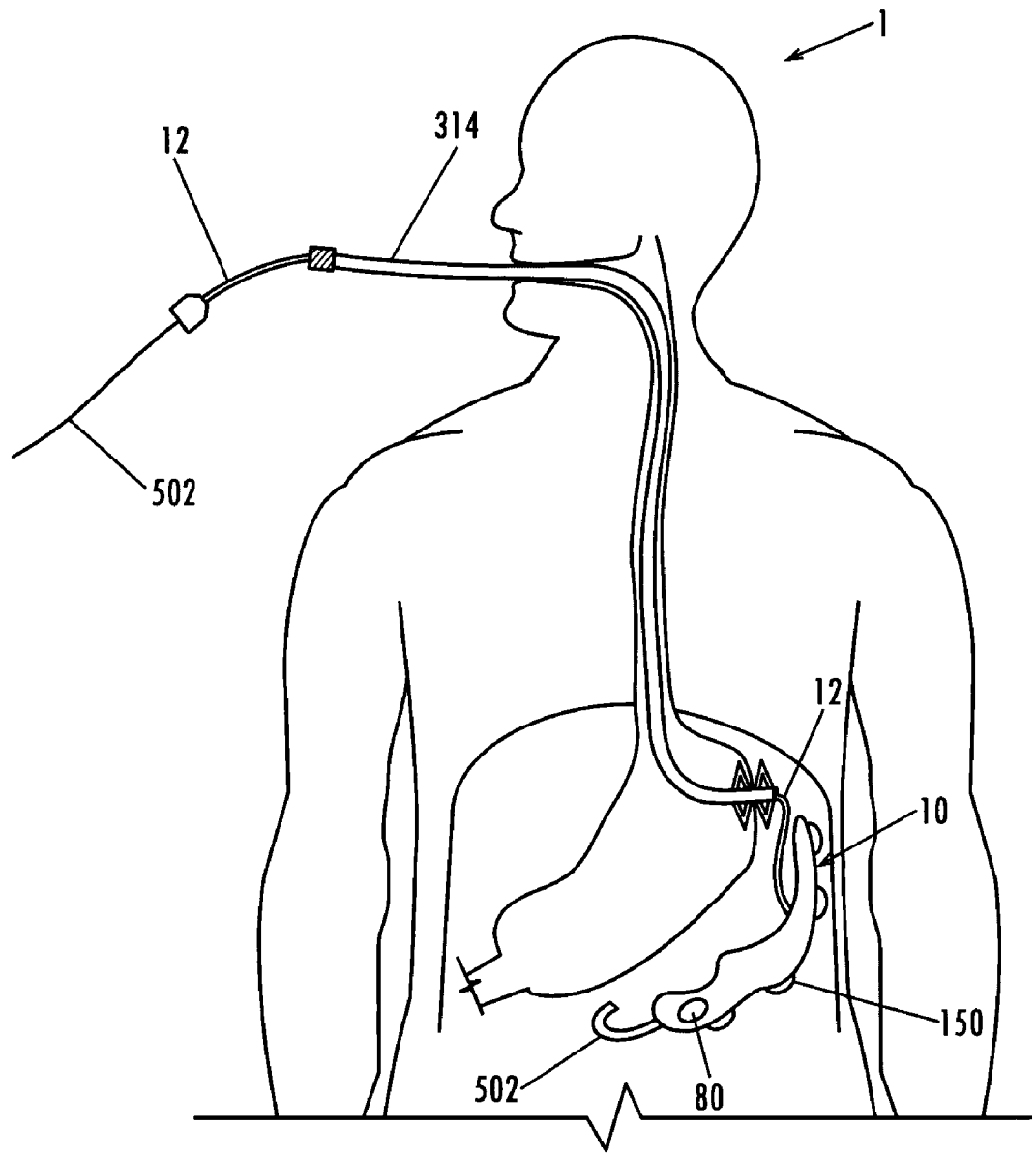
Figure 40P:
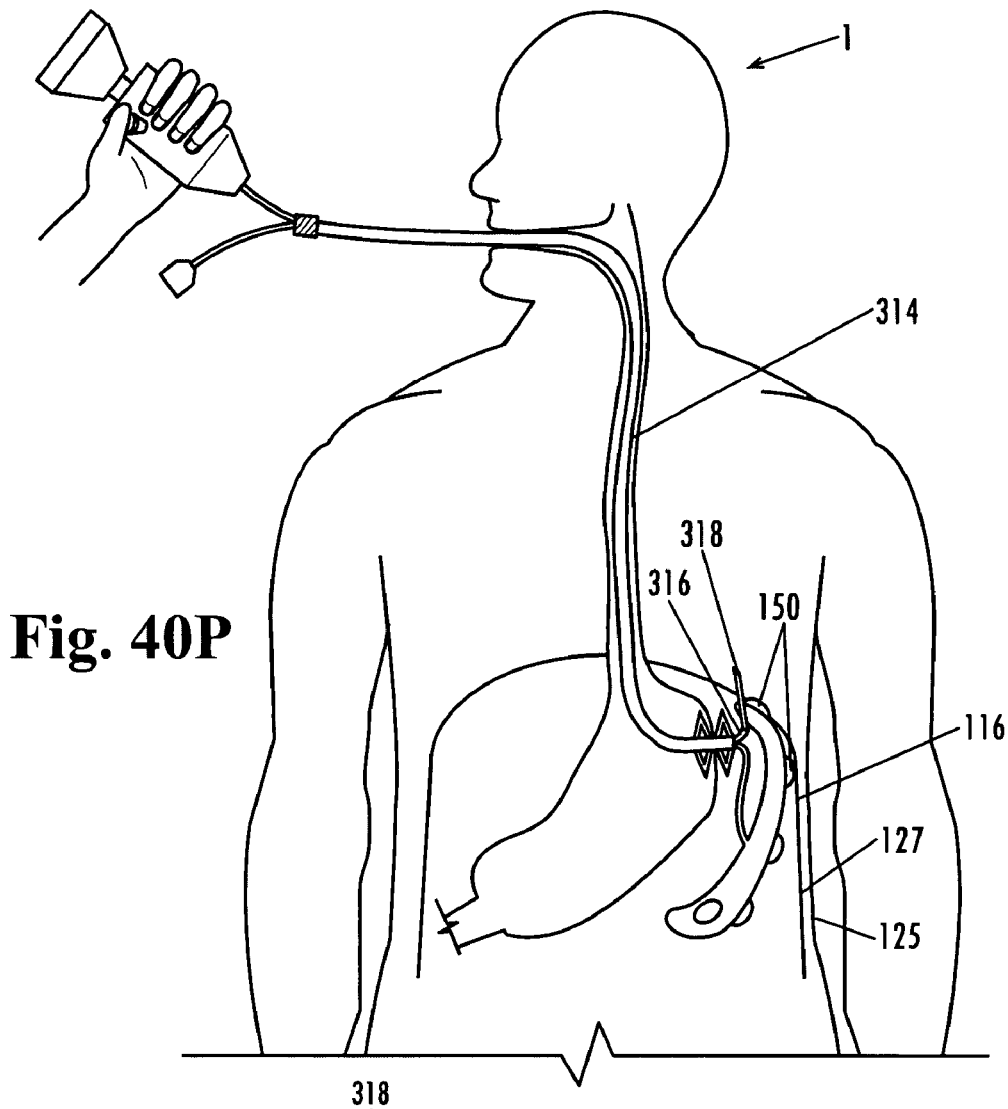
Figure 40Q:
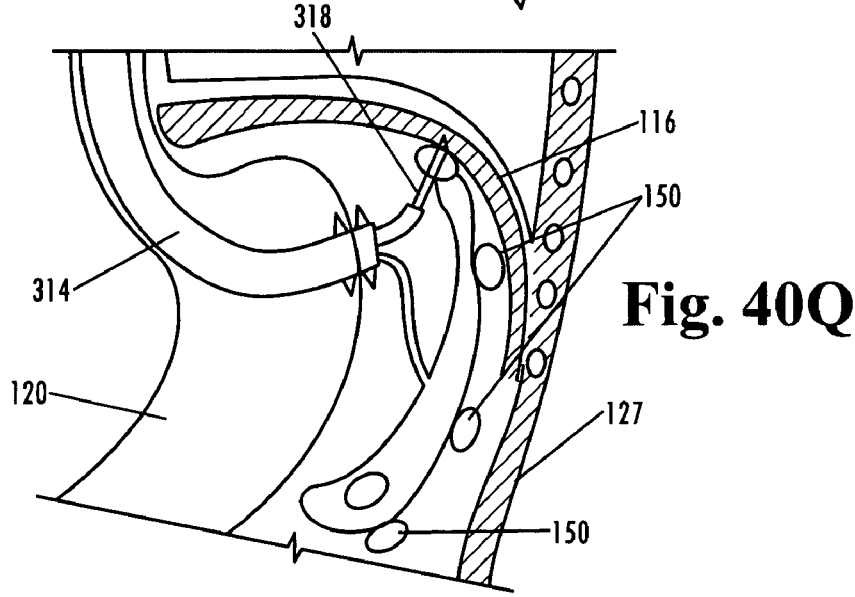
Figure 40R:
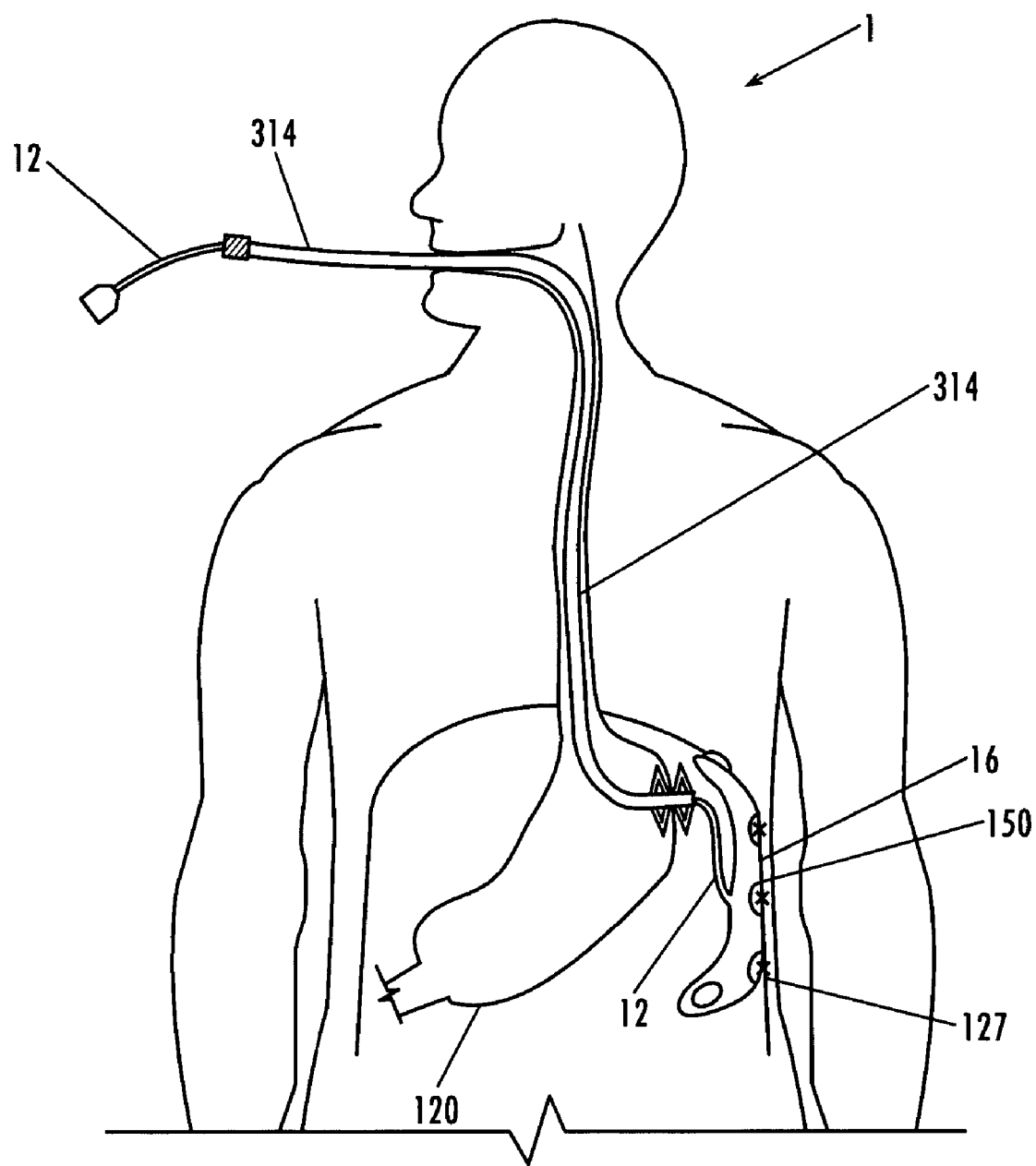
Figure 40S:
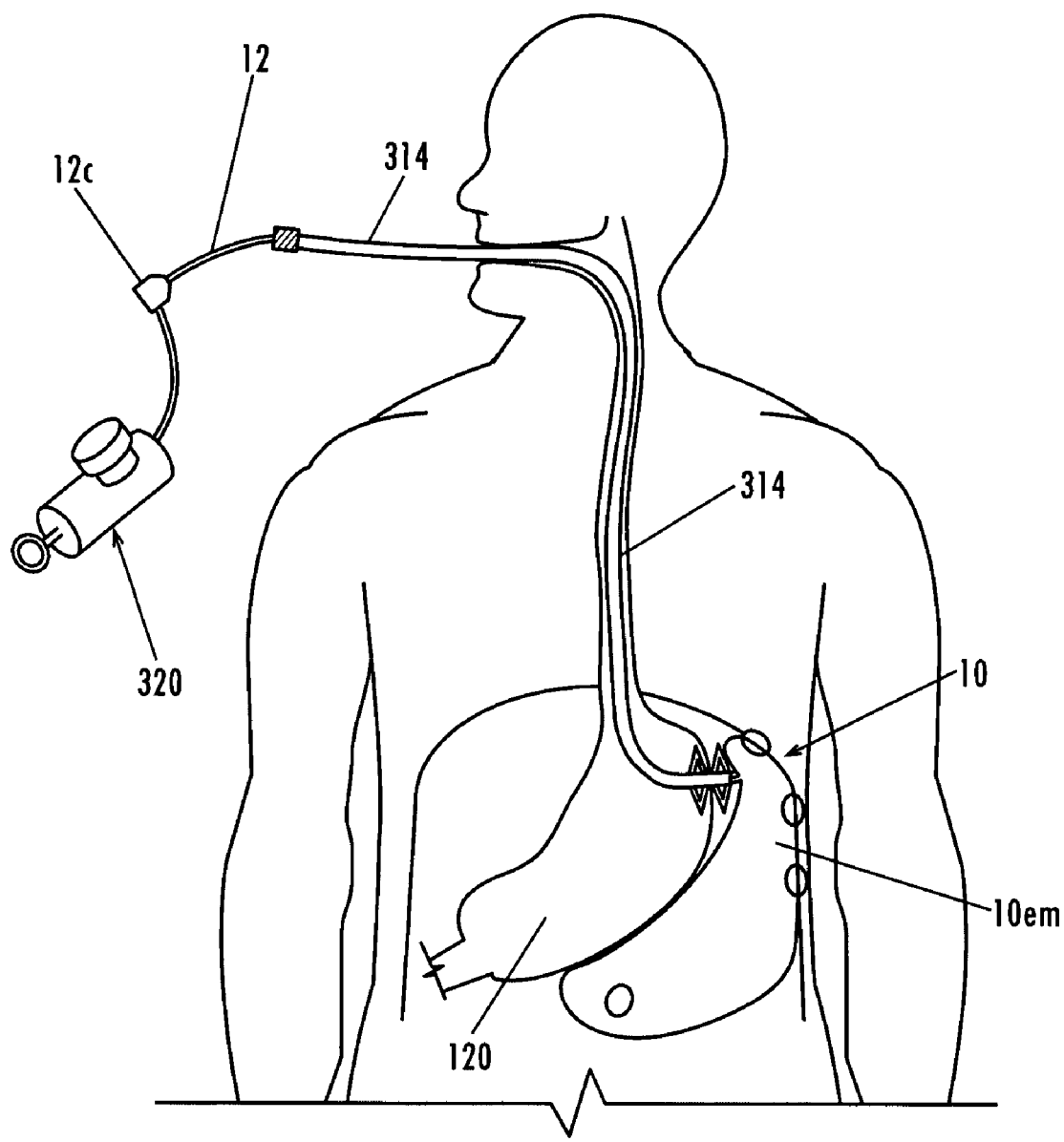
Figure 40T:
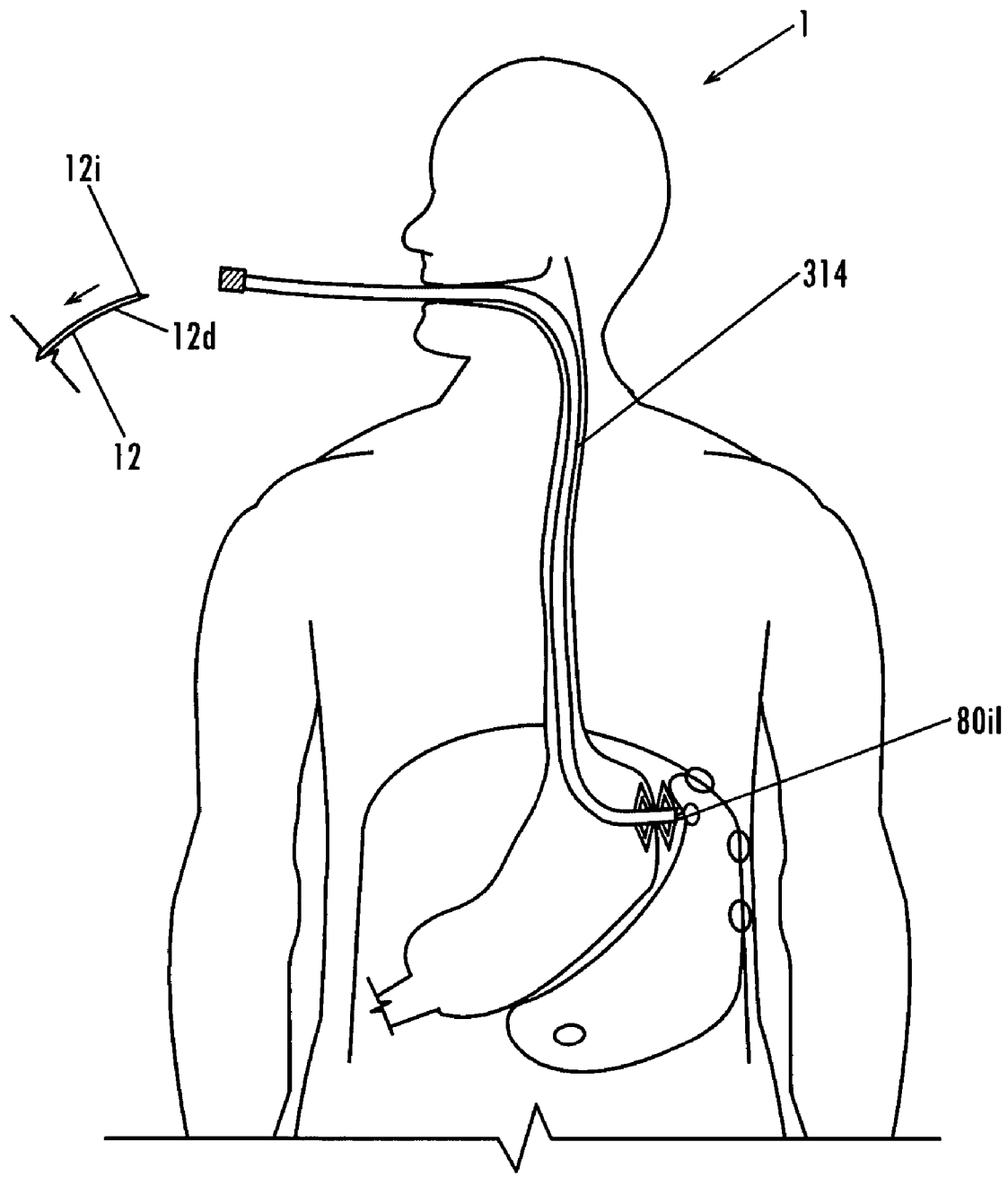
Figure 40U:
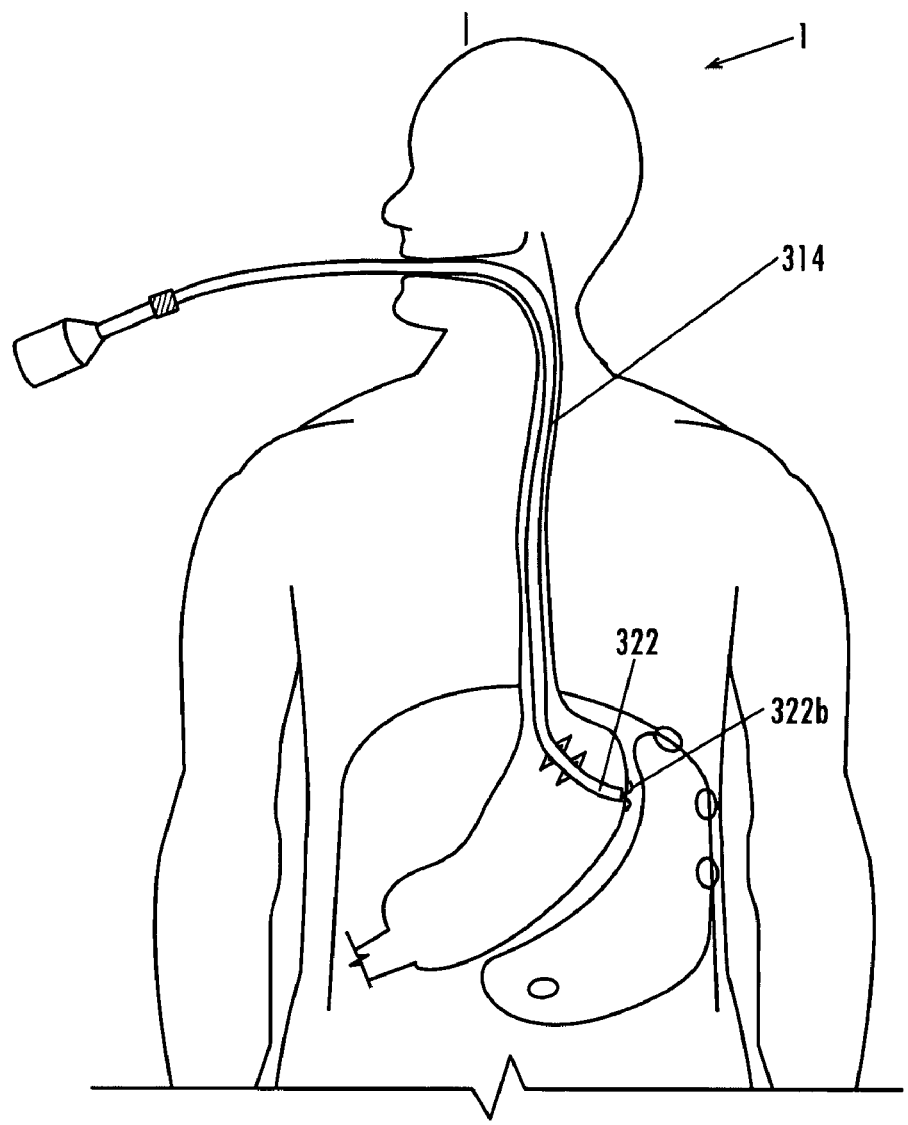
Figure 40V:
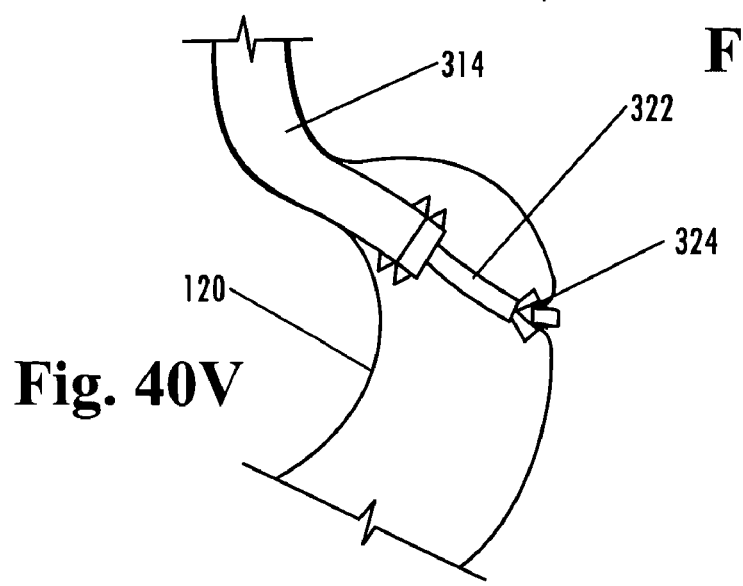
Figure 40W:
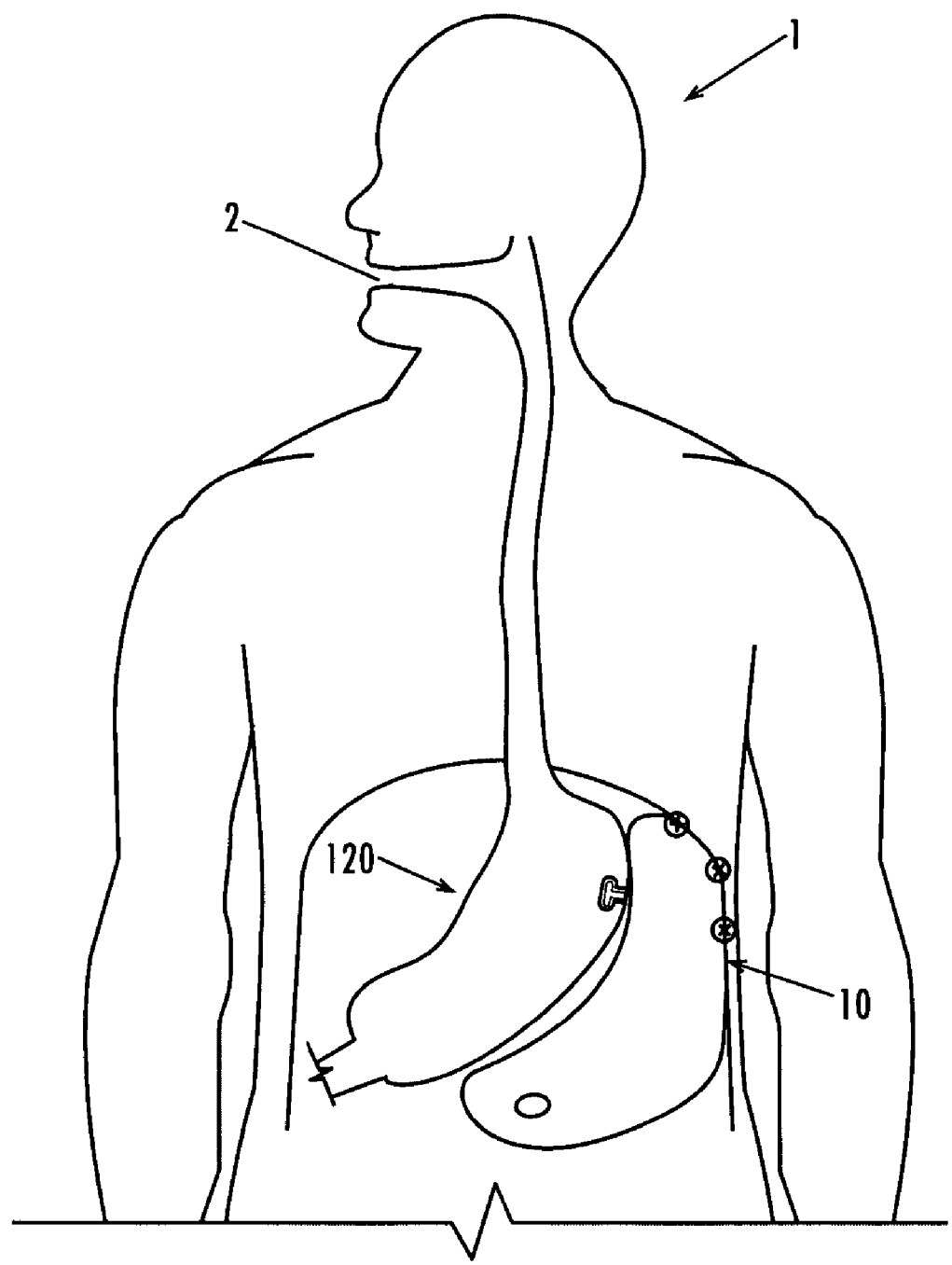
Figure 40X:
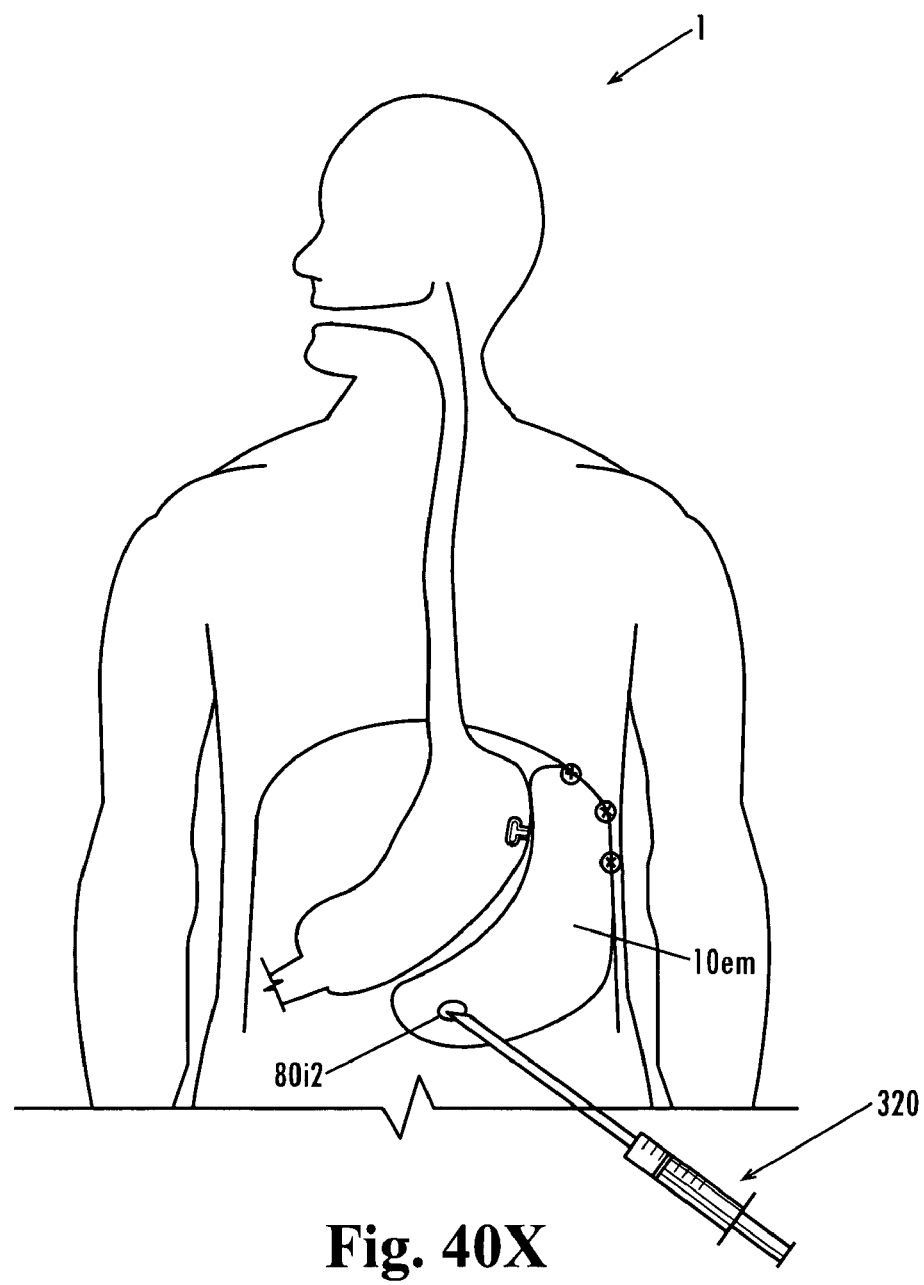

FIGS. 40A-40X illustrate steps of a method and devices for performing implantation of an extra-gastric device by a transoral procedure. FIG. 40A is a schematic, partial illustration of a patient 1 prepped and ready to receive instrumentation/devices via the mouth 2. FIG. 40B illustrates an instrument 300 having been inserted through the mouth 2 of patient 1 and advanced down the esophagus and into the stomach 120. Instrument 300 is a flexible, steerable, multi-lumen endoscope configured to provide visualization of a distal end portion of the instrument 300 from a location proximal thereof, and outside the body, and to perform procedures discussed hereafter, in some instances with additional instruments) being passed through one or more lumens of instrument 300. One example of an instrument 200 that can be used is EsopphyX™ by EndoGastric Solutions, Inc. Further details of this product can be found in one or more of U.S. Patent Publication Nos. 2006/0253131, 2007/0073318, 2007/0073323, 2007/0088373, 2007/0112363 and 2007/0129738, each of which is incorporated herein, in its entirety, by reference thereto. Alternatively, other multi-lumen, steerable endoscopes configured to be passed through the mouth 2, esophagus and into the stomach 120 to perform the procedures described herein may be used. Upon entering the stomach, the distal end portion 300d is steered to point toward a location of the internal wall of the stomach 120 through which it is desired to pass a device 10. This will typically be somewhere in the fundus region, although other locations may be selected to perform the procedures described herein.

FIG. 40C illustrates piercing the stomach 120 wall by extending a piercing tool 302 distally of the distal end of the main tube of instrument 300 to drive a sharp distal tip of tool 302 completely through the stomach wall. Optionally, the distal end portion 300d of instrument 300 may draw the inner surface of the stomach wall thereagainst by engagement with suction, as illustrated in phantom lines in FIG. 40C. The piercing tool 302 may include a central lumen 304 configured and dimensioned to permit a guidewire 502, rail, or other compact guide structure to be passed therethrough. For example, piercing tool may have a structure of a hollow needle.

FIG. 40D illustrates guidewire 502 having been passed through a conduit 312 connecting to one of the lumens in instrument 300 and the lumen 304 of tool 302. Guidewire 502 is passed through the passageway formed by the lumen so that a distal portion thereof extends distally of the distal tip of tool 302 and thus into the intra-abdominal cavity, as illustrated in FIG. 40D. Next, at FIG. 40E, the piercing tool 302 is removed over the guidewire 502 leaving only instrument 300 in place with guidewire 502 extending across the stomach wall and into the intra-abdominal cavity.

A dilator tool 306 is delivered over guidewire 502 and passed across the stomach wall to dilate the opening through the stomach wall, as illustrated in FIG. 40F. After dilation by a first dilating tool 306 of a first size, this tool may be removed and a second dilating tool 306, having a relatively larger outside diameter at a distal end working portion thereof, can be inserted in the same manner to further dilate the opening. This procedure can be iterated with ever increasingly larger dilators 306 until the opening through the stomach wall has been dilated to an amount desired by the surgeon. Alternatively, use of a single dilator 306 may be sufficient. Further alternatively, a single dilator 306 may be used that has an expansible distal working end.

Once the opening 120o through the stomach wall has been sufficiently dilated, dilation tool 306 is withdrawn over guidewire 502 and removed, and a cannula 308 is inserted though opening 120o in its place, as illustrated in FIG. 40G. A flexible sheath 314, which is expandable radially to both adjust to the size of the dilated opening 120o and to form anchors 314a at locations both externally and internally against the stomach 120 wall, is next passed over the guidewire/rail 502 and through cannula 308, so that a distal most anchor 314a extends distally of the distal end of cannula 308 and expands radially, as illustrated in FIG. 40H, so that a distal end portion of sheath 314 and distal most anchor 314a extend through into the intra-abdominal cavity. The distal end portion of the sheath 314 has the capability to expand once it has traversed the stomach wall, thus allowing a very small opening to be created through the stomach wall to permit the sheath to pass through in the non-expanded configuration, thereby minimizing trauma to the stomach wall. Various expandable features may be provided at the distal end portion to configure it to be expandable, including, but not limited to: dual expandable balloons, dual ribs, swellable (e.g., hydrophilic) rings, of the expandable arms shown, for example. The arms 314a deploy via differential axial movement between inner and outer shafts. Arms 314a are formed in slots of the outer shaft and, as the inner shaft slides within the outer shaft and proximally relative thereto, the distal ends of the arms 314a, which are attached to the inner shaft, buckle as they are driven toward the proximal ends of the arms 314a. FIG. 40I is an enlarged partial sectional view of FIG. 40H showing the expansion of the distal most anchor 314a in more detail.

FIGS. 40J-40K are enlarged views of the distal end portion of expandable sheath 314 illustrating the expandable action thereof. As an optional feature, the shafts of sheath 314 can themselves be expandable by being formed with a slot and coiled as shown. Accordingly, upon insertion of a dilator, this forces the shafts from the coiled format in FIG. 40J to the tubular, expanded configuration shown in FIG. 40K, as the wall edges abut one another. It is further noted, that, as another option, only a distal end portion of sheath 314 may be provided with the expandable coil configuration, while the remainder of the sheath 314 proximal thereof is a contiguous tube. Additionally, the proximal contiguous portion may be made to have a larger diameter than the distal expandable portion (in its coiled, collapsed configuration, and further optionally, even larger than the expanded, cylindrical configuration).

After expansion of the distal most anchor 314a, described above with regard to FIG. 40I, sheath 314 is retracted proximally until anchor 314a abuts against the outer wall surface of the stomach 120. Cannula 308 is next retracted proximally to allow a more proximally placed anchor 314a to expand against the inner wall surface of the stomach 120 wall as illustrated in the partial, sectional view of FIG. 40L. At this stage, sheath 314 is now fixed relative to the stomach wall, so that it will neither move proximally or distally through opening 120o. Next, instrument 300 (including cannula 308) is withdrawn over sheath 314 and removed from the patient 1, leaving only sheath 314 and guidewire 502 in place as illustrated in FIG. 40M.

Device 10 can then be inserted through sheath 314, over guidewire 502, from a location outside of the patient, through a proximal opening in sheath 314, past the mouth 2 of the patient 1, through the esophagus and opening 120o in the stomach 120 to an extra-gastric location in the intra-abdominal cavity where it is desired to implant the device, as shown in FIG. 40N. In the embodiment shown, conduit 12 is releasably connected to expandable member 10em and extends out of the proximal end of sheath 314 for use in initially inflating expandable member 10em, as described in more detail below. In other embodiments, such as when a device having a self inflating expandable member is used or a device having a mechanically self expanding member, conduit 12 may not be needed. Further alternatively, even devices having inflatable member 10em can be inflated without the conduit 12 shown in FIG. 40N, although this conduit 12 is typically used for performing the initial inflation trans-orally.

At FIG. 40O, device 10 is shown fully inserted into the intra-abdominal cavity, and conduit 12 can be seen extending back through sheath 314. Next a flexible endoscope 316 with an attachment tool 318 is inserted through sheath 314 so that a distal end of endoscope extends out of the distal end of sheath 314, so that device 10 can be viewed from outside of the patient 1 and endoscope 316 can be manipulated to provide fine adjustments of the positioning and orientation of device 10 if needed. For example, one or more graspers may be inserted through sheath 314, either through endoscope 316 or adjacent thereto to grasp portions of device 10 (such as tabs 150, for example) and move them to reposition device 10 while visualizing the process via endoscope 316. Endoscope 316 is inserted so that the target sites can be identified visually by the user from a location outside of the patient, via endoscope 316. Attachment methods and tools used may vary. Non-limiting examples of attachment methods follow. For example, sutures can be thrown into the target locations (e.g., on the abdominal wall) and device 10 can be delivered over them, such that the sutures function like guidewires. Device 10 can then be fastened into place at the target site with locking anchors, or by tying off the sutures. Alternatively, the aforementioned technique may be used to first secure an anchoring platform at the surgical target site (e.g., anchored to the abdominal wall and/or other intra-abdominal structure other than the stomach) and device 10 can then be secondarily attached/anchored to the anchoring platform. Alternatively, the anchoring platform can be stapled to the one or more intra-abdominal structures to anchor it in place. Another alternative technique includes providing device 10 with rotationally deployable talons 59t as illustrated in the deployed configuration on a device 10 in the compact configuration in FIG. 40Y. Further alternatively, talons 59t may be installed around an integrated adjustment member 80i of device 10 according to known techniques. The rotationally deployable talons 59t, wherever installed, provide the advantage of the capability of deploying sharp anchoring features without ever exposing a sharp edge during delivery to the target site.

Optionally, fluoroscopy may be used to further assist visualization. Once device 10 is positioned and oriented to the satisfaction of the surgeon, attachment tool 314 can be distally advance so that a distal working end of the attachment tool attaches portions of device 10 to one or more intra-abdominal structures. In the example shown, helical tacks are inserted through tabs 150 and into the diaphragm 116 and the abdominal wall 127, depending upon the location of each tab 150, see FIG. 40Q. More often, however, device 10 will be attached at one or more locations of the abdominal wall 127 without attaching to the diaphragm. Alternatively or additionally, other internal abdominal structures may be used as attachment loci for one or more tabs 150. Other attachment features may be used alternatively, or in addition to helical tacks, including, but not limited to: sutures, staples, adhesives, etc., or an attachment pad 170,179 as described in more detail below.

After anchoring device 10 at all locations desired, visualization of the anchored device can optionally be performed as a review to help satisfy the surgeon whether or not the device 10 has been placed as intended. Once it has been decided that device 10 has been properly placed, oriented and anchored, all tools remaining in sheath 314 (which may include attachment tool 318, endoscope 316 and/or graspers or other tools) are withdrawn and removed from sheath 314 and the patient 1, to prepare for initial inflation of expandable member 10em. FIG. 40R shows the arrangement when the device 10 is ready to be inflated. Next, a source of pressurized fluid, such as inflation device 320 is attached to the connector 12c at the proximal end of conduit 12 and pressurized fluid is inputted through conduit 12 into expandable member 10em to inflate it, as shown in FIG. 40S. The inflation device may deliver pressurized gas, pressurized liquid, or a combination of pressurized gas and liquid. Further alternatively gas and liquid may be sequentially inputted by separate sources of pressurized gas and pressurized liquid, respectively.

Once expandable member 10em has been inflated to the extent desired, conduit 12 is pulled free of engagement with integrated adjustment member 80i1 and removed from sheath 314 and the patient 1, as illustrated in FIG. 40T. The distal end of conduit 12 may be provided with an insertion needle 12n that is inserted through the valve in integrated adjustment member 80i1 so that conduit 12 and expandable member 10em are connected when initially delivered into the abdominal cavity, as was noted above. This connection is releasable and may be provided by a simple friction fit. Optionally, additional connector features may be provided, such as detent 12d, for example, or other mechanical, releasable fixation structures. Adjustment member 80i1 may be configured like any of the adjustment members described herein or in application Ser. Nos. 11/716,986; 11/716,985; 11/407,701; 60/833,284 and/or 60/877,595.

Next, at least distal anchor 314a (and preferably both anchors 314a) are collapsed to more closely conform to the outer wall of sheath 314, thereby allowing the distal end portion of sheath 314 to be retracted back within the stomach 120, as illustrated in FIG. 40U. A closure tool 322, such as an endostitcher for example is next inserted through sheath 314 to be used to close the opening 120o in the stomach. For example, 22b or other grasping structure may be extended through opening 120o and then retracted to invaginate the wall portions surrounding the opening 120, after which the invaginated portions of the stomach wall are clipped 324, sutured or stapled closed, as illustrated in FIG. 40V. Alternative closure tools may be used, such as StomaphyX™ by Endogastric Solutions, as one non-limiting example, or alternative tools such as those available from Perclose, as another non-limiting example.

After closure of the opening 120o, the closure tool 322 is withdrawn from the patient and the sheath 314 is withdrawn from the patient to complete the procedure. FIG. 40W illustrates the device 10 implanted in the patient 1, after completion of the procedure. It is noted that no attachment to the stomach is required, nor do any openings through the stomach remain after completion of the procedure, and that the closed portion that had the opening therethrough will typically completely heal shut shortly thereafter.

If adjustment of the amount of inflation of expandable member is needed after completion of the procedure (such as during a return, checkup visit, for example) a source of pressurized fluid 320 having a sharpened distal tip can be inserted through the skin, subcutaneous fat and abdominal wall to engage the adjustment member 80i2, at which time, fluid can be added or removed from the expandable member 10em, as illustrated in FIG. 40X.

Figure 41A:
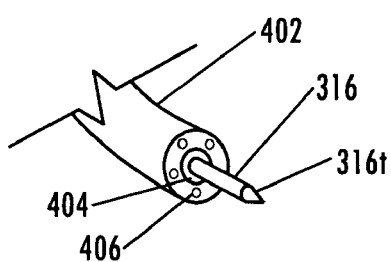
FIGS. 41A-41L illustrate alternative method steps and devices for performing implantation of an extra-gastric device by a trans-oral procedure.

FIGS. 41A-41L illustrate alternative method steps and devices for performing implantation of an extra-gastric device 10 by a trans-oral procedure. FIG. 41A illustrates a distal end portion of a flexible sheath or endogastric tubing 402. Tubing 402 is configured and dimensioned to be inserted through the mouth 2 of a patient 1, through the esophagus and into the stomach 120 and has sufficient length so that a proximal portion thereof extends proximally out of the mouth 2 even when the distal end of tubing 402 abuts against the inner surface of the stomach wall. A working channel 404 is provided as a lumen extending through tubing 402 and is dimensioned to receive various tools therethrough as will be described below. One or more suction lumens 406 are provided peripherally of working channel 404 and extend through tubing 402 for connection with a suction source proximally of tubing 402. Suction lumen(s) 406 extend and open to the distal end of tubing 402. As shown, five suction lumens 406 peripherally surround the working channel 404. However, more or fewer suction lumens 406 may be employed. In one non-limiting example, tubing 402 has an outside diameter of about 10 mm to about 12 mm and working channel 404 has a diameter of about 5 mm.

Figure 41B:
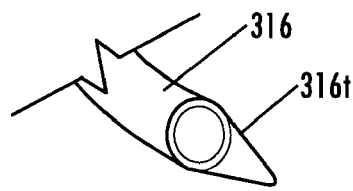

A flexible endoscope 316 is also shown extending distally of the distal end of tubing 402. Endoscope 316 is provided with a clear, trocar-type tip 316t that is configured to pierce through the wall of the stomach 120, while, at the same time, providing visualization of the procedure. FIG. 41B is an enlarged view of the distal end portion of endoscope 316, also showing endoscope tip 316t. In the example shown, endoscope 316 has an outside diameter of about 3 mm, although endoscopes of other sizes could be used.

Figure 41C:
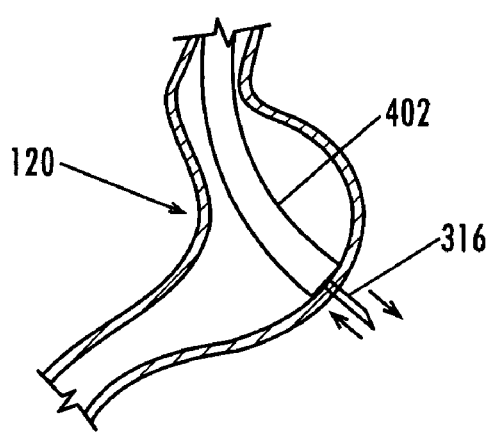
Figure 41D:
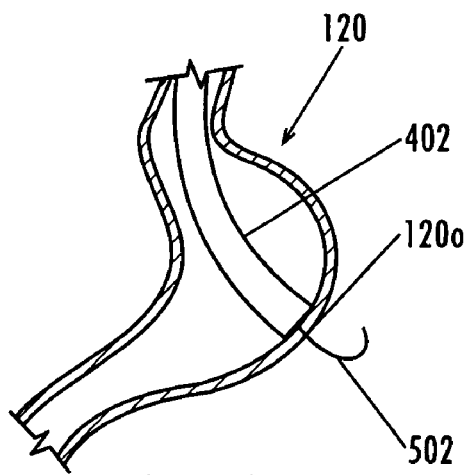

After inserting tubing 402 and endoscope 316 through the mouth 2, esophagus and into the stomach 120 (tubing 402 may be inserted first with endoscope 316 being inserted through tubing 402 after tubing 402 has already been placed, or, alternatively, endoscope 316 can be pre-positioned in tubing 402, but with the distal trocar tip of endoscope 316 being positioned proximally of the distal end of tubing 402 so as not to protrude therefrom, and then the components are inserted together) and orienting and positioning the distal end of tubing 402 so that it abuts against the stomach 120 wall in a location through which it is desired to deliver the implant device 10 (endoscope 316 may optionally be used to steer the distal end of tubing 402 to the desired contact location on the stomach 120, or, alternatively, tubing 402 may be provide with a stylet or self-steering mechanism like those provided with steerable endoscopes), suction is applied through the suction lumens 406 to attach the distal end of tubing 402 to the inner surface of the stomach wall. This suction attachment provides leverage for the next step of extending the distal end portion of endoscope 316 distally of the distal end of tubing 402, whereby endoscope tip 316t pierces through the wall of the stomach as illustrated in FIG. 41C. As the suction force of the suction lumens 406 on the stomach wall is in a direction opposite to the piercing force of the endoscope tip 316t, this helps to counteract the piercing force to facilitate formation of the opening 120o through the stomach 120.

While maintaining the suction attachment, endoscope tip 316t is retracted back into the stomach 120 and endoscope 316 is then removed from tubing 402 and the patient 1, all the while maintaining the suction attachment of the distal end of tubing 402 to the inner surface of the stomach 120 wall. Next, a floppy/soft tip guidewire 502 is inserted into working channel 5, and through the opening 120o in the stomach, as shown in FIG. 41C, so that a distal end portion is inserted into the intra-abdominal cavity and a proximal end portion of guidewire 502 extends proximally out of the proximal end of tubing 402 and out of the patient 1.

After placement of the guidewire 502 as described, the suction through suction lumens 406 is discontinued, and tubing 402 is withdrawn out of the patient while maintaining guidewire 502 substantially in its placed position. An anchor pad deployment assembly 410 is next delivered over the guidewire 502, through the mouth 2 of the patient, through the esophagus and into the stomach 120.

Figure 41E:
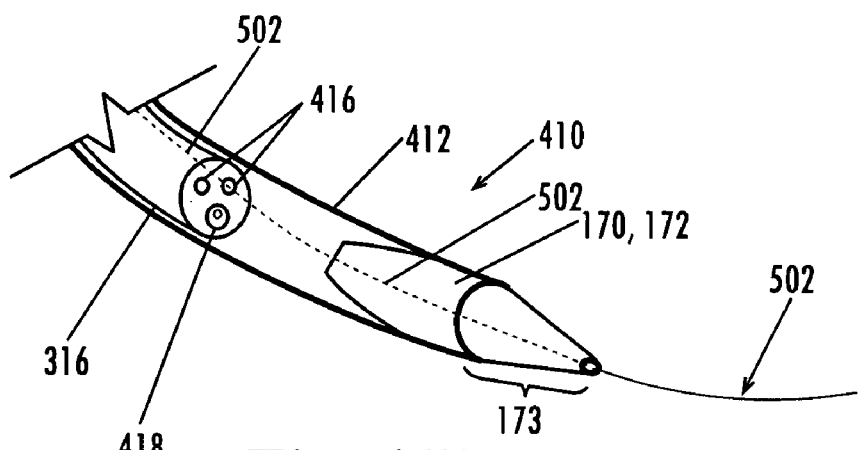
Figure 41F:
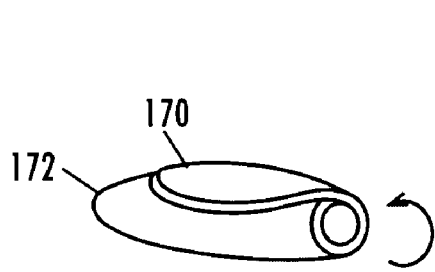
Figure 41G:
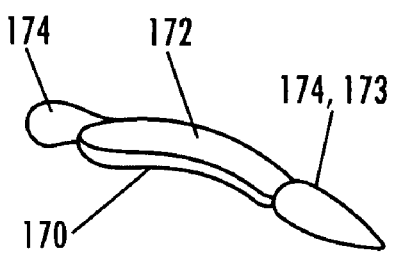

Anchor pad deployment assembly 410 is illustrated in FIG. 41E as being passed over guidewire 502. Attachment pad deployment assembly includes a flexible outer sheath 412 into which is inserted anchor pad or strip 170 and protective pad or strip 172 joined together in a manner as described above and provided in a compact configuration. A soft nose cone 414 is provided at a distal end of assembly 410 and may be incorporated into the attachment pad or strip design. FIG. 41F illustrates an anchor pad 170 and protective pad 172 assembly that has been arranged in a compact configuration by rolling up the assembly. Alternatively, a compact assembly may be provided solely by an anchor pad 170 (e.g., rolled up) or anchor strip 170 without a protective pad or strip 172. As noted above, anchors pad or strip 170 may be provided with one or more tabs 174, and in the case of an anchor strip 170, one of these pads may be formed as a nose cone 173 when protective strip 172 is not used. FIG. 41G illustrates an anchor strip 170 and protective strip 172 assembly in which one of the tabs 174 has been configured as the nosecone 173. Referring back to FIG. 41E, a flexible endoscope (gastroscope) 316 having working channels 416 and an endoscope viewing lumen/endoscope tip 418 is provided and is passed over guidewire 502 (through one of working channels 416) and into flexible sheath 412, proximally of anchor pad/strip 170 and protective pad/strip 172 assembly. In one non-limiting example, the outside diameter of gastroscope 316 is about 10 mm to about 12 mm.

Figures 41H, 41I:
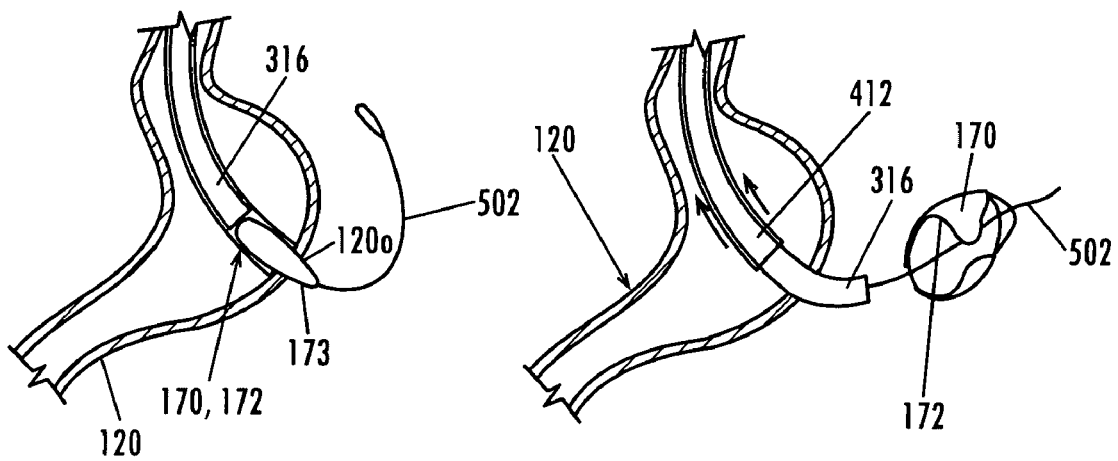

As the anchor pad assembly 410 is passed over the guidewire 502 and enters the stomach 120, nose cone 173 functions as a dilator as it passes through the opening 120o in the stomach 120, as illustrated in FIG. 41H. By pushing on the gastroscope 316, the distal end of the gastroscope 316 abuts against the proximal end of the compact assembly 170,172, thereby driving the soft nose cone 173 through and dilating opening 120o. In this example, the rolled up attachment pad 170 and protective pad 172 forms the nose cone 173 that functions to guide the assembly into and through the opening 120o as well as to dilate the opening 120o as it passes therethrough. Once the entire assembly 170,172 has been pushed through the opening 120o and into the abdominal cavity, at which point the distal tip of the gastroscope 316 will have also passed through the opening 120o across the wall of the stomach 120 and into the abdominal cavity, the flexible outer sheath 412 is retracted while maintaining the position of the gastroscope 316. Thus, when flexible outer sheath 412 has been removed from assembly 170,172, the anchor pad 170 and protective pad 172 deploy by unrolling to a non-compact, unrolled configuration. The beginning of this deployment is depicted in FIG. 41I.

Figure 41J:
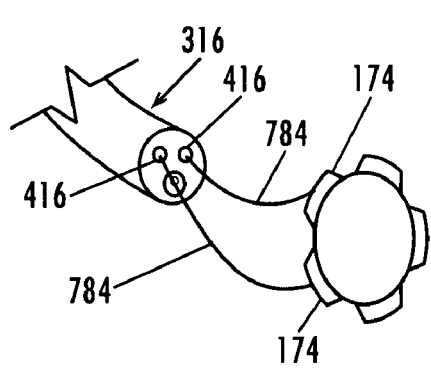

Using the working channels 416, tools are next inserted therethrough to position and orient the anchor pad assembly 170,172 against the internal abdominal structure(s) to which it is to be anchored, in this example, the inner surface of the anterior abdominal wall 127. Guidewire 502 may be removed to provide an additional working channel to insert a tool through, if needed, or may be left in place, if sufficient working channels already exist for enough tools to perform the task. If removed, guidewire 502 can later be reinserted or "exchanged". FIG. 41J shows a pair of graspers 784 having been inserted through working channels 416 and used to grasp tabs 174 and manipulated to position anchor pad 170 against the abdominal wall for anchoring thereto. Anchoring can be accomplished using helical tacks, or any of the other anchoring features described above with regard to FIG. 40Q, for example, with further supporting description being found in regard to FIGS. 33D-33F above.

After completion of anchoring of the anchor pad 170, any existing tools in working channels 416 can be removed and guidewire 502 is reinserted through one of the working channels 416 so as to extend a distal end portion of guidewire 502 into the abdominal cavity in preparation for delivery and implantation of device 10. Device 10 can be rolled up into a compact configuration and delivered in an assembly like that described above for delivery of the anchor pad/strip 170. Once device 10 has been inserted into the intra-abdominal cavity and deployed, one or more graspers can be inserted through one or more working channels 416 (guidewire 502 may be removed when two graspers are to be used. If a protective pad or strip 172 is attached to the anchor pad or strip having been previously anchored to an internal abdominal structure, then graspers 784 can be manipulated to grasp one or more tabs 174 attached to the protective pad/strip 172 and apply retraction force to peel the protective pad/strip 172 from contact to the anchor pad/strip. The protective pad or strip 172 can be removed from the patient 1 when the deployment assembly is removed, by maintaining it in the grasp of the graspers 784. Graspers 784 can further be used to properly position and orient device 10 so that anchoring pad/strip 179 contacts and anchors to anchor pad/strip 170.

At this time, gastroscope 316 and associated tools (as well as protective pad/strip 172, if present) can be removed through the opening 120o through the stomach wall and out of the patient 1. The opening 120o can then be closed by any of the techniques described above with regard to the FIG. 40 series. If device 10 is provided with an inflation conduit 12, as illustrated in FIG. 41K, it can be hooked and pulled out through the anterior abdominal wall 127 by percutaneous insertion of a hooked-needle type tool. An adjustment member 80 can then be fixed to the external surface/fascia external of the abdominal wall and used as a subcutaneous port to inflated expandable member 10em.

Figure 41L:
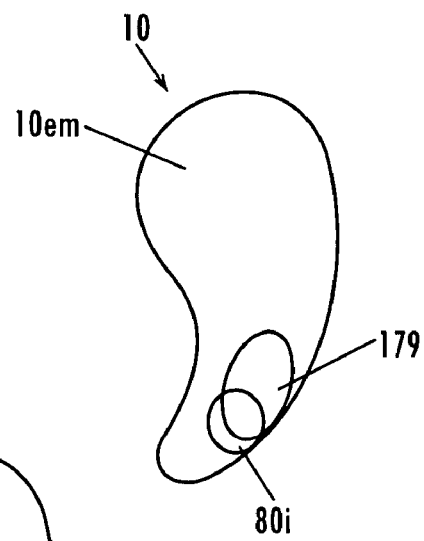
Figure 41K:
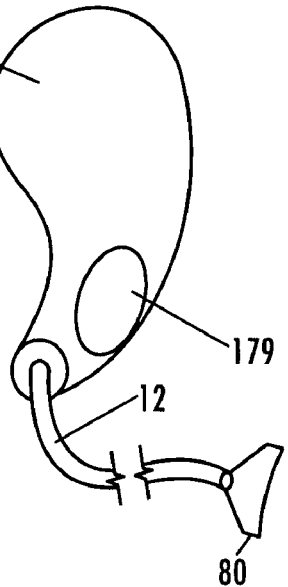

If device 10 is not provided with a conduit 12, but rather an integrated adjustment member 80i, as illustrated in FIG. 41L, then adjustment member 80i can be placed underlying or adjacent to anchoring pad/strip 179 and adjustment member can be accessed in the same manner described above with regard to FIG. 40X. Optionally, one or more magnets may be embedded into adjustment member 80i to facilitate locating the adjustment member from a location outside of the skin 125.

Figure 42A:
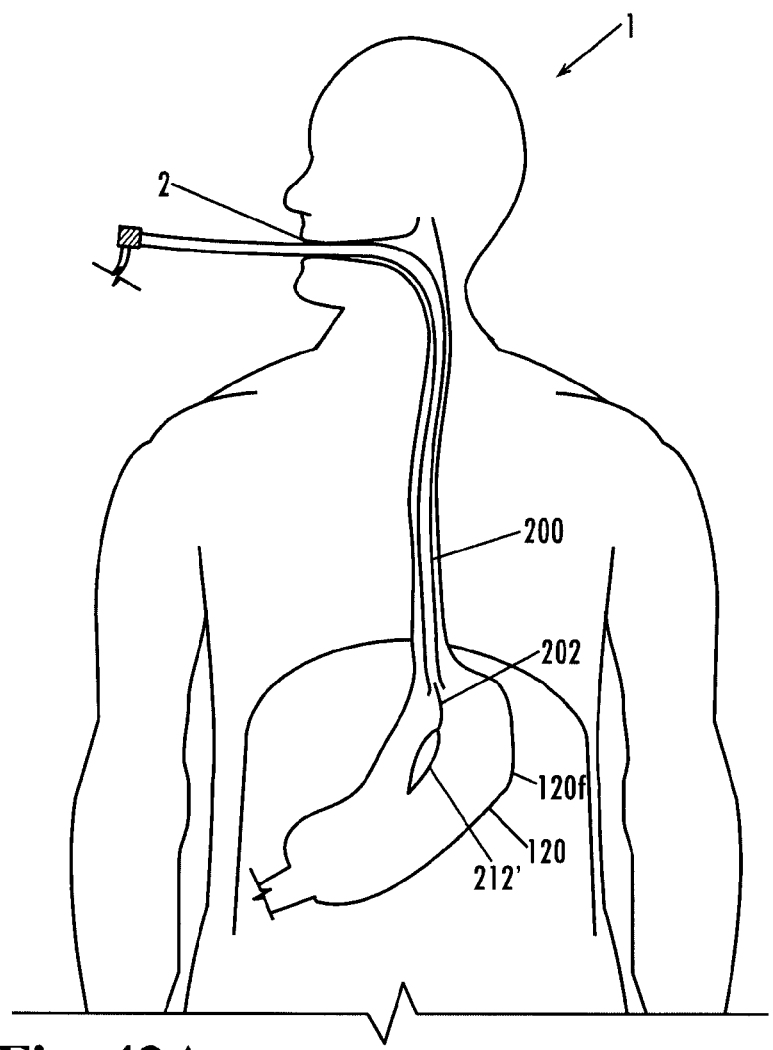
FIGS. 42A-42C illustrate steps that can be carried out in a method of implanting an intra-gastric device according to the present invention
Figure 42B:
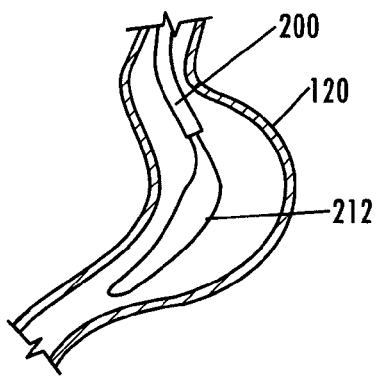
Figure 42C:
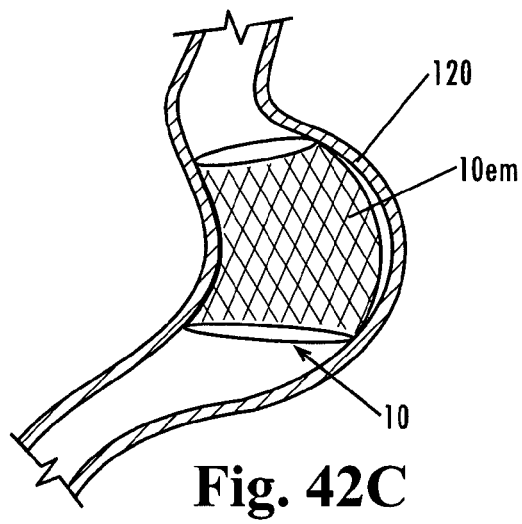

FIGS. 42A-42C illustrate steps of a method of implanting an intra gastric device 10 according to the present invention. It is commonly believed that when the stomach stretches due to filling of the stomach with food, the nerves in the stomach wall send a signal to the brain to tell the brain that the stomach is full and the brain lets the person know that he/she is full, by signaling a feeling of satiety, or fullness. In this approach, an expandable device is implanted in the cavity of the stomach and expanded to stretch the walls of the stomach to initiate the signals described. At FIG. 42A, a catheter 200 is inserted through the mouth 2 of a patient 1 and advanced down the esophagus and into the stomach, as illustrated. Once distal tip 202 has been positioned in the stomach cavity as desired, expandable member 10em, held in a compressed configuration, such as by a sheath 212, for example, as illustrated in FIGS. 42A-42B, is advanced through and out of the catheter 200. Alternatively, device 10/expandable member 10em can be passed over catheter 200 or a guide wire used in place of catheter 200 but installed similarly. Once device 10 has been delivered distally of the end of catheter 200 (or delivered by guide wire, as noted), sheath 212 is withdrawn, allowing expandable member 10em to expand as shown in FIG. 42C. Expandable member 10em in this example is a mechanically self-expanding member of a type as described above with regard to FIG. 10, for example. Alternatively, expandable member 10em may be an inflatable or composite member, as long as it is configured similarly, to provide a large opening passing therethrough. Thus, expandable member 10em is configured and dimensioned to stretch the stomach 120 to imitate a fully filled stomach, even when the contents of the stomach are empty. By stretching the walls of the stomach 120, the nerves in the stomach wall send a signal to the brain that the stomach is full, as noted above.

The forces exerted against the inner lining of the wall of the stomach 120 are sufficient to anchor device 10 and prevent it from migrating. Additionally, the outside diameters of the ends of expandable member 10em are significantly larger than the inside diameters of the esophagus and small intestine, and this acts as a mechanical anchor as device 10 is physically prevented from migrating either superiorly or inferiorly. Device 10 can be implanted permanently or indefinitely. Alternatively, device 10 may be placed as a temporary implant and removed trans orally after a predetermined amount of time, by compressing the expandable member and retrieving it. Thus, advantages of this technique include the fact that the procedure is minimally invasive, as no incisions are required at all to perform it. Also, since the device 10 is large in the expanded configuration, no additional anchoring or fixation structures are required, further simplifying the procedure and minimizing the invasiveness, since no suturing is required. The deployment is easy to perform and there is no risk of obstruction, since the lumen in the stomach cavity is actually increased by stretching the stomach walls. Also, the procedure is reversible, as noted.

Further, device 10 may be configured to intermittently contract and expand against the stomach wall. Such configuration may be accomplished with an inflatable device by providing a pump and valve arrangement that can be controlled to release pressure within the expandable device 10em and re-inflate device 10em at the intended times. Control can be automatic, or may be manually controlled by the patient. For example, a button or switch can be subcutaneously implanted which is electrically or mechanically connected to the inflation control mechanism, so that the patient can choose when to expand the device. For example, the patient may choose to expand the device upon commencement of eating, thereby signaling the brain that the stomach is full, so that the patient will eat much smaller portions during meal times. The device may be left expanded for some time after eating, say a half hour to an hour for example, and then contracted again, using the manual switch. A mechanically expanding expandable member 10em, may be similarly controlled, by providing a motor and mechanism to contract the device when desired, and to release contraction forces, allowing the device to self expand when desired.

Figure 43A:
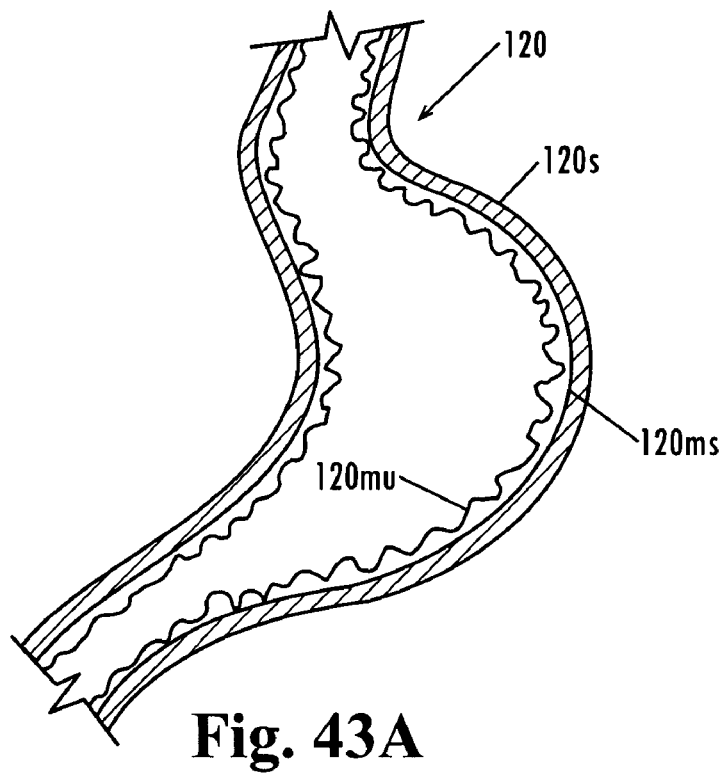
FIGS. 43A-43B illustrate steps that can be carried out for implantation of one or more devices according to another method of the present invention.
Figure 43B:
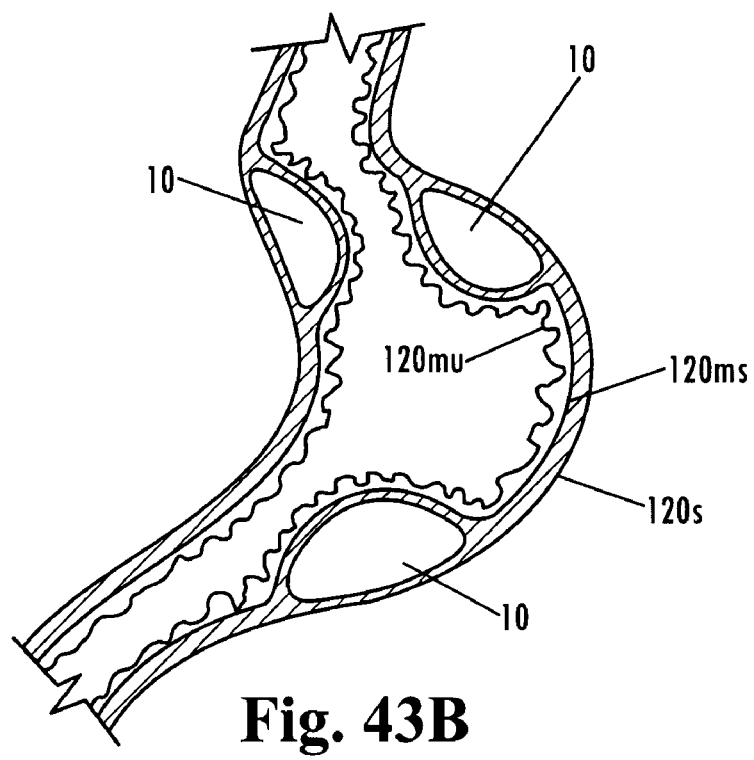

FIGS. 43A-43B illustrate steps of a method of decreasing the internal volume in the stomach cavity to function obstructively, restrictively, or both. The wall of the stomach 120 includes multiple layers, including the mucosa 120mu, muscularis 120ms and serosa 120s, as illustrated in FIG. 43A. This method separates two adjacent layers (e.g., serosa 120s and muscularis 120ms) at one or more locations to form pockets into which expandable devices 10 are implanted to reduce the volume of the stomach cavity inside the stomach 120. Implant 10 may be placed in a location to form an obstructive implant, as in the lowermost implant 10 shown in FIG. 43B. Alternatively, or additionally, implants 10 may be placed to perform a restrictive function, as in the pair of devices 10 implanted toward the top of the stomach, as illustrated in FIG. 43B. Alternatively, more than a pair of implants may be placed so as to substantially circumscribe the restriction that is formed by such placement.

Devices 10 may be inflatable, mechanically expandable, or a composite of these. Further alternatively, device 10 may be a rigid device configured and dimensioned in a shape to effect the desired amount of reduction of volume in the stomach cavity, upon implantation as described. Device 10 may also be of a non-compressible but flexible construction. For example, device 10 may contain a gel or other non-compressible fluid. Anchoring may be performed by suturing or otherwise closing the pocket after insertion of device 10, typically, prior to expanding expandable member, although closure may be made after such expansion. When an inflatable device 10 is used, conduit 12 (not shown) may be extended into the internal cavity of the stomach and an adjustment member may be placed, as described above with regard to the methods of FIGS. 39A-39G. Alternatively, conduit 12 may be passed externally of the stomach, and extended to an adjustment member 80 positioned outside of the abdominal muscles, for example. Further alternatively, expandable member may not have any conduit 12 left in place.

FIGS. 44A-44D illustrate steps of a method of forming an obstructive reduction in the volume of the cavity within the stomach by a trans-oral procedure. At FIG. 44A, a catheter 200 is inserted through the mouth 2 of a patient 1 and advanced down the esophagus and into the stomach, as illustrated. The distal tip 202 is maneuvered into contact with the inner lining of the stomach wall in a target location where the procedure is to be performed. The inner surface of the stomach may be grasped by suction. Alternatively, or additionally, a fixation tool 59, such as a cork screw tip, hook or other grasping implement may be fixed into the wall of the stomach to attach thereto. Alternatively, graspers may be delivered out of the distal tip 202 and used to grasp the wall of the stomach. In any of these alternatives, the stomach wall need not be completed penetrated. Further alternatively, an instrument may be used to pierce through the wall of the stomach to install a t-bar or other anchoring implement (or an expandable member 10em, which can be removed at the completion of the procedure) by which the wall of the stomach may be pulled inwardly by withdrawing the implement and catheter 200. A ring 214 is positioned over the distal end portion of catheter 200 and may be held in position by a shaft, wire of other controlling mechanism passing either internally of catheter 200 or along the outside thereof.

Figure 44A:
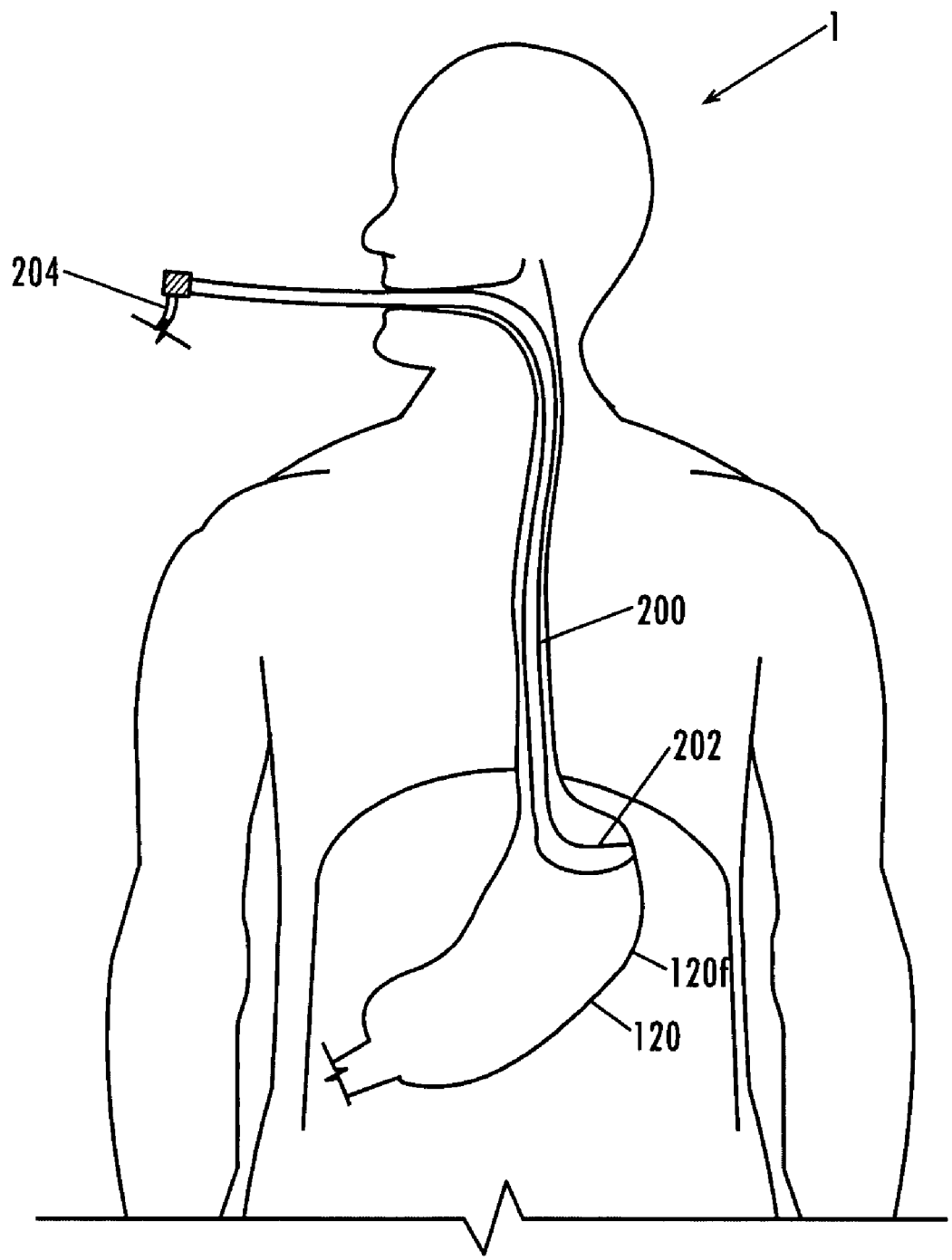
FIGS. 44A-44D illustrate steps that can be carried out to form one or more obstructions and/or restrictions in the cavity of the stomach, where no space-occupying implant is required.
Figure 44B:
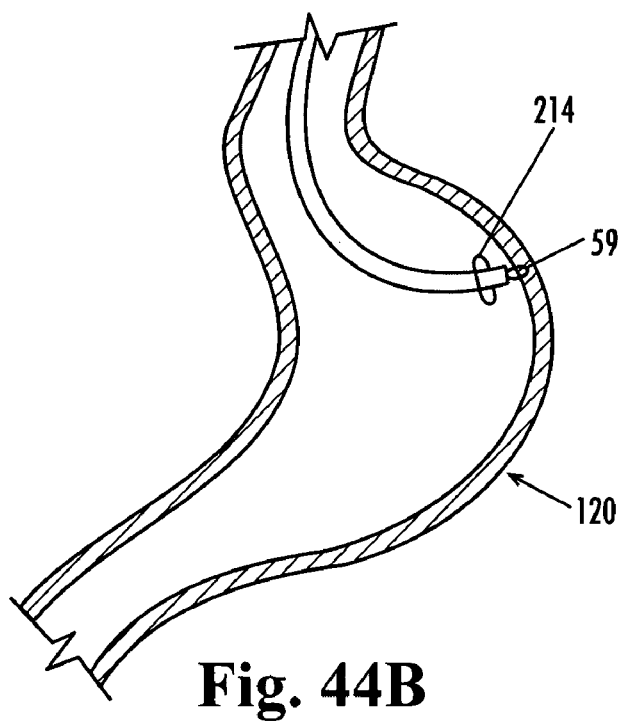
Figure 44C:
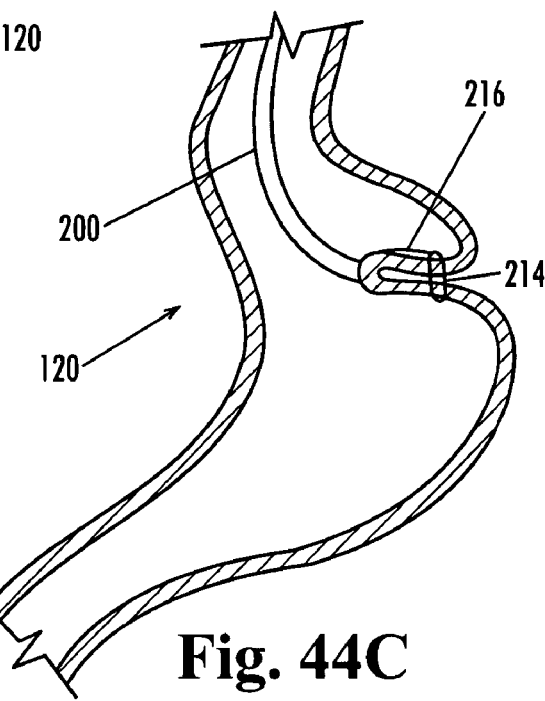

Once attachment to the wall of the stomach has been accomplished, the stomach wall is pulled inwardly by retracting catheter 200 while maintaining ring 214 in place, as illustrated in FIG. 44C. This causes the stomach wall to fold inward on itself, as it is drawn through ring 214. When the stomach wall has been sufficiently deformed as illustrated in FIG. 44C, as can be confirmed using any of the visualization techniques described earlier, and/or using gastric sizing member 310, ring 214 is manipulated to anchor the walls of the stomach in the deformed orientation shown in FIG. 44D, and catheter 200 is disconnected from the wall of the stomach and removed. Ring 214 may be inflatable to expand and exert compression forces against the walls of the stomach where it contacts them. Alternatively, ring 214 may be cinched down to mechanically exert the anchoring forces, such as in the form of a noose or snare, for example. Further alternatively, the walls may be further anchored by suturing them together (or stapling or other mechanical fixation) from either inside the stomach or outside the stomach 120.

Figure 44D:
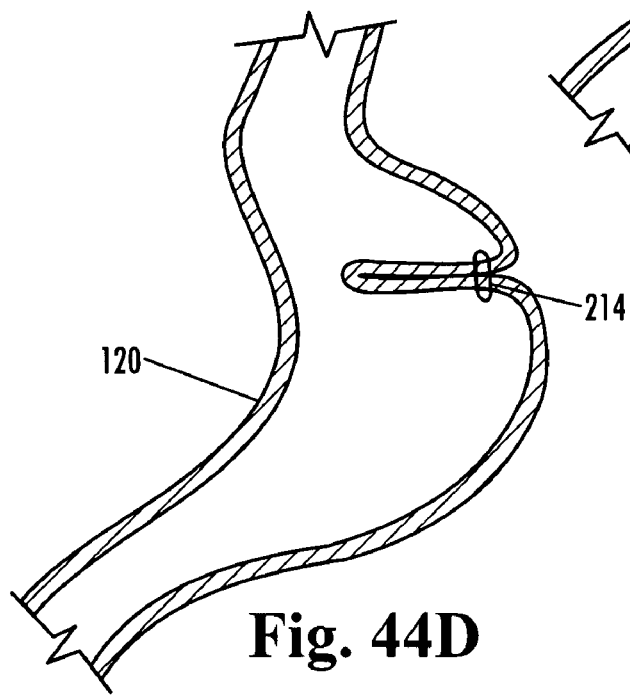

The resulting deformation shown FIG. 44D functions obstructively to reduce the volume of the cavity of the stomach and restrictively, by reducing the area of the lumen at this location. This method not only decreases the stomach volume, but fills up the decreased space with native stomach tissue, without the need to place an implant to take up the space for reducing cavity volume. This procedure may be performed multiple times. For example, two or more such deformations may be performed to operate together in making a restriction.

As an alternative to the method described with regard to FIGS. 44A-44D above, ring 214 can be omitted, as the pulling on the stomach wall by catheter 200 connected thereto will cause the deformation and inward folding of the stomach wall upon itself, without the need for the ring 214. Suturing or other anchoring can then be performed as described above, either from a location internal of the stomach, a location external of the stomach, or both, to maintain the folds of the stomach wall in the deformed conformation.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of treating obesity in a patient, said method comprising:
    passing an intra-gastric sizing device trans-orally into the patient and into the cavity of the stomach of the patient;
    pushing on the outer wall surface of the stomach with an instrument to deform the stomach wall inwardly, so that portions of the outer surface of the stomach wall fold inwardly upon one another, wherein the stomach wall is deformed by said pushing until contacting the intra-gastric sizing device;
    fixing the outer wall portions together to maintain an orientation wherein the folded wall portions face toward one another;
    expanding an expandable member to expand against the folded wall portions; and
    removing the instrument, while leaving the expanded expandable member in place.

2. A method of treating obesity in a patient, said method comprising:
    passing an intra-gastric sizing device trans-orally into the patient and into the cavity of the stomach;
    pushing on the outer wall surface of the stomach with an instrument to deform the stomach wall inwardly, so that portions of the outer surface of the stomach wall fold inwardly upon one another, wherein the stomach wall is deformed by said pushing until a signal from said intra-gastric device indicates that sufficient deformation has been accomplished;
    fixing the outer wall portions together to maintain an orientation wherein the folded wall portions face toward one another;
    expanding an expandable member to expand against the folded wall portions; and
    removing the instrument, while leaving the expanded expandable member in place.

3. A method of treating obesity in a patient, said method comprising:
    passing an intra-gastric sizing device trans-orally into the patient and into the cavity of the stomach of the patient;
    pushing on the outer wall surface of the stomach with an instrument to deform the stomach wall inwardly, so that portions of the outer surface of the stomach wall fold inwardly upon one another;
    monitoring an amount of deformation of the stomach wall inwardly;
    ceasing further deformation inwardly by said pushing when a predetermined distance between the inner surface of the stomach wall and the sizing member has been achieved; and
    fixing the outer wall portions together to maintain an orientation wherein the folded wall portions face toward one another;
    expanding an expandable member to expand against the folded wall portions; and
    removing the instrument, while leaving the expanded expandable member in place.

4. A method of treating obesity in a patient, said method comprising:
    pushing on the outer wall surface of the stomach with an instrument to deform the stomach wall inwardly, so that portions of the outer surface of the stomach wall fold inwardly upon one another;
    passing an intra-gastric sizing device trans-orally into the patient and into the cavity of the stomach, prior to said pushing, wherein the stomach wall is deformed by said pushing until contacting the intra-gastric sizing device;
    fixing the outer wall portions together to maintain an orientation wherein the folded wall portions face toward one another;
    expanding an expandable member mounted on a distal end portion of the instrument to expand against the folded wall portions; and
    removing the instrument, while leaving the expanded expandable member in place.

5. A method of treating obesity in a patient, said method comprising:
    pushing on the outer wall surface of the stomach with an instrument to deform the stomach wall inwardly, so that portions of the outer surface of the stomach wall fold inwardly upon one another;
    passing an intra-gastric sizing device trans-orally into the patient and into the cavity of the stomach, prior to said pushing, wherein the stomach wall is deformed by said pushing until a signal from said intra-gastric device indicates that sufficient deformation has been accomplished;
    fixing the outer wall portions together to maintain an orientation wherein the folded wall portions face toward one another;
    expanding an expandable member mounted on a distal end portion of the instrument to expand against the folded wall portions; and
    removing the instrument, while leaving the expanded expandable member in place.

* * * * *

UNITED STATES PATENT AND TRADEMARK OFFICE
CERTIFICATE OF CORRECTION

PATENT NO.       : 8,187,297 B2
APPLICATION NO.  : 11/881144
DATED            : May 29, 2012
INVENTOR(S)      : Makower et al.

It is certified that error appears in the above-identified patent and that said Letters Patent is hereby corrected as shown below:

On Title page, please delete "(73) Assignee: Vibsynt, Inc.," and insert --(73) Assignee: Vibrynt, Inc.--.

In the Drawings
On sheet 25/51 of the drawings, please delete Fig. 39A and insert Figs. 39A-39C as shown on the attachment hereto.

In the Specification
Column 7, line 50, please delete "an" and insert --and--;
Column 7, line 65, please delete "mount" and insert --mouth--;
Column 11, line 33, please delete "the an" and insert --the art--;
Column 21, line 33, please delete "release" and insert --released--;
Column 22, line 36, please delete "be optionally" and insert --optionally--;
Column 23, line 20, please delete "8011" and insert --80i1--;
Column 24, line 22, please delete "that" and insert --than--;
Column 25, line 3, please delete "opening" and insert --open--;
Column 35, line 56, delete "that" and insert --than--;
Column 41, line 56, after "observed" insert --by--;
Column 46, line 19, delete "advance" and insert --advanced--;
Column 47, line 18, delete "patient" and insert --patient 1--;
Column 48, line 11, delete "provide" and insert --provided--;
Column 48, line 39, delete "patient" and insert --patient 1--; and
Column 48, line 42, delete "patient" and insert --patient 1--.

Signed and Sealed this
Twenty-sixth Day of November, 2013

Margaret A. Focarino
*Commissioner for Patents of the United States Patent and Trademark Office*